(12) United States Patent
Thodeti et al.

(10) Patent No.: US 9,078,856 B2
(45) Date of Patent: Jul. 14, 2015

(54) IMPROVING EFFICACY OF CANCER THERAPY

(75) Inventors: Charles K. Thodeti, Copley, OH (US); Donald E. Ingber, Boston, MA (US)

(73) Assignee: CHILDREN'S MEDICAL CENTER CORPORATION, Boston, MA (US)

( * ) Notice: Subject to any disclaimer, the term of this patent is extended or adjusted under 35 U.S.C. 154(b) by 0 days.

(21) Appl. No.: 13/703,765

(22) PCT Filed: Jun. 22, 2011

(86) PCT No.: PCT/US2011/041368
§ 371 (c)(1), (2), (4) Date: Feb. 22, 2013

(87) PCT Pub. No.: WO2011/163312
PCT Pub. Date: Dec. 29, 2011

(65) Prior Publication Data
US 2013/0150432 A1    Jun. 13, 2013

Related U.S. Application Data

(60) Provisional application No. 61/357,123, filed on Jun. 22, 2010.

(51) Int. Cl.
| | |
|---|---|
| A61K 48/00 | (2006.01) |
| A61K 31/497 | (2006.01) |
| A61K 38/17 | (2006.01) |
| A61K 31/00 | (2006.01) |
| A61K 31/22 | (2006.01) |
| A61K 31/221 | (2006.01) |
| A61K 31/336 | (2006.01) |
| A61K 31/365 | (2006.01) |
| A61K 45/06 | (2006.01) |
| A61N 5/10 | (2006.01) |

(52) U.S. Cl.
CPC ............ *A61K 38/1709* (2013.01); *A61K 31/00* (2013.01); *A61K 31/22* (2013.01); *A61K 31/221* (2013.01); *A61K 31/336* (2013.01); *A61K 31/365* (2013.01); *A61K 38/177* (2013.01); *A61K 45/06* (2013.01); *A61N 5/10* (2013.01)

(58) Field of Classification Search
None
See application file for complete search history.

(56) References Cited

U.S. PATENT DOCUMENTS

| | | |
|---|---|---|
| 2005/0182011 A1 | 8/2005 | Olson et al. |
| 2013/0150432 A1* | 6/2013 | Thodeti et al. ............ 514/44 R |

FOREIGN PATENT DOCUMENTS

| | | |
|---|---|---|
| WO | 2007/073505 | 6/2007 |
| WO | 2009/149239 | 12/2009 |

OTHER PUBLICATIONS

Pla et al., Mol Cancer Res, 6:535-545 (2008). "Arachidonic acid-induced Ca2+ entry is involved in early steps of tumor angiogenesis."
Thodeti et al., Circ Res, 104(9):1123-1130 (2009). "TRPV4 channels mediate cyclic strain-induced endothelial cell reorientation through integrin to integrin signaling."
Alvarez, D. F. et al. Transient receptor potential vanilloid 4-mediated disruption of the alveolar septal barrier: a novel mechanism of acute lung injury. Circ Res 99, 988-95 (2006).
Ghosh et al., PNAS, 105(32):11305-11310 (2008). "Tumor-derived endothelial cells exhibit aberrant Rho-mediated mechanosensing and abnormal angiogenesis in vitro."
Ingber, D. Extracellular matrix and cell shape: potential control points for inhibition of angiogenesis. J. Cell Biochem 47, 236-41 (1991).
Inoue, R. et al. Transient receptor potential channels in cardiovascular function and disease. Circ. Res. 99, 119-31 (2006).
Kippenberger et al., The Journal of Biological Chemistry, 280(4):3060-3067 (2005). "Mechanical stretch stimulates protein kinase B/Akt."
Kohler, R. et al., Evidence for a functional role of endothelial transient receptor potential V4 in shear stress-induced vasodilatation. Arterioscler Thromb Vasc. Biol. 26, 1495-502 (2006).
Kwan et al., Biochimica et Biophysica Acta, 1772:907-914 (2007). "TRP channels in endothelial function and dysfunction."
O'Neil et al., Pflugers Arch-Eur J Physiol, 451:193-203 (2005).
Vriens et al., Cell Calcium, 36:19-28 (2004). "TRPV channels and modulation by hepatocyte growth factor/scatter in human hepatoblastoma (HepG2) cells."
Wang, N., Butler, J.P. & Ingber, D. E. Mechanotransduction across the cell surface and through the cytoskeleton. Science 260, 1124-7 (1993).

* cited by examiner

*Primary Examiner* — Michael Burkhart
(74) *Attorney, Agent, or Firm* — Nixon Peabody LLP; David S. Resnick

(57) ABSTRACT

Embodiments of the invention provide a method of improving the efficacy of an anti-cancer therapy and a method of treatment of cancer by normalizing angiogenesis in cancer. By enhancing the cell signaling pathway via a TRPV4 receptor in tumor endothelial cells, either by a TRPV4 agonist or by increasing the expression of TRPV4 in the tumor endothelial cells, the tumor endothelial cells behave normally and form normal angiogenic network for better anti-cancer therapy to the tumors.

6 Claims, 8 Drawing Sheets

IMPROVING EFFICACY OF CANCER THERAPY

CROSS-REFERENCE TO RELATED APPLICATIONS

This application is a 35 U.S.C. §371 National Phase Entry Application of International Application No. PCT/US2011/041,368 filed Jun. 22, 2011, which designates the U.S., and which claims benefit under 35 U.S.C. §119(e) of U.S. Provisional Application No. 61/357,123 filed Jun. 22, 2010, the contents of which are incorporated herein by reference in their entireties.

GOVERNMENT SUPPORT

This invention was made with Government support under Grant No.: CA 45548 awarded by the National Institutes of Health. The Government has certain rights in the invention.

REFERENCE TO SEQUENCE LISTING

This application contains a Sequence Listing which has been submitted in ASCII format via EFS-Web and is hereby incorporated by reference in its entirety. Said ASCII copy, created on Dec. 11, 2012, is named 20121212_SequenceListing-TextFile_701039_068352_US.txt and is 72,774 bytes in size.

BACKGROUND OF INVENTION

It is well known that the new network of blood vessels occurs in cancer and the network supplies nutrients that sustained the uncontrolled growth of abnormal cells in the body. However, it has been shown that these blood vessels are distinct from those of normal healthy tissues. The differences can affect the delivery and therefore the efficacy of anti-cancer therapy that targets the cancer cells, e.g, solid tumors.

The network of blood vessels and constituents in tumors has abnormal structures and functions. For example, the network of blood vessels have irregular morphology and pattern; the blood vessels tend to be thicker and have large clumps of tumor endothelial cells (TECs), the blood vessels are hyperpermeable ("leaky"), and the TECs have abnormally high basal level of active Rho, increased rate of cell migration, and aberrant mechanosensory response and orientation to external mechano-stimuli such as stretch stress when compared to non-cancer derived, normal endothelial cells (nECs). These abnormal TECs lead to abnormal angiogenesis in tumors, resulting in the irregular networks and "leaky" blood vessels. Many solid tumors show an increased interstitial fluid pressure (IFP) due to the irregular network, which forms a physical barrier to drug delivery, particular to the interior of a solid tumor. For example, the hyperpermeability of the tumor blood vessels creates a situation where a therapeutic effective amount of anti-cancer therapy fails to reach the target area because a substantial amount of the anti-cancer therapy has leaked out of the blood vessels enroute to the interior of a solid tumor. In addition, the irregular network affects blood flow rate and can impede a sustained delivery of an anti-cancer therapy to the target area. Therefore, innovations that address the abnormal angiogenesis, blood vessel network and abnormal characteristics of TECs in cancer can potentially impact the effectiveness of anti-cancer therapies.

SUMMARY OF THE INVENTION

Embodiments of the present invention are based on the discovery that tumor endothelial cells (TECs) have abnormal characteristics and responses compared to non-cancer or non-tumor associated normal endothelial cells (nECs) Unlike nECs, TECs express abnormally low levels of a stress-activated (SA) ion channel receptor TRPV4 compared to nECs (FIGS. 1A and 1B). These TECs also have reduced calcium influx upon stimulation of the TRPV4 receptor (FIGS. 1C and 1D). The inventors further discovered that over expression of TRPV4 in TECs normalizes the various abnormal characteristics of the TECs. For example, over expression of TRPV4 in TECs reduced the high basal level of active Rho (FIGS. 5A and 5B), decreased the TEC rate of migration (FIG. 3), and decreased aberrant mechanosensory and orientation response to external mechanic stimuli compared to TECs that were not overexpressing TRPV4 (FIG. 2). The inventors also found that the absence of TRPV4 in the TRPV4−/− knockout mice (KO) promoted increased aberrant angiogenesis that led to increased tumor growth in these mice (FIGS. 7 and 8).

Since the aberrant angiogenesis in tumors and abnormal TECs can be corrected by increasing TRPV4 expression, an approach that rectifies the TRPV4 expression deficiency in TECs can normalize angiogenesis in cancerous situations. Alternatively, an approach that increases the cell signaling pathway via a TRPV4 receptor in TECs can normalize angiogenesis as well as normalize the observed aberrant characteristics described herein. In addition, avenues for modulating the abnormal TECs characteristics and responses such that the characteristics and responses are closer to that of nECs can normalize angiogenesis in tumors. For example, methods of reducing the basal level of Rho activity, decreased the TEC rate of cell migration, and decreased aberrant mechanosensory and orientation response to external mechanic stimuli. Furthermore, methods of inhibiting the development of abnormal angiogenesis in a tumor can also normalize angiogenesis having blood vessels with less vascular leakage and networks that are closer to those formed by nECs, and this can improve the delivery of anti-cancer therapies to the tumor and thereby improve the efficacy of an anti-cancer therapy. Normalizing angiogenesis in tumors can also increased sensitization to anti-cancer therapy, e.g., radiosensitization for radiation therapy.

Accordingly, in one embodiment, provided here in is a TRPV4 agonist or a vector comprising a DNA sequence encoding a TRVP4 for increasing the efficacy of an anti-cancer treatment in a patient in need thereof.

In another embodiment, provided here in is a TRPV4 agonist or a vector comprising a DNA sequence encoding a TRVP4 for the treatment of cancer in a patient in need thereof.

In other embodiments, a TRPV4 agonist or a vector comprising a DNA sequence encoding a TRVP4 can be used for increasing the expression of a TRPV4 receptor in a TEC in a patient, increasing cell signaling via a TRPV4 receptor in a TEC in a patient, modulating the abnormal characteristics and responses of a TEC in a patient, reducing the basal level of active Rho of a TEC, in a patient, decreasing the rate of migration of a TEC, in a patient, decreasing aberrant mechanosensory and orientation responses to external mechanic stimuli of a TEC in a patient, inhibiting the development of abnormal angiogenesis in a tumor in a patient, inhibiting tumor growth in a patient, reducing vascular leakage in a tumor of a patient, for normalizing angiogenesis in a patient and enhancing the radiosensitivity of a tumor to radiation therapy in a patient.

In one embodiment, provided here in is a method for increasing the efficacy of an anti-cancer treatment in a patient in need thereof, the method comprising administering a TRPV4 agonist or a vector comprising a DNA sequence encoding TRVP4 to the patient concurrently with a cancer treatment or subsequently administering the cancer treatment to the patient.

In one embodiment, provided here in is a method for cancer treatment in a patient in need thereof, the method comprising administering a TRPV4 agonist or a vector comprising a DNA sequence encoding TRVP4 to the patient concurrently with a cancer treatment or subsequently administering the cancer treatment to the patient.

In one embodiment of the methods described, the method further comprises selecting a patient who has been diagnosed with cancer. In one embodiment, the patient is diagnosed with cancer. In other embodiments, the patient is about to start a cancer treatment or is being treated with the cancer treatment.

In one embodiment, the TRPV4 agonist or a vector is administered concurrently with an anti-cancer treatment or the anti-cancer treatment is administered subsequently.

In one embodiment, the TRPV4 agonist is selected from a group consisting of GSK1016790A, Bisandrographolide A (BAA), RN 1747, AB1644034, α-phorbol 12,13-didecanoate (4αPDD) 5,6-EET, acetylcholine and App441-1.

In one embodiment, the TRVP4 is a human TRVP4.

In one embodiment, the human TRVP4 is SEQ. ID. NO. 3, 4 or 5.

In one embodiment, the cancer treatment is chemotherapy, radiation therapy and/or immunotherapy.

As used herein, "cancer" refers to any of various malignant neoplasms characterized by the proliferation of anaplastic cells that tend to invade surrounding tissue and metastasize to new body sites and also refers to the pathological condition characterized by such malignant neoplastic growths.

As used herein, "normalizes" when used in reference to a tumor endothelial cell's characteristics such as basal level of active Rho, endothelial cell rate of migration, and mechanosensory and orientation response to external mechanic stimuli, vascular leakage etc refers to characteristics that are similar or close to that of normal, non-tumor, non-cancer derived endothelial cells (nEC) or structures form by nECs. The use of a TRPV4 agonist or a vector comprising a DNA sequence encoding a TRVP4 for the methods and uses described can normalize the TEC anywhere from 5% to 100% close to that of nECs. In one embodiment, the TEC's characteristic is normalized such that there is no difference from that of a nEC.

In one embodiment, as used herein, "normalize angiogenesis" and "normalizing angiogenesis" when used in reference to TECs refers to the normal tubular network formation when the TECs are plated at high cell density instead of the TEC forming multicellular clumps without any tubular network formation. Normal tubular network formation occurs for nEC when they are plated at high density. TECs exhibiting "normalized angiogenesis" will make tubular network instead of forming multicellular clumps. (See FIG. 6) The use of a TRPV4 agonist or a vector comprising a DNA sequence encoding a TRVP4 for the methods and uses described can normalize angiogenesis by TEC anywhere from 5% to 100%.

As used herein, "radiosensitization for radiation therapy" refers to making tumors more sensitive to radiation emission such that a lower dose of radiation is sufficient to effect more cell death in the tumor compared to prior to radiosensitization.

DETAILED DESCRIPTION OF THE INVENTION

Figure 7:
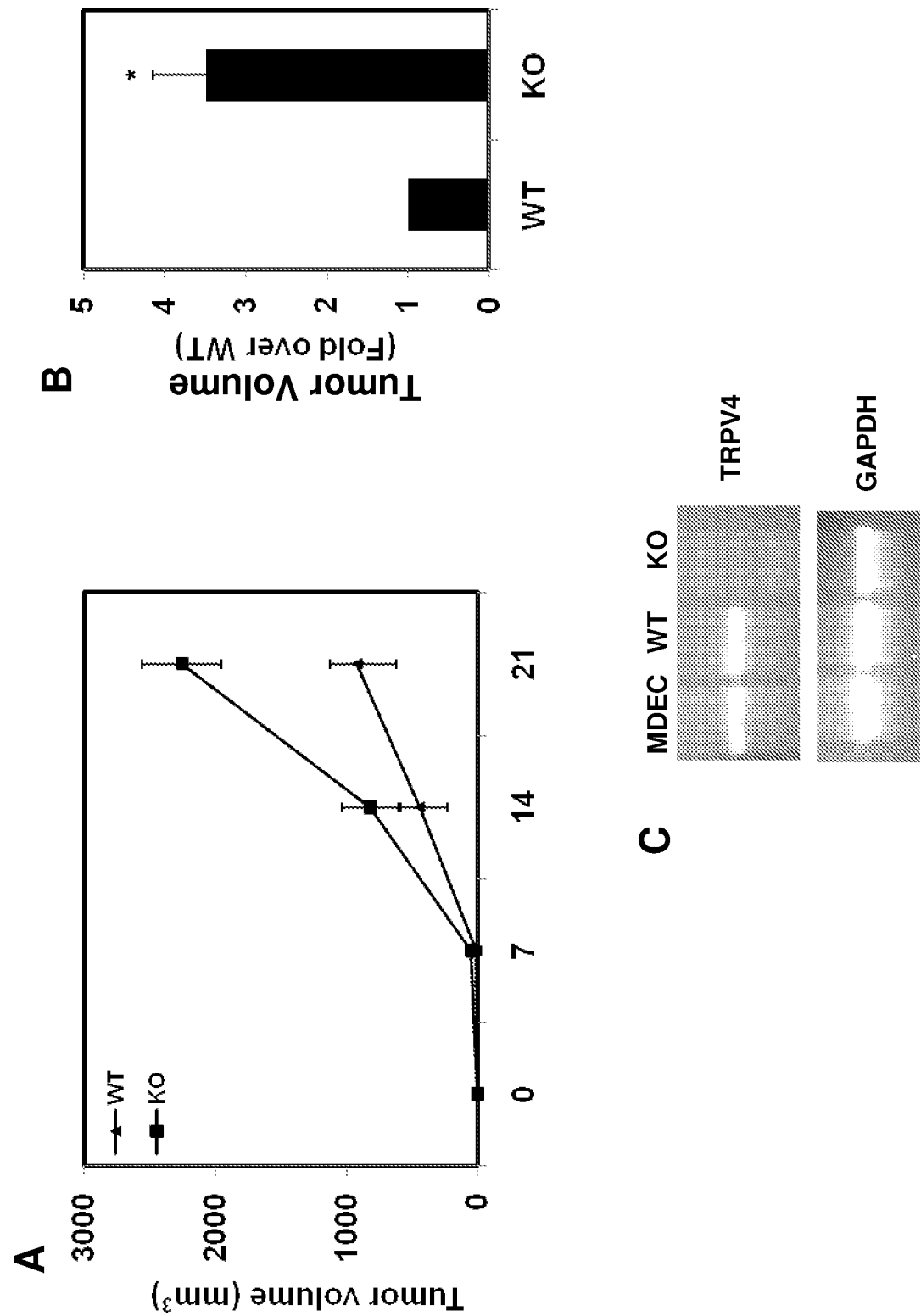
FIG. 7A is a graph showing that the tumor growth is enhanced in TRPV4 knockout mice (KO) compared to control mice (WT) expressing endogenous amounts of TRPV4. The data shown are +SEM of three independent experiments (n=11 mice for each group).
FIG. 7B is a histogram showing that the tumor growth is enhanced in TRPV4 knockout mice (KO) compared to control mice (WT) expressing endogenous amounts of TRPV4.
FIG. 7C shows RT-PCR analysis demonstrating the TRPV4 expression is absent in TRPV4 knockout mice (KO) compared to control mice (WT) expressing endogenous amounts of TRPV4.
Figure 8:
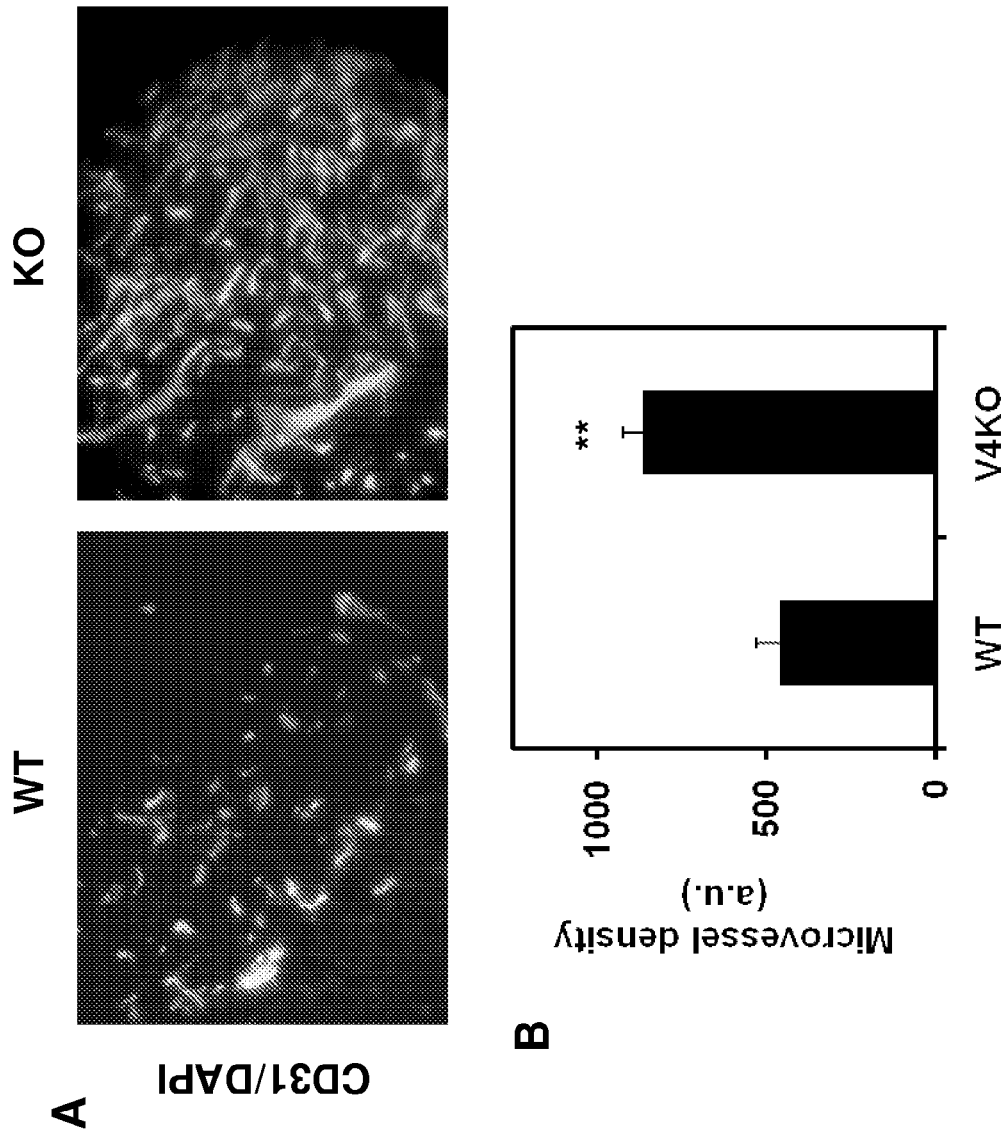
FIG. 8A contains fluorescence micrographs showing the blood microvessel density and vessel thickness are increased in subcutaneously implanted tumor cells in TRPV4 knockout mice (KO) compared to subcutaneously implanted tumor cells in control mice (WT) expressing endogenous amounts of TRPV4.
FIG. 8B is a histogram showing that quantitative analysis of blood microvessel density of the subcutaneously implanted tumor is increased in TRPV4 knockout mice (KO) compared to subcutaneously implanted tumors in control mice (WT) expressing endogenous amounts of TRPV4.

Embodiments of the present invention are based on the discovery that tumor endothelial cells (TECs) have abnormal characteristics and responses compared to non-cancer or non-tumor associated normal endothelial cells (nECs) Unlike nECs, TECs express abnormally low levels of a stress-activated (SA) ion channel receptor TRPV4 compared to nECs (FIGS. 1A and 1B). These TECs also have reduced calcium influx upon stimulation of the TRPV4 receptor (FIGS. 1C and 1D). The inventors further discovered that over expression of TRPV4 in TECs normalizes the various abnormal characteristics of the TECs. For example, over expression of TRPV4 in TECs reduced the high basal level of active Rho (FIGS. 5A and 5B), decreased the TEC rate of migration (FIG. 3), and decreased aberrant mechanosensory and orientation response to external mechanic stimuli compared to TECs that were not overexpressing TRPV4 (FIG. 2). The inventors also found that the absence of TRPV4 in the TRPV4−/− knockout mice (KO) promoted increased aberrant angiogenesis that led to increased tumor growth in these mice (FIGS. 7 and 8).

Since the aberrant angiogenesis in tumors and abnormal TECs can be corrected by increasing TRPV4 expression, an approach that rectifies the TRPV4 expression deficiency in TECs can normalize angiogenesis in cancerous situations. Alternatively, an approach that increases the cell signaling pathway via a TRPV4 receptor in TECs can normalize angiogenesis as well as normalize the observed abberent characteristics described herein. In addition, avenues for modulating the abnormal TECs characteristics and responses such that the characteristics and responses are closer to that of nECs can normalize angiogenesis in tumors. For example, methods of reducing the basal level of Rho activity, decreased the TEC rate of cell migration, and decreased aberrant mechanosensory and orientation response to external mechanic stimuli. Furthermore, methods of inhibiting the development of abnormal angiogenesis in a tumor can also normalize angiogenesis having blood vessels with less vascular leakage and networks that are closer to those formed by nECs, and this can improve the delivery of anti-cancer therapies to the tumor and thereby improve the efficacy of an anti-cancer therapy. Normalizing angiogenesis in tumors can also increased sensitization to anti-cancer therapy, e.g., radiosensitization for radiation therapy.

Accordingly, provided herein is a method of improving the efficacy of an anti-cancer therapy by normalizing angiogenesis in cancer situations, e.g., in a patient having cancer. By enhancing a TRPV4 cell signaling pathway in TECs, either by a TRPV4 agonist or by increasing the expression of TRPV4 in the TECs, the TECs exhibit less abnormal endothelial characteristics and form angiogenic network that are closer to the networks of nECs for a more effective delivery of anti-cancer therapy to the tumors.

In one embodiment, provided herein is a method for increasing the efficacy of an anti-cancer treatment in a patient in need thereof, the method comprises administering a TRPV4 agonist or a vector comprising a DNA sequence encoding TRPV4 to the patient concurrently with a cancer treatment or subsequently administering the cancer treatment to the patient. In one embodiment, the patient is diagnosed with cancer. In other embodiments, the patient is about to start a cancer treatment or is being treated with the cancer treatment. In one embodiment, the increased in efficacy of the anti-cancer treatment in the patient is at least 5% compared to a control reference. In some embodiments, the increased in efficacy is at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 99%, or at least 100% compared to the control reference, including all the percentages to the second decimal place between 5%-100%.

In one embodiment, provided herein is a method for increasing the expression of a TRPV4 receptor in a TEC in a patient in need thereof, the method comprises administering a vector comprising a DNA sequence encoding a TRPV4 to the patient. In one embodiment, the vector is administered concurrently with a cancer treatment or the cancer treatment is administered subsequently to the patient after the vector. In one embodiment, the patient is diagnosed with cancer. In other embodiments, the patient is about to start a cancer treatment or is being treated with the cancer treatment. In one embodiment, the increased in expression of TRPV4 is at least 5% compared a control reference. In some embodiments, the increased in TRPV4 expression in TECs is at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 99%, or at least 100% of the control reference, including all the percentages to the second decimal places between 5-100%.

In another embodiment, provided herein is a method for increasing cell signaling via a TRPV4 receptor in a TEC in a patient in need thereof, the method comprises administering a TRPV4 agonist or a vector comprising a DNA sequence encoding a TRPV4 to the patient. In one embodiment, the TRPV4 agonist or vector is administered concurrently with a cancer treatment or the cancer treatment is administered subsequently to the patient after the TRPV4 agonist. In other embodiments, the patient is about to start a cancer treatment or is being treated with the cancer treatment. In one embodiment, the increased in cell signaling is measured as an increase in calcium influx in the TECs of a patient administered a TRPV4 agonist or vector compared to the TECs of a control patient not administered a TRPV4 agonist or a vector comprising a DNA sequence encoding a TRPV4. In one embodiment, the patient is diagnosed with cancer. In one embodiment, the increase in cell signaling, calcium influx in the TECs of the patient administered with a TRPV4 agonist is at least 5% compared to a control reference. In some embodiments, the increase is at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 99%, or at least 100% or more than the control reference, including all the percentages to the second decimal places between 5-100%.

In one embodiment, provided herein is a method for modulating the abnormal characteristics and responses of a TEC in a patient in need thereof, the method comprises administering a TRPV4 agonist or a vector comprising a DNA sequence encoding TRPV4 to the patient concurrently with a cancer treatment or subsequently administering the cancer treatment to the patient. In one embodiment, the modulation of the TEC is towards the normal characteristics and responses of a non-cancerous, nEC. In another embodiment, provided herein is a method for normalizing the abnormal characteristics and responses of a TEC in a patient in need thereof, the method comprises administering a TRPV4 agonist or a vector comprising a DNA sequence encoding TRPV4 to the patient concurrently with a cancer treatment or subsequently administering the cancer treatment to the patient. In one embodiment, the modulation of the TEC is negative whereby the characteristics and responses of the TEC is closer to that of a non-cancerous, nEC. For example, the modulated TEC has reduced the basal level of Rho activity, decreased the TEC rate of migration, and decreased aberrant mechanosensory and orientation response to external mechanic stimuli compared to control TEC not activated by a TRPV4 agonist or a vector comprising a DNA sequence encoding TRPV4. In some embodiments, the characteristics and responses of TEC that is modulated are the basal level of Rho activity, the TEC rate of migration, and the mechanosensory and orientation response to external mechanic stimuli. In one embodiment, the modulated TEC is at least 5% closer to a control reference. In some embodiments, the characteristics and responses of endothelial cells are measured in terms of basal level of active Rho, endothelial cell rate of migration, and mechanosensory and orientation response to external mechanic stimuli. In some embodiments, the modulated TEC is at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 99%, or at least 100% closer to the control reference, including all the percentages to the second decimal places between 5-100%. In one embodiment, the patient is diagnosed with cancer. In other embodiments, the patient is about to start a cancer treatment or is being treated with the cancer treatment.

In one embodiment, provided herein is a method for reducing the basal level of active Rho of a TEC in a patient in need thereof, the method comprises administering a TRPV4 agonist or a vector comprising a DNA sequence encoding TRPV4 to the patient concurrently with a cancer treatment or subsequently administering the cancer treatment to the patient. In another embodiment, provided herein is a method for normalizing the basal level of active Rho of a TEC, in a patient in need thereof, the method comprises administering a TRPV4 agonist or a vector comprising a DNA sequence encoding TRPV4 to the patient concurrently with a cancer treatment or subsequently administering the cancer treatment to the patient. In one embodiment, the reduction or normalization is such that the basal level of Rho activity in the TEC is at least 5% closer to a control reference. In one embodiment, the control reference is the basal level of Rho activity in nECs. In some embodiments, the reduction or normalization of Rho activity in TECs is at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 99%, or at least 100% closer to the control reference, including all the percentages to the second decimal places between 5-100%. In one embodiment, the patient is diagnosed with cancer. In other embodiments, the patient is about to start a cancer treatment or is being treated with the cancer treatment.

In one embodiment, provided herein is a method for decreasing the rate of migration of a TEC in a patient in need thereof, the method comprises administering a TRPV4 agonist or a vector comprising a DNA sequence encoding TRPV4 to the patient concurrently with a cancer treatment or subsequently administering the cancer treatment to the patient. In another embodiment, provided herein is a method for normalizing the rate of migration of a TEC, in a patient in need thereof, the method comprises administering a TRPV4 agonist or a vector comprising a DNA sequence encoding TRPV4 to the patient concurrently with a cancer treatment or subsequently administering the cancer treatment to the patient. In one embodiment, the decreased or normalized rate of migration is at least 5% closer to a control reference. In one embodiment, the control reference is the average migrate rate of TECs in patients not treated with a TRPV4 agonist or a vector comprising a DNA sequence encoding TRPV4. In another embodiment, the control reference is average cell migration rate of nECs. In some embodiments, the decreased or normalized rate of migration is at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 99%, or at least 100% closer to the control reference, including all the percentages to the second decimal places between 5-100%. In one embodiment, the patient is diagnosed with cancer. In other embodiments, the patient is about to start a cancer treatment or is being treated with the cancer treatment.

In one embodiment, provided herein is a method for decreasing aberrant mechanosensory and orientation responses to external mechanic stimuli of a TEC in a patient in need thereof, the method comprises administering a TRPV4 agonist or a vector comprising a DNA sequence encoding TRPV4 to the patient concurrently with a cancer treatment or subsequently administering the cancer treatment to the patient. In another embodiment, provided herein is a method for normalizing aberrant mechanosensory and orientation responses to external mechanic stimuli of a TEC in a patient in need thereof, the method comprises administering a TRPV4 agonist or a vector comprising a DNA sequence encoding TRPV4 to the patient concurrently with a cancer treatment or subsequently administering the cancer treatment to the patient. The normalized mechanosensory and orientation responses would be closer to those of nECs. In one embodiment, the decreased or normalized aberrant mechanosensory and orientation responses is at least 5% closer to a control reference. In one embodiment, the control reference is the average mechanosensory and orientation responses to external mechanic stimuli of nECs. In some embodiments, the decreased or normalized aberrant mechanosensory and orientation responses is at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 99%, or at least 100% closer to the control reference, including all the percentages to the second decimal places between 5-100%. In one embodiment, the patient is diagnosed with cancer. In other embodiments, the patient is about to start a cancer treatment or is being treated with the cancer treatment.

In one embodiment, provided herein is a method for inhibiting the development of abnormal angiogenesis in a tumor in a patient in need thereof, the method comprises administering a TRPV4 agonist or a vector comprising a DNA sequence encoding TRPV4 to the patient concurrently with a cancer treatment or subsequently administering the cancer treatment to the patient. In one embodiment, the method comprises contacting the tumor with a TRPV4 agonist or a vector comprising a DNA sequence encoding TRPV4. For example, directly injecting the TRPV4 agonist or vector into the tumor in the patient. In one embodiment, the patient is diagnosed with cancer. In other embodiments, the patient is about to start a cancer treatment or is being treated with the cancer treatment. In some embodiments, the inhibition of the development of abnormal angiogenesis in a tumor is measured in terms of basal level of active Rho, endothelial cell rate of migration, and mechanosensory and orientation response to external mechanic stimuli of a TEC in the patient. For example, the TECs of a patient administered with a TRPV4 agonist or a vector comprising a DNA sequence encoding TRPV4 are isolated and assayed for Rho activity, cell migration rate, and mechanosensory and orientation responses no external stimuli. These TECs would have reduced the basal level of active Rho, decreased the TEC rate of migration, and decreased aberrant mechanosensory and orientation response to external mechanic stimuli compared to the TECs of a patient to whom the TRPV4 agonist or a vector comprising a DNA sequence encoding TRPV4 was not administered. In another embodiment, the inhibition of the development of abnormal angiogenesis in a tumor is assessed by an in vitro angiogenesis assay of the isolated TECs before and after the application of the TRPV4 agonist or a vector. These TECs would have reduced multicellular retractions and cell clumping and increased tube formation. In another embodiment, the inhibition of the development of abnormal angiogenesis in a tumor is measured by imaging the network of blood vessels in the tumor before and after the application of the TRPV4 agonist or vector. The network of blood vessels in the tumors would be less thick with large clumps of TECs. In one embodiment, the inhibition of the development of abnormal angiogenesis in a tumor is inhibited by at least 5% closer compared to a control reference. In one embodiment, the control reference is the average abnormal angiogenesis in tumors of patients not administered the TRPV4 agonist or a vector described herein.

In some embodiments, the inhibition of the development of abnormal angiogenesis in a tumor is inhibited by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 99%, or at least 100% compared to the control reference, including all the percentages to the second decimal places between 5-100%.

Methods of assessing angiogenesis are known to those skilled in the art, such as, in vitro cell migration and capillary tube formation as described by Nicosia R. F. and Ottinetti A., (In Vitro Cell Dev. Biol., 1990, 26:119-128), Ghosh et al., (PNAS, 2008, 105:11305-11310), Lingen MW, (Methods Mol. Med. 2003, 78:337-47), and McGonigle and Shifrin, (Curr. Prot. Pharmacology, 2008, Unit 12.12). Other methods include but are not limited to dynamic contrast-enhanced MRI (DCE-MRI) which can be used to demonstrate tissue perfusion and permeability. Moreover, MRI with macromolecular contrast media (MMCM) can depict microvessel permeability and fractional plasma volume. (Padhani, A. R., British Journal of Radiology (2003) 76, S60-S80).

The level of angiogenesis and/or the network of blood vessels in the tumors in patients can be measured by micro-CT angiography with contrast reagents, dynamic contrast-enhanced MRI (DCE-MRI) and MRI with macromolecular contrast media (MMCM). Examples of contrast reagents for use with these imaging methods include by are not limited to the low molecular weight Gd(III) contrast reagents such as gadoteridol and the macromolecular iron oxide CRs such as ferumoxytol.

In some embodiments, commercial angiogenesis assays can be used. For example, the MATRIGEL™ assay where ECs are plated in wells coated with MATRIGEL™ (Becton Dickinson, Cedex, France). Alternatively, an in vitro angiogenesis assay kit marketed by CHEMICON® can be used. The Fibrin Gel In Vitro Angiogenesis Assay Kit is CHEMICON® Catalog No. ECM630.

In one embodiment, the inhibition of abnormal angiogenesis is such that there is at least 5% reduction in Rho activity, cell migration rate, and/or mechanosensory and orientation responses no external stimuli compared to nEC or at least 5% reduction in the multicellular retractions, cell clumping and/or thickness of the blood vessels in the tumor compared to the TECs or network of blood vessels before the application of the TRPV4 agonist or vector. In some embodiments, the inhibition of abnormal angiogenesis is at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 99%, or at least 100% reduction in Rho activity, cell migration rate, and mechanosensory and orientation responses no external stimuli compared to nEC orreduction in the multicellular retractions, cell clumping and/or thickness of the blood vessels in the tumor compared to the TECs or network of blood vessels before the application of the TRPV4 agonist or vector, including all the percentages to the second decimal places between 5-100%.

The inventors found that the absence of TRPV4 in the TRPV4-/- knockout mice promoted increased aberrant angiogenesis in tumors which led to increased tumor growth in these mice. While not wishing to be bound by theory, increased TRPV4 expression or cell signaling in TECs via TRPV4 can inhibit aberrant angiogenesis which can lead to the inhibition of tumor growth.

In one embodiment, provided herein is a method for inhibiting tumor growth in a patient in need thereof, the method comprises administering a TRPV4 agonist or a vector comprising a DNA sequence encoding TRPV4 to the patient concurrently with a cancer treatment or subsequently administering the cancer treatment to the patient. In one embodiment, the method comprises contacting the tumor with a TRPV4 agonist or a vector comprising a DNA sequence encoding TRPV4. For example, directly injecting the TRPV4 agonist or the vector into the tumor in the patient. In one embodiment, the patient is diagnosed with cancer. In other embodiments, the patient is about to start a cancer treatment or is being treated with the cancer treatment. In one embodiment, the tumor growth is reduced by at least 5% compared to the tumor size prior to administration of the TRPV4 agonist or vector. In some embodiments, the tumor growth is reduced by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 99%, or at least 100% compared to the tumor size prior to administration of the TRPV4 agonist or vector, including all the percentages to the second decimal places between 5-100%. In one embodiment, the inhibition is complete absence or disappearance of the tumor by currently detection method. Methods of measuring the size of a tumor in a patient are well known to a skill clinician, physician or oncologist. For example, MRI, CAT scanning (CT), X-ray, mammography and $^{18}$F-FDG PET scans.

In another embodiment, provided herein is a method for treatment of cancer in a patient in need thereof, the method comprises administering a TRPV4 agonist or a vector comprising a DNA sequence encoding TRPV4 to the patient concurrently with a cancer treatment or subsequently administering the cancer treatment to the patient. In one embodiment, the method comprises contacting the tumor with a TRPV4 agonist or a vector comprising a DNA sequence encoding TRPV4. For example, directly injecting the TRPV4 agonist or the vector into the tumor in the patient. In one embodiment, the patient is diagnosed with cancer. In other embodiments, the patient is about to start a cancer treatment or is being treated with the cancer treatment. Efficacy of the treatment can be determined by any methods that are known in the art and those described herein.

In another embodiment, provided herein is a method for reducing vascular leakage in a tumor of a patient in need thereof, the method comprises administering a TRPV4 agonist or a vector comprising a DNA sequence encoding TRPV4 to the patient concurrently with a cancer treatment or subsequently administering the cancer treatment to the patient. In one embodiment, the method comprises contacting the tumor with a TRPV4 agonist or a vector comprising a DNA sequence encoding TRPV4. For example, directly injecting the TRPV4 agonist or the vector into the tumor in the patient. In one embodiment, the patient is diagnosed with cancer. In other embodiments, the patient is about to start a cancer treatment or is being treated with the cancer treatment. While not wishing to be bound by theory, increased TRPV4 expression or cell signaling in TECs can normalized TECs' abnormal characteristics then can lead to the formation of blood vessels that are less hyperpermeable and les internal pressure. In one embodiment, the vascular leakage is reduced by at least 5% in the tumor compared to the leakage prior to administration of the TRPV4 agonist or vector. In another embodiment, the vascular leakage is reduced by at least 5% in the tumor compared to a control reference. In some embodiments, the vascular leakage is reduced by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 99%, or at least 100% prior to administration of the TRPV4 agonist or vector, or compared to the control reference, including all the percentages to the second decimal places between 5-100%. Methods of assessing vascular permeability are known to those ordinary skilled in the art. For example, using a hyperpolarized $^1$H-MRI, known as Overhauser enhanced MRI (OMRI) and an oxygen-sensitive contrast agent OX63 as described in Matsumotoa S. et al., (PNAS, 2009, 106: 17898-17903), by DCE-MRI or by using FITC dextran and multiphoton fluorescence intravital microscopy as described in Reyes-Aldasoro, C. C., et al. (Angiogenesis, 2006, 9:26), by $^{14}$C-iodoantipyrine (IAP)-quantitative autoradiography (QAR) (IAP-QAR) as described in Ewing J R, et al., (J. Cereb. Blood Flow Metab. 2003, 23:198-209) and by Evans blue dye extrusion as described by van der Heyde, H. C. et al. (Infection & Immunity, 2001, 69: 3460-3465).

In another embodiment, provided herein is a method for enhancing radiosensitivity to radiation therapy in a patient in need thereof, the method comprises administering a TRPV4 agonist or a vector comprising a DNA sequence encoding TRPV4 to the patient concurrently with a cancer treatment or subsequently administering the cancer treatment to the patient. In one embodiment, the method comprises contacting the tumor with a TRPV4 agonist or a vector comprising a DNA sequence encoding TRPV4. For example, directly injecting the TRPV4 agonist or the vector into the tumor in the patient. In one embodiment, the patient is diagnosed with cancer. In other embodiments, the patient is about to start a cancer treatment or is being treated with the cancer treatment. In one embodiment, the cancer treatment is radiation therapy. In one embodiment, the radiosensitivity of a tumor of the same type to radiation therapy is enhanced by at least 5% compared to the radiosensitivity of the tumor prior to administration of the TRPV4 agonist or vector. In one embodiment, the radiosensitivity of a tumor to radiation therapy is enhanced by at least 5% compared to a control reference. In one embodiment, the control reference is the average data of radiosensitivity of tumors from a control population of patients not administration of the TRPV4 agonist or vector. In some embodiments, the radiosensitivity is enhanced by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 99%, or at least 100% prior to administration of the TRPV4 agonist or vector, or compared to a control reference, including all the percentages to the second decimal places between 5-100%. Radiosensitivity of tumors can be assessed by any method known in the art. e.g., by assessing the amount of cell death before and after radiation therapy.

The inventors previously isolated TECs from prostrate adenocarinoma, studied various characteristics and responses of these TECs and shown that the TECs were very different from non-tumor derived, normal endothelial cells. TECs exhibited defective strain-induced reorientation of the cell main axis and actin cytoskeleton, exhibited abnormal mechano sensitivity to substrate elasticity compared to nECs by way of enhanced ability to spread to any given substrate elasticity, exhibited enhanced readiness to form capillary networks in vitro when plated at low cell density but not at high cell density, exhibited multicellular retraction, cell clumping and no capillary network formation in vitro when plated at very high cell density, and also exerted stronger Rho-mediated traction on their extracellular matrix adhesions (Ghosh et al., 2008, PNAS, 105:11305-11310). In response to uniaxial cyclic strain, nECs would re-orientate the cell main axis and actin cytoskeleton perpendicular to the direction of the strain (Iba and Sumpio, 1991, Microvasc. Res. 42:245-254; Ghosh et al., 2008, PNAS, 105:11305-11310). In contrast, under uniaxial cyclic strain, the TECs do not re-orientate the cell main axis and actin cytoskeleton perpendicular to the direction of the strain. This failure can be as much as 40% of the time.

Figure 1:
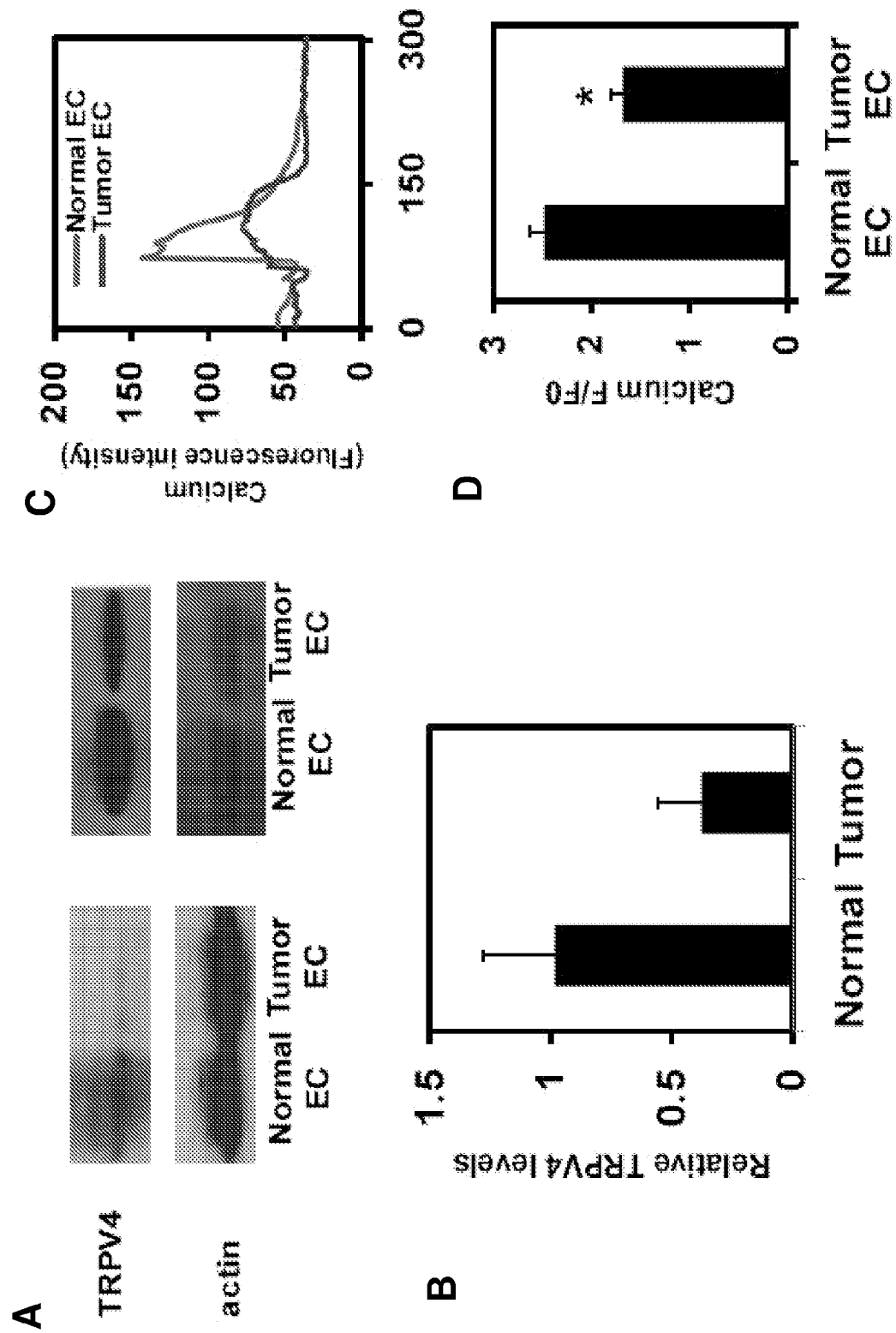
FIG. 1A shows Western blots demonstrating the reduced level of TRPV4 expression in tumor endothelial cells (TECs) compared to normal, non-cancer, non-tumor derived endothelial cells (nECs).
FIG. 1B is a histogram showing the relative levels of TRPV4 expressed in TECs compared to nECs.
FIG. 1C shows the fluorescence tracing of calcium ion influx into TECs compared to nECs in response to a TRPV4 specific activator, 4-a-PDD.
FIG. 1D is a histogram showing the quantitative analysis of the calcium influxes shown in FIG. 1C in TECs compared to normal ECs.
Figure 2:
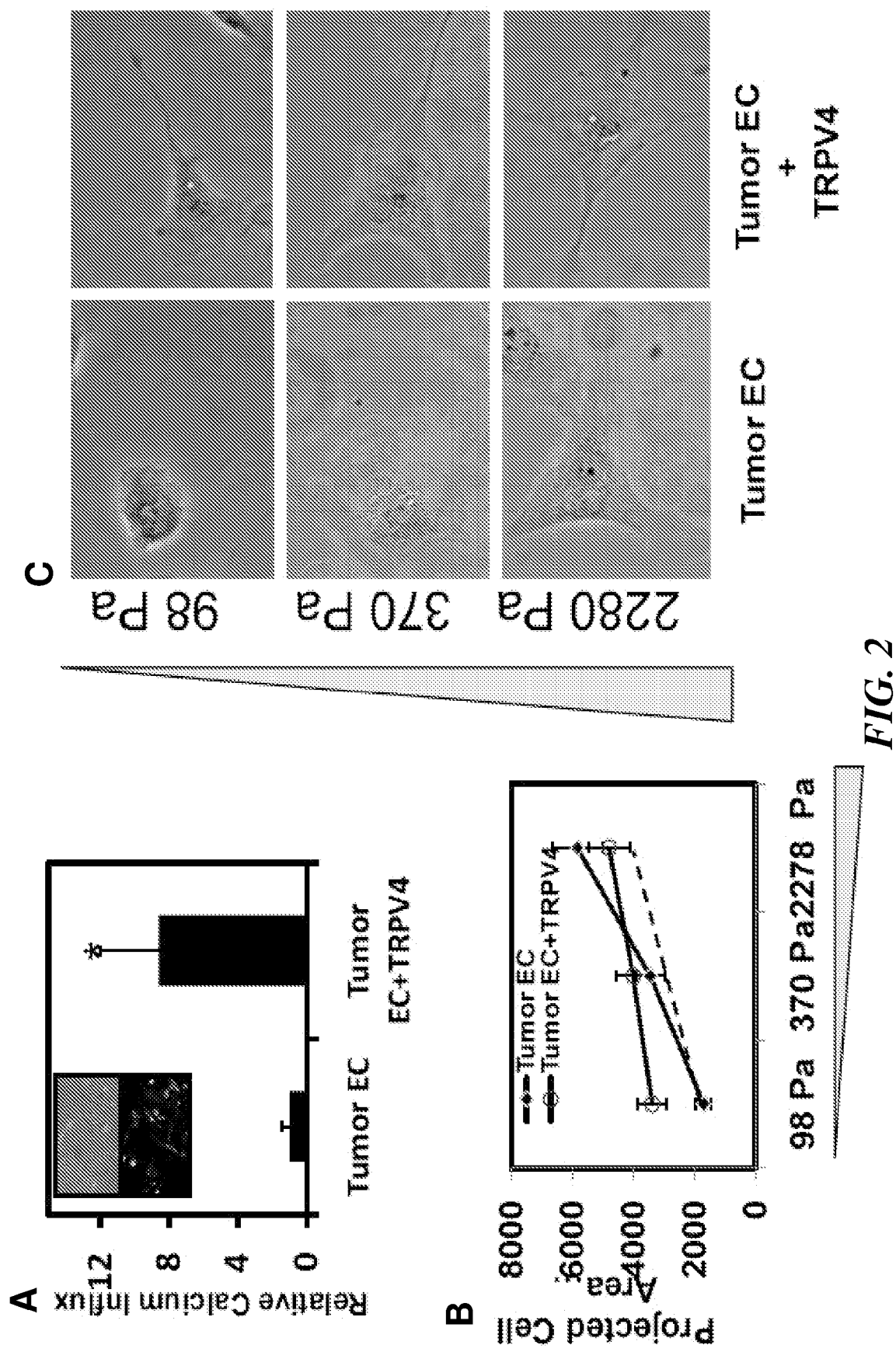
FIG. 2A is a histogram showing the relative calcium ion influx into control TECs compared to NECs expressing TRPV4 from an exogenous DNA sequence encoding TRPV4. Exogenous expression of TRPV4 increases calcium ion influx in the tumor ECs. Control tumor ECs do not expressing TRPV4 from an exogenous DNA sequence encoding TRPV4.
FIG. 2B is a graph showing the projected cell spread area for control TECs in response to external tension stress compared to TECs expressing TRPV4 from an exogenous DNA sequence encoding TRPV4. Exogenous expression of TRPV4 normalizes the responses to external tension stress in the tumor ECs. The dotted line shows the projected cell spread area for normal EC (nEC).
FIG. 2C contain phase contrast micrographs showing the cell spread of control a TEC responding to external tension stress compared to the response of a TEC expressing TRPV4 from an exogenous DNA sequence encoding TRPV4. Exogenous expression of TRPV4 normalizes the responses to external tension stress in the tumor ECs.
Figure 3:
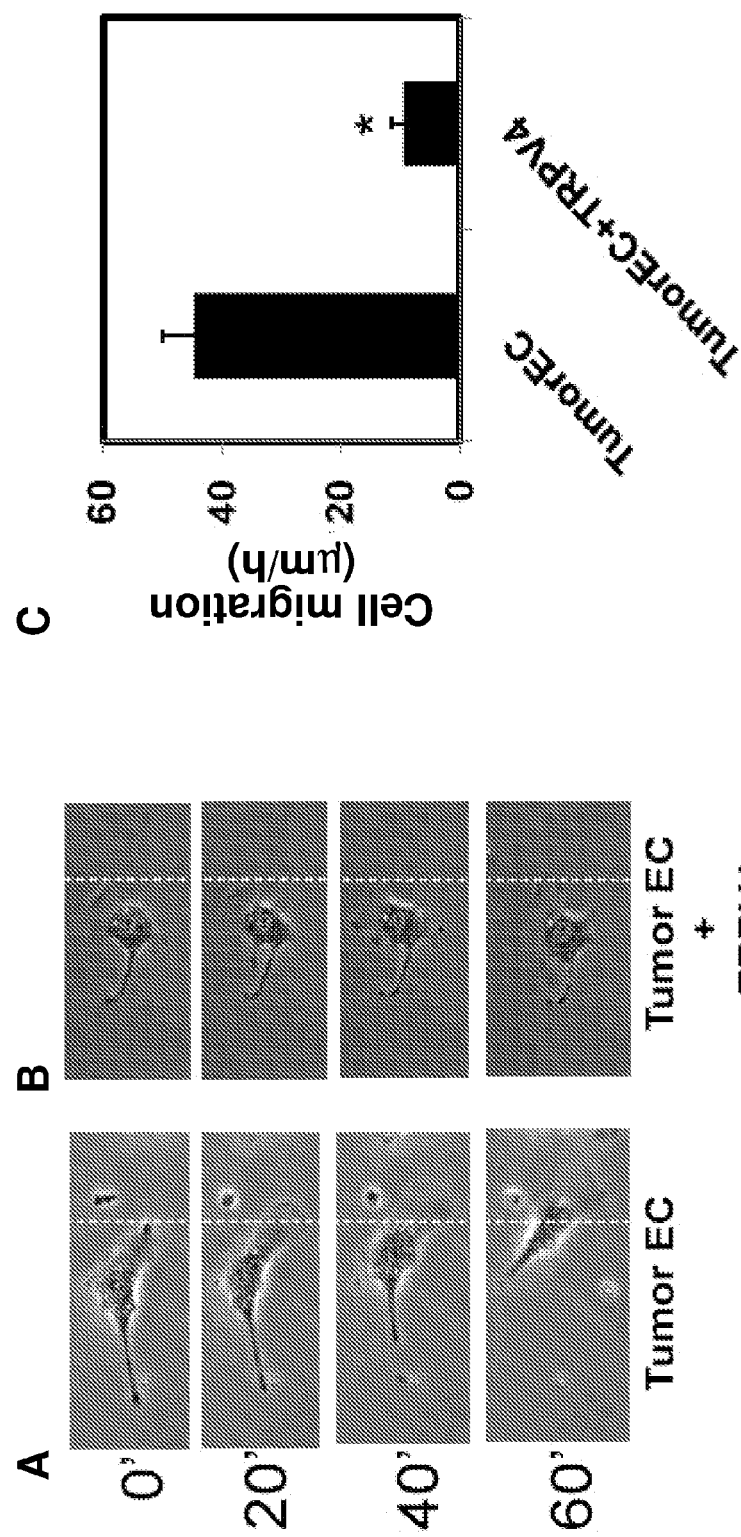
FIG. 3A shows time lapse phase contrast micrographs of a migrating control TEC showing leading edge and trailing end of the cell. Control tumor ECs do not expressing TRPV4 from an exogenous DNA sequence encoding TRPV4.
FIG. 3B shows time lapse phase contrast micrographs of a migrating TEC expressing TRPV4 from an exogenous DNA sequence encoding TRPV4. The migrating cell shows leading edge and trailing end of the cell.
FIG. 3C is a histogram showing the cell migration rates of control TECs compared to TECs expressing TRPV4 from an exogenous DNA sequence encoding TRPV4. Exogenous expression of TRPV4 reduces the cell migration rate in the TECs.
Figure 4:
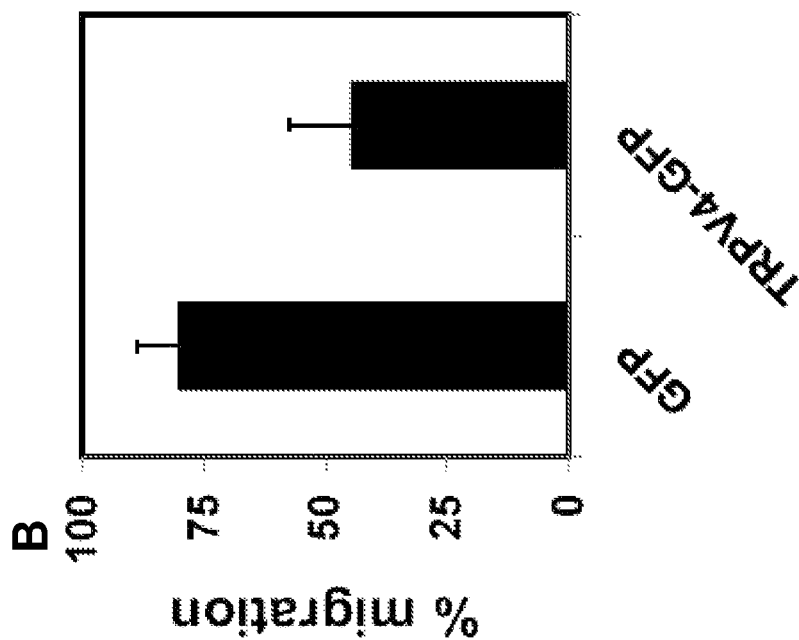
FIG. 4A contain phase contrast micrographs of migrating TECs expressing GFP (control) compared to TECs expressing TRPV4-EGFP from an exogenous DNA sequence encoding TRPV4 in a scratch assay.
FIG. 4B is a histogram showing the percent cell migration into the scratch zone by TECs expressing GFP (control) compared to TECs expressing TRPV4-EGFP from an exogenous DNA sequence encoding TRPV4. Exogenous expression of TRPV4 reduces the percent migration in the tumor ECs into the scratch zone.
Figure 4:
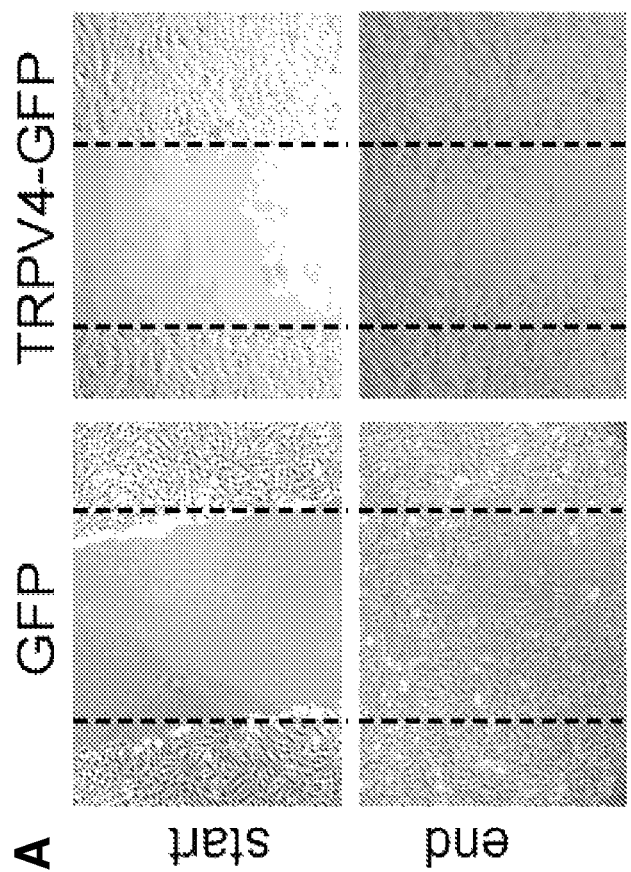
Figure 5:
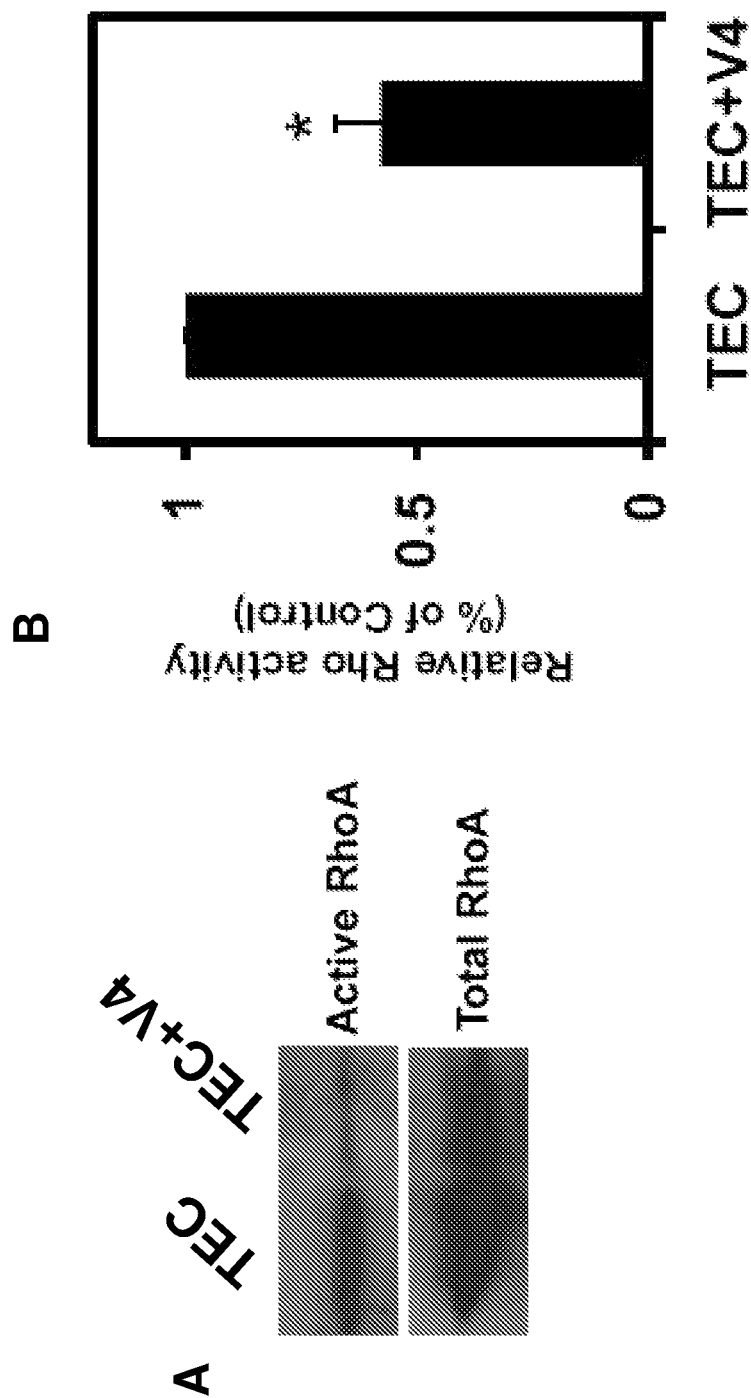
FIG. 5A shows Western blots demonstrating the reduced level of active Rho in TECs expressing TRPV4-EGFP from an exogenous DNA sequence encoding TRPV4 (TEC+V4) compared to control TECs that are not transfected with the exogenous DNA sequence.
FIG. 5B is a histogram showing the relative levels of Rho activity in TECs expressing TRPV4-EGFP from an exogenous DNA sequence encoding TRPV4 (TEC+V4) compared to control TECs that were not transfected with the exogenous DNA sequence.
Figure 6:
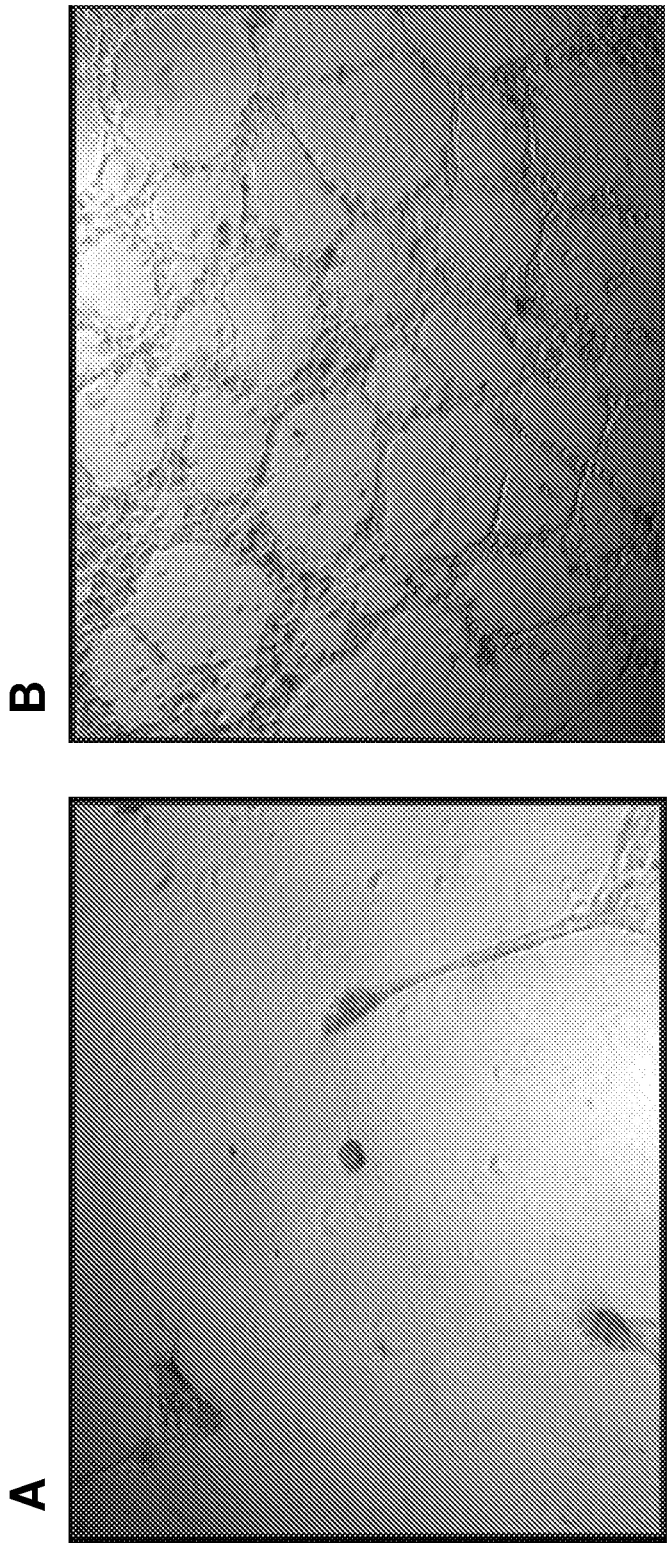
FIG. 6A is a phase contrast micrograph showing control TECs form multicellular cluster aggregation in an angiogenesis assay on MATRIGEL™. The control TECs were not transfected with an exogenous DNA sequence encoding TRPV4-EGFP.
FIG. 6B is a phase contrast micrograph of showing normalization of tube formation by the overexpression of TRPV4 in TECs in an angiogenesis assay on MATRIGEL™.

Recently, the inventors discovered that TECs had reduced levels of TRPV4 expression and reduced calcium influx upon TRPV4 stimulation compared to nECs (FIG. 1). The TRPV4 expression level in TECs was reduced by 10% to 75% (FIG. 1B). The calcium influx was reduced by 10% to 50% (FIG. 1C). More interestingly, the inventors discovered that by increasing TRPV4 expression in the TECs, the abnormal characteristic were reduced, normalized and/or restored to be closer to that of nECs. For example, TRPV4 expression restored the abnormal mechanosensitivity to substrate elasticity, inhibited the enhanced rate of cell migration (FIG. 3), e.g., in a scratch wound assay (FIG. 4), inhibited the abnormal basal Rho activity (FIG. 5), and promoted capillary networks formation in vitro instead of multicellular retraction and cell clumping when the TECs were plated at very high cell density in an in vitro angiogenesis assay (FIG. 6). For example, the TECs migration rate was reduced by as much as 90% compared to control TECs that did not exhibit increased TRPV4 expression (FIG. 3C). The abnormal basal Rho activity was reduced by about 60% compared to control TECs that did not exhibit increased TRPV4 expression (FIG. 5A).

This discovery that increasing TRPV4 expression in the TECs inhibited abnormal angiogenesis and normalizes angiogenesis by these TECs in vitro was surprising. This is because previously TRPV4 was identified as an important contributor to the ability of normal endothelial cells to sense and respond to mechanical stress that is necessary for the formation of new blood vessels (see WO 2009/149239). TRPV4 is a major mechanochemical "transducer" of mechanical strain in nEC. TRPV4 transduces the strain into a chemical signal intracellularly through the activation of β1 integrin, a transmembrane protein receptor that links the cytoskeleton to the extracellular matrix. It is known that mechanical strains influence the re-arrangement of the cells' cytoskeleton which in turn affects the migration capability of normal EC that is needed for re-aligning and/or reorienting the cells during angiogenesis. Therefore, inhibition of TRPV4 expression or the downstream cell signaling pathway is useful for inhibiting nEC cell alignment, nEC cell migration, capillary tube formation and overall angiogenesis (see WO 2009/149239). The discovery that increasing TRPV4 expression in the TECs inhibited abnormal angiogenesis is the exact opposite of the current teachings of TRPV4 in relationship to angiogenesis.

In one embodiment of the described methods, the control reference is the data obtained for a control population of patients all having the same type of cancer and were being treated or would be treated with the same anti-cancer therapy but were not administered with a TRPV4 agonist or a vector comprising a DNA sequence encoding TRPV4 concurrently or subsequently with the cancer treatment. In other words, the control population of patients was cancer type-matched and anti-cancer therapy-matched with the patient treated with TRPV4 agonist or vector.

In one embodiment of the described methods, the data is the average data obtained in assessing cancer treatment efficacy for patients that were not administered with a TRPV4 agonist or a vector comprising a DNA sequence encoding TRPV4. Methods of assessing cancer treatment efficacy are well known in the art to a skilled clinician, physician or oncologist. For example, assessing the shrinkage in size and reduction in the number of tumors by imaging by computed tomography (CT) scans, magnetic resonance imaging (MRI), positron emission tomography (PET), and ultrasound scans, measurement of the level of biomarkers that are known to be associated with the type of cancer (e.g. urinary N-terminal cross-linked type 1 collagen telopeptide (uNTx), C-terminal cross-linked type 1 collagen telopeptide (CTX), Alpha-fetoprotein (AFP), beta-human chorionic gonadotropin (β-HCG), beta2 (β2)-microglobulin), calcitonin, carbohydrate antigen 125 (CA-125), carbohydrate antigen 19-9 (CA 19-9), Carbohydrate antigen 27.29 (CA27.29), rcinoembryonic antigen (CEA), lactate dehydrogenase, prostate-specific antigen (PSA), and thyroglobulin), quantitative measurement of metabolically active tumor by determining the metabolic unit volume (MUV) by FDG PET/CT imagery (Jethya C, et al., J Nucl Med. 2008; 49 (Supplement 1):121P), laser-correlation spectrometry (LCS) of blood plasma and serum for malignant neoplasms (Akleyev et al., Proc. SPIE, 5973:597302 (2005)), and assessing skeletal-related event (SRE), pain scores, analgesic consumption, and quality of life (QoL) scores (Clemons M., et al., The Oncologist 2006 11: 227-233).

In one embodiment of the described methods, the data is the average level of TRPV4 expression in TECs from the control population of patients that are not administered a vector comprising a DNA sequence encoding a TRPV4. The level of TRPV4 expression can be measured by methods well known in the art, for example, quantitative reverse transcription polymerase chain reaction (qRT-PCR) with specific primers or by measuring the amount of the protein TRPV4, e.g., Western blot analysis. Exemplary primer pair for qRT-PCT of the human TRPV4 transcript is the forward primer GACGGGGACCTATAGCATCA (SEQ. ID. NO. 1) and the reverse primer AACAGGTCCAGGAGGAAGGT (SEQ. ID. NO. 2). Exemplary commercially available TRPV4 antibodies of Western blot analysis are catalog No: ab62992 from ABCAM, catalog No: AB9334-50UL and catalog No: AB9336-200UL from Millipore, and catalog No: LS-C95115 and catalog No: LS-C95200 from Lifespan Bioscience Inc.

In one embodiment of the described methods, the data of the control population is the average increase in calcium influx in the TEC of patients that were not administered a TRPV4 agonist. In this embodiment, the cell signaling is measured by an increase in calcium influx in the TECs of a patient administered a TRPV4 agonist compared to the TECs of a patient not administered a TRPV4 agonist. Methods of monitoring calcium in cell are well known in the art. For example, by flow cytometry (June, C. H., et al., Current Protocols in Cytometry, unit 9.8, 2001) and by fluorescence Spectroscopy of calcium sensitive dyes, e.g., Fura-2, Indo-1 oregon green bapta-1, Fluo-4 and Fluo-3. Alternatively, commercially available Fluo-4 Direct™ Calcium Assay Kit by INVITROGEN™ and The Wash free Fluo-8 Calcium Assay kits by HD Biosciences Co., Ltd can be used.

An exemplary method of measurement of intracellular calcium influx is provided as follows. TECs were isolated from tumor biopsy from patients that were administered with a TRPV4 agonist and from patients (control) not given a TRPV4 agonist. The TECs were mixed in culture with Fura-2 AM, rinse of free Fura-2 AM and then transferred to a quartz cuvette and the fluorescence measured at excitation wavelengths of 340 and 380 nm and an emission wavelength of 510 nm (LS50B Luminescence Spectrometer; Perkin Elmer, Buckinghamshire, UK). During the fluorescence measurements the cells were maintained in suspension using a magnetic stirrer and the cuvette was thermostatically controlled at 37° C. The ratio of the fluorescence values at excitation wavelengths of 340 and 380 nm were calibrated and converted to $Ca^{2+}$ concentration (nM) according to the protocol of Grynkiewicz et al. (J Biol Chem 1985; 260: 3440-3450) as follows.

$$[Ca^{2+}]_c = \frac{Kd(R - R\text{min})}{(R\text{max} - R)}$$

Kd is 224 nM, the apparent dissociation constant for $Ca^{2+}$ and Fura-2. The maximum ratio (Rmax) was obtained by the addition of Triton X-100 (0.5%) to lyse the cells. The minimum ratio (Rmin) was obtained by the addition of EGTA (7 mM, added as a 0.5 M stock buffered with 3M tris-hydroxymethyl-amino methase (Tris)-HCl).

In one embodiment of the described methods, the data of the control population is the average characteristics and responses of non-tumor or non-cancer associated endothelial cells. In some embodiments, the characteristics and responses of the endothelial cells are measured in terms of basal level of Rho activity, the rate of cell migration in vitro, and/or the mechanosensory and orientation response to external mechanic stimuli. In one embodiment, the data of the control population is the average basal level of Rho activity in a population of nEC. In another embodiment, the data of the control population is the average rate of cell migration in vitro for a population of nECs. In another embodiment, the data of the control population is the average mechanosensory and orientation responses to external mechanic stimuli for a population of nECs. In one embodiment, the nECs are obtained from patients administered with a TRPV4 agonist or a vector comprising a DNA sequence encoding TRPV4. In another embodiment, the nECs are obtained from patients that are not administered with a TRPV4 agonist or a vector comprising a DNA sequence encoding TRPV4.

Methods of assessing and measuring basal level of Rho activity, the rate of cell migration in vitro, and the mechanosensory and orientation response of endothelial cells are known to one skilled in the art. For example, Western blot analysis for active or GTP-bound Rho using anti-Rho antibody specific for the active or GTP-bound Rho, pull down of active Rho by RhoA G17A agarose beads from Cell Biolabs, Inc or with Rhotekin-RBD bisding assay as described in Ghosh et al., 2008, PNAS, 105:11305-11310 and Ren X. et al., 1999, EMBO J. 18:578-585, visual assessment of cell migration using a Boyden Chamber, visual assessment of cell migration using the scratch assay, the Oris™ Cell Migration Assay by Platypus Technologies, alternative cell migration assays described in Valster A., et al., (Methods 2005, 37:208-215), and mechanical strain application and imaging of response as described in Ghosh et al. supra. Alternatively, commercially kits are available for assessing Rho activity, cell migration and cell responses, e.g., Active Rho pull down and detection kits, catalog No: 89854 from Thermo Scientific Pierce, Cell Migration Fluorometric (CyQuant) Assay Kit, QCM™, Cell Migration Fluorometric (green) Assay Kit, InnoCyte™, Endothelial Cell Migration Colorimetric Assay Kit, and Endothelial Cell Migration Fluorometric Assay Kit by EMD Millipore, Cell Migration Universal Assembly Kit, Oris™ by Platypus Technologies and Endothelial cell (migration) Transmigration Kit and Planar Migration Assay Kit from Promocell GmbH.

In one embodiment, the data of the control population is the average radiosensitivity of tumors from patients not administration of the TRPV4 agonist or vector. Methods of assessing tumor radiosensitivity are known to those skilled in the art, e.g., physician, oncologist etc. For example, tumor radiosensitivity can be monitored by metabolic functional imaging using positron emission tomography (PET) as described in Belkacémi Y., et al. (Crit Rev Oncol Hematol. 2007, 62:227-39), by assessing amount of cell death, by using an in vitro a soft agar clonogenic assay of biopsy sample to a single dose of 2 Gy radiation (SF2) as described in Wilson C R., et al. (British J. Cancer, 200083:1702-1706) or by short-term proliferative assays such as [3(4,5-dimethylthiazol-2-yl)-2,5-diphenyltetrazolium bromide (MTT) reduction, methylene blue staining, and [3H]-thymidine incorporation] as described in Peter Cross M.D. et al. (Radiation Oncology Investigations, 1993, 1:261-269).

In one embodiment, the number of patients in the control population can range from 5-2000. In one embodiment, the patients in the control population also have the same stage of cancer, i.e. they are cancer stage-matched with the TRPV4 agonist or a vector treated patient. In one embodiment, the patients in the control population are also aged-matched within an age range, i.e. they are age-matched with the TRPV4 agonist or a vector treated patient. In one embodiment, the patients in the control population are gender-matched. Therefore, they are of the same gender as the TRPV4 agonist or a vector treated patient. In one embodiment, the patients in the control population are also race-matched, e.g., Caucasians, African, Hispanic, Asian etc, i.e. the patients in the control population are of the same or similar race as the TRPV4 agonist or a vector treated patient.

In one embodiment of the methods described, the method further comprises selecting a patient who has been diagnosed with cancer. As used herein, "cancer" refers to any of various malignant neoplasms characterized by the proliferation of anaplastic cells that tend to invade surrounding tissue and metastasize to new body sites and also refers to the pathological condition characterized by such malignant neoplastic growths.

In one embodiment of the methods described, the patient is diagnosed with cancer. Methods of diagnosing cancer are known to a skilled physician. In general, cancer is suspected based on a person's symptoms, the results of a physical examination, and the results of screening tests such as imaging. Imaging tests often include plain x-rays, ultrasonography, CT, and MRI. These tests assist in identifying abnormalities, determining qualities of a mass (solid or cystic), providing dimensions, and establishing relationship to surrounding structures, which can be important if surgery or biopsy is being considered. Occasionally, x-rays obtained for other reasons such as an injury, show abnormalities that might be cancer. Confirmation that cancer is present requires other tests (termed diagnostic tests e.g, by tumor biopsy and histopathologic examination). Other screening tests include but are not limited to screening the level of serum tumor markers the findings of which are suggestive of a specific cancer. For examples α-Fetoprotein (hepatocellular carcinoma, testicular carcinoma), carcinoembryonic antigen (colon cancer), β-human chorionic gonadotropin (choriocarcinoma, testicular carcinoma), serum immunoglobulins (multiple myeloma), DNA probes (eg, bcr probe to identify a chromosome 22 alteration in chronic myelogenous leukemia), CA 125 (ovarian cancer), CA 27-29 (breast cancer), prostate-specific antigen (prostate cancer).

After cancer is diagnosed, it is staged. Staging is a way of describing how extensive or advanced the cancer is in terms of its location, size, growth into nearby structures, and spread to other parts of the body. People with cancer sometimes become impatient and anxious during staging tests, wishing for a prompt start of treatment. However, staging allows doctors to determine the most appropriate treatment as well as helping to determine prognosis.

Staging may use scans or other imaging tests, such as x-ray, CT, MRI, bone scintigraphy, or positron emission tomography (PET). The choice of staging test(s) depends on the type of cancer, as different cancers involve different parts of the body. CT scanning is used to detect cancer in many parts of the body, including the brain and lungs and parts of the abdomen, including the adrenal glands, lymph nodes, liver, and spleen. MRI is of particular value in detecting cancers of the brain, bone, and spinal cord.

Biopsies are often needed for staging and can sometimes be done together with the initial surgical treatment of a cancer.

For example, during a laparotomy (an abdominal operation) to remove colon cancer, a surgeon removes nearby lymph nodes to check for spread of the cancer. During surgery for breast cancer, the surgeon biopsies or removes lymph nodes located in the armpit to determine whether the breast cancer has spread there; this information along with features of the primary tumor helps the doctor determine whether further treatment is needed. When staging is based only on initial biopsy results, physical examination, and imaging, the stage is referred to as clinical. When the doctor uses results of a surgical procedure or additional biopsies, the stage is referred to as pathologic. The clinical and pathologic stage may differ.

In addition to imaging tests, doctors often obtain blood tests to see if the cancer has begun to affect the liver, bone, or kidneys.

In one embodiment of the methods described, the cancer for the methods described herein include but are not limited to carcinomas and sarcomas found in the anus, bladder, bile duct, bone, brain, breast, cervix, colon/rectum, endometrium, esophagus, eye, gallbladder, head and neck, liver, kidney, larynx, lung, mediastinum (chest), mouth, ovaries, pancreas, penis, prostate, skin, small intestine, stomach, spinal marrow, tailbone, testicles, thyroid and uterus. The types of carcinomas include but are not limited to papilloma/carcinoma, choriocarcinoma, endodermal sinus tumor, teratoma, adenoma/adenocarcinoma, melanoma, fibroma, lipoma, leiomyoma, rhabdomyoma, mesothelioma, angioma, osteoma, chondroma, glioma, lymphoma/leukemia, squamous cell carcinoma, small cell carcinoma, large cell undifferentiated carcinomas, basal cell carcinoma and sinonasal undifferentiated carcinoma. The types of sarcomas include but are not limited to, for example, soft tissue sarcoma such as alveolar soft part sarcoma, angiosarcoma, dermatofibrosarcoma, desmoid tumor, desmoplastic small round cell tumor, extraskeletal chondrosarcoma, extraskeletal osteosarcoma, fibrosarcoma, hemangiopericytoma, hemangiosarcoma, Kaposi's sarcoma, leiomyosarcoma, liposarcoma, lymphangiosarcoma, lymphosarcoma, malignant fibrous histiocytoma, neurofibrosarcoma, rhabdomyosarcoma, synovial sarcoma, and Askin's tumor, Ewing's sarcoma (primitive neuroectodermal tumor), malignant hemangioendothelioma, malignant schwannoma, osteosarcoma, and chondrosarcoma.

In one embodiment of the methods described, the cancer treatment is chemotherapy. Chemotherapy treatment uses medicine to weaken and destroy cancer cells in the body, including cells at the original cancer site and any cancer cells that may have spread to another part of the body. Chemotherapy can also aims at keeping the cells from further multiplying. The majority of chemotherapeutic drugs can be divided in to alkylating agents, antimetabolites, anthracyclines, plant alkaloids, topoisomerase inhibitors, and other antitumour agents. All of these drugs affect cell division or DNA synthesis and function in some way. Examples of chemotherapeutic agents include but are not limited to drugs such as daunorubicin, daunomycin, dactinomycin, doxorubicin, epirubicin, idarubicin, esorubicin, bleomycin, mafosfamide, ifosfamide, epirubicin, cytosine arabinoside, bis-chloroethylnitrosurea, busulfan, mitomycin C, actinomycin D, mithramycin, prednisone, hydroxyprogesterone, testosterone, tamoxifen, dacarbazine, procarbazine, hexamethylmelamine, pentamethylmelamine, mitoxantrone, amsacrine, chlorambucil, methylcyclohexylnitrosurea, nitrogen mustards, melphalan, cyclophosphamide, 6-mercaptopurine, 6-thioguanine, cytarabine, 5-azacytidine, hydroxyurea, deoxycoformycin, 4-hydroxyperoxycyclophosphoramide, 5-fluorouracil (5-FU), 5-fluorodeoxyuridine (5-FUdR), methotrexate (MTX), colchicine, taxol, vincristine, vinblastine, etoposide (VP-16), trimetrexate, irinotecan, topotecan, gemcitabine, teniposide, cisplatin and diethylstilbestrol (DES).

In one embodiment of the methods described, the cancer treatment is immunotherapy. The principle behind cancer immunotherapy is to use of the immune system to reject cancer. Since the immune system responds to the environmental factors it encounters on the basis of discrimination between self and non-self, many kinds of tumor cells that arise as a result of the onset of cancer are more or less tolerated by the patient's own immune system since the tumor cells are essentially the patient's own cells that are growing, dividing and spreading without proper regulatory control. The main premise is stimulating the patient's immune system to attack the malignant tumor cells that are responsible for the disease. This can be either through immunization of the patient (e.g., by administering a cancer vaccine, such as Dendreon's Provenge), in which case the patient's own immune system is trained to recognize tumor cells as targets to be destroyed, or through the administration of therapeutic antibodies as drugs, in which case the patient's immune system is recruited to destroy tumor cells by the therapeutic antibodies.

In some embodiments, cancer immunotherapy includes but not limited to cell-based immunotherapy, monoclonal antibody therapy, and radioimmunotherapy.

In one embodiment of the methods described, the cancer treatment is cell based immunotherapy. In another embodiment of the methods described, the cancer treatment is autologous immune enhancement therapy (AIET). Cell based immunotherapy is a major form of cancer immunotherapy. This involves immune cells such as the natural killer cells (NK cells), lymphokine activated killer cell (LAK), cytotoxic T lymphocytes (CTLs), dendritic Cells (DC) etc which are either activated in vivo by administering certain cytokines such as interleukins or they are isolated, enriched and transfused to the patient to fight against cancer. Cell based immunotherapy encompasses AIET which involves isolation of either allogenic or autologous immune cells, enriching them outside the body and transfusing them back to the patient. The injected immune cells are highly cytotoxic to the cancer cells thereby helping to fight the cancer cells. AIET therapy is in routine clinical practice in some countries such as Japan.

In one embodiment of the methods described, the cancer treatment is monoclonal antibody therapy. Monoclonal antibody therapy involves raising antibodies against specific antigens such as the unusual antigens that are presented on the surfaces of tumors. Many kinds of tumor cells display unusual antigens that are either inappropriate for the cell type and/or its environment, or are only normally present during the organisms' development (e.g., fetal antigens). Examples of such antigens include the glycosphingolipid GD2, a disialoganglioside that is normally only expressed at a significant level on the outer surface membranes of neuronal cells, where its exposure to the immune system is limited by the blood-brain barrier. GD2 is expressed on the surfaces of a wide range of tumor cells including neuroblastoma, medulloblastomas, astrocytomas, melanomas, small-cell lung cancer, osteosarcomas and other soft tissue sarcomas. GD2 is thus a convenient tumor-specific target for immunotherapies. Other cancer antigens include but are not limited to CD52 for chronic lymphocytic leukemia, vascular endothelial growth factor for colorectal cancer, epidermal growth factor receptor for colorectal cancer, CD33 for acute myelogenous leukemia, CD20 for non-Hodgkin lymphoma, and ErbB2 for breast cancer. Anti-cancer monoclonal antibodies include but are not limited to alemtuzumab, bevacizumab, cetuximab, gemtuzumab ozogamicin, rituximab and trastuzumab.

In one embodiment of the methods described, the cancer treatment is radioimmunotherapy. Radioimmunotherapy involves the use of radioactively conjugated murine antibodies against cellular antigens, especially the cell surface antigens that are expressed unusually described herein, e.g., over expression, inappropriate expression temporarily and spacially. Some kinds of tumor cells display cell surface receptors that are rare or absent on the surfaces of healthy cells, and which are responsible for activating cellular signal transduction pathways that cause the unregulated growth and division of the tumor cell. Examples include ErbB2, a constitutively active cell surface receptor that is produced at abnormally high levels on the surface of breast cancer tumor cells. Most radioimmunotherapy currently involved their application to lymphomas, as these are highly radio-sensitive malignancies. To limit radiation exposure, murine antibodies were especially chosen, as their high immunogenicity promotes rapid clearance from the body. The two most common are ibritumomab tiuxetan and the tositumomab/iodine ($^{131}$I) tositumomab regimen. Ibritumomab tiuxetan is a murine antibody chemically linked to a chelating agent which binds yttrium-90. $^{90}$Y is a beta radiator, has a half-life of 64 h and a tissue penetration of 1-5 millimetres. Its use has been investigated, primarily in the treatment of follicular lymphoma. Tositumomab is a murine IgG2a anti-CD20 antibody. Iodine ($^{131}$I) tositumomab is covalently bound to Iodine 131. $^{131}$I emits both beta and gamma radiation, and is broken down rapidly in the body. Tositumomab and iodine ($^{131}$I) tositumomab are used in patients with relapsed follicular lymphoma.

In one embodiment of the methods described, the cancer treatment is radiation. Radiation therapy uses high-energy radiation to shrink tumors and kill cancer cells. The high-energy radiation kills cancer cells by damaging their DNA such that the cancer cells cannot multiply. X-rays, gamma rays, and charged particles are types of radiation used for cancer treatment. The radiation may be delivered by a machine outside the body (external-beam radiation therapy), or it may come from radioactive material placed in the body near cancer cells (internal radiation therapy, also called brachytherapy). Systemic radiation therapy uses radioactive substances, such as radioactive iodine, that travel in the blood to kill cancer cells, e.g., thyroid cancer. Image-guided radiation is a recent development in radiation therapy where it provides real-time imaging of the tumor target during treatment. Real-time imaging could help compensate for normal movement of the internal organs from breathing and for changes in tumor size during treatment.

In some embodiments of the methods described, the radiation is applied in conjunction with radiosensitizers and radioprotectors, chemicals that modify a cell's response to radiation. Radiosensitizers are drugs that make cancer cells more sensitive to the effects of radiation therapy. Several agents are under study as radiosensitizers. In addition, some anticancer drugs, such as 5-fluorouracil and cisplatin, make cancer cells more sensitive to radiation therapy. Radioprotectors (also called radioprotectants) are drugs that protect normal cells from damage caused by radiation therapy. These drugs promote the repair of normal cells exposed to radiation. Many agents are currently being studied as potential radioprotectors.

In one embodiment of the methods described, the cancer treatment is a combination of chemotherapy, immunotherapy and/or radiation therapy. In another embodiment, the cancer treatment includes radiosensitizers and/or radioprotectors In one embodiment of the methods described, the TRPV4 agonist is selected from a group consisting of GSK1016790A, Bisandrographolide A (BAA), RN 1747, AB1644034, α-phorbol 12,13-didecanoate (4αPDD) 5,6-EET, acetylcholine and App441-1. BAA is the active compound from the extracts of *Andrographis paniculata* (Chinese herbal plant).

In one embodiment of the methods described, the TRPV4 is a human TRPV4. TRPV4 is a member of the TRP channels comprising a large family of cation channels that provide a pathway for calcium influx into cells. Among the ~30 TRP-channel proteins identified in mammals, endothelial cells express ~20 members that are classified into six subfamilies: canonical (TRPC), vanilloid (TRPV), melastatin (TRPVM), polycystin (TRPP), mucolipin (TRPML) and TRPA. Structurally, TRP channels consist of six transmembrane (TM)-spanning helices with a pore region between TM5 and cytoplasmic N and C termini. Both TRPC and TRPV channels contain multiple anykyrin domains at their N-terminus that are absent in TRPM channels. Most of the TRP channels contain PDZ binding motifs and recognition sites for PKC and PI3K. TRPC subfamily channels that are ubiquitously expressed in endothelial cells are responsible for store-operated or receptor-mediated calcium entry; they also have been implicated in control of endothelial barrier function and vasorelaxation. Among the vertebrate TRPV and TRPM channels, TRPV4 and TRPV2 are considered mechanosensitive, and growing evidence suggests that TRPV4 plays critical role in mechanical force-induced regulation of endothelial cell function. For example, in endothelial cells, TRPV4 acts as a calcium entry channel that is activated by increases in cell volume and temperature. TRPV4 can also be activated by ligands such as arachidonic acid and its metabolites, endocannabinoids and a synthetic phorbol ester, 4-α-phorbol 12,13-didecanoate (PPD), and it can be suppressed by integrin and Src kinase inhibitors during osmotransduction in dorsal root ganglia.

The human TRPV4 gene is located on chromosome 12, location: 12q24.1, 108,705,277-108,755,595 reverse strand (ENSG00000111199) (Ensembl) assembled in Accession No. NC_000012.10 (SEQ. ID. No. 2; GENBANK™) Alternate gene names are OTRPC4, TRP12, VR-OAC, VRL-2, VRL2 and VROAC. This gene encodes a member of the OSM9-like transient receptor potential channel (OTRPC) subfamily in the transient receptor potential (TRP) superfamily of ion channels. The encoded protein is a $Ca^{2+}$-permeable, nonselective cation channel that is thought to be involved in the regulation of systemic osmotic pressure. Two transcript variants encoding different isoforms have been found for this gene. Two transcripts of TRPV4 from this gene are NM_021625.3 (SEQ. ID. No. 4) and NM_147204.1 (SEQ. ID. No. 5) (GENBANK™).

In one embodiment of the methods described, the DNA sequence that encodes a TRPV4 comprises SEQ. ID. NO. 4 or 5, the two messenger transcript variants of the human TRPV4. In another embodiment of the methods described, the DNA sequence that encodes a TRPV4 consists essentially of SEQ. ID. NO. 4 or 5, the two messenger transcript variants of the human TRPV4. In another embodiment of the methods described, the DNA sequence that encodes a TRPV4 consists of SEQ. ID. NO. 4 or 5, the two messenger transcript variants of the human TRPV4.

In one embodiment of the methods described, the DNA sequence that encodes a TRPV4 comprises the genomic sequence 108,705,277-108,755,595 reverse strand on chromosome 12, location: 12q24.1 (SEQ. ID. No. 2). In another embodiment of the methods described, the DNA sequence that encodes a TRPV4 consisting essentially of SEQ. ID. No. 2. In another embodiment of the methods described, the DNA sequence that encodes a TRPV4 consists essentially of SEQ.

ID. No. 2. In another embodiment of the methods described, the DNA sequence that encodes a TRPV4 consists of SEQ. ID. No. 2.

In one embodiment of the methods described, the DNA sequence that encodes a TRPV4 is in a vector. In one embodiment, the vector is an expression vector for the purpose of expressing a DNA sequence encoding a protein in a cell. In one embodiment, the vector is an inducible vector, such as a tetracycline inducible vector. Methods described, for example, in Wang et al. Proc. Natl. Acad. Sci. 100: 5103-5106, using pTet-On vectors (BD Biosciences Clontech, Palo Alto, Calif.) can be used. In some embodiments, a vector is a plasmid vector, a viral vector, or any other suitable vehicle adapted for the insertion and foreign sequence and for the introduction into eukaryotic cells. The vector can be an expression vector capable of directing the transcription of the DNA sequence enroding TRPV4.

In one embodiment, the expression vector is a viral vector. Viral expression vectors can be selected from a group comprising, for example, reteroviruses, lentiviruses, Epstein Barr virus-, bovine papilloma virus, adenovirus- and adeno-associated-based vectors or hybrid virus of any of the above. In one embodiment, the vector is episomal. The use of a suitable episomal vector provides a means of maintaining the antagonist nucleic acid molecule in the subject in high copy number extra chromosomal DNA thereby eliminating potential effects of chromosomal integration.

Any methods known in the art can be for constructing a vector for the purpose of expressing a DNA sequence encoding a TRPV4 in a cell. For example, conventional polymerase chain reaction (PCR) cloning techniques can be used to clone the DNA sequence encoding a TRPV4. A DNA sequence encoding a TRPV4 can be initially cloned into a general purpose cloning vector such as pUC19, pBR322, pBluescript vectors (STRATAGENE® Inc.) or pCR TOPO® from INVITROGEN™ Inc. prior to cloning into the expression vector.

Each PCR primer should have at least 15 nucleotides overlapping with its corresponding templates at the region to be amplified. The polymerase used in the PCR amplification should have high fidelity such as STRATAGENE®'s PFUULTRA™ polymerase for reducing sequence mistakes during the PCR amplification process. For ease of ligating several separate PCR fragments together, for example in the construction of a genomic DNA sequence encoding TRPV4 such as SEQ. ID. NO: 2, and subsequently inserting into a cloning vector, the PCR primers should also have distinct and unique restriction digestion sites on their flanking ends that do not anneal to the DNA template during PCR amplification. The choice of the restriction digestion sites for each pair of specific primers should be such that the DNA sequence encoding a TRPV4 is in-frame and will encode the predicted TRPV4 protein from beginning to end with no stop codons.

In gene therapy, a vector comprising a DNA sequence encoding a TRPV4 includes but is not limited to adenovirus, retrovirus, lentivirus, adeno associated virus, envelope protein pseudotype virus (chimeric virus), and virosomes (e.g. liposomes combined with an inactivated HIV or influenza virus).

A simplified system for generating recombinant adenoviruses is presented by He T C. et al. Proc. Natl. Acad. Sci. USA 95:2509-2514, 1998. The gene of interest is first cloned into a shuttle vector, e.g., pAdTrack-CMV. The resultant plasmid is linearized by digesting with restriction endonuclease Pme I, and subsequently cotransformed into E. coli. BJ5183 cells with an adenoviral backbone plasmid, e.g. pAdEasy-1 of STRATAGENE®'s AdEasy™ Adenoviral Vector System. Recombinant adenovirus vectors are selected for kanamycin resistance, and recombination confirmed by restriction endonuclease analyses. Finally, the linearized recombinant plasmid is transfected into adenovirus packaging cell lines, for example HEK 293 cells (E1-transformed human embryonic kidney cells) or 911 (E1-transformed human embryonic retinal cells) (Human Gene Therapy 7:215-222, 1996). Recombinant adenoviruses are generated within the HEK 293 cells.

Recombinant lentivirus has the advantage of delivery and expression of a TRPV4 in either dividing or non-dividing mammalian cells. The HIV-1 based lentivirus can effectively transduce a broader host range than the Moloney Leukemia Virus (MoMLV)-base retroviral systems. Preparation of the recombinant lentivirus can be achieved using the pLenti4/V5-DEST™, pLenti6/V5-DEST™ or pLenti vectors together with ViraPower™ Lentiviral Expression systems from INVITROGEN™.

An embodiment is the use of AAV viral vectors comprising nucleic acids encoding a TRPV4. Recombinant adeno-associated virus (rAAV) vectors are applicable to a wide range of host cells including many different human and non-human cell lines or tissues. Because AAV is non-pathogenic and does not ellicit an immune response, a multitude of pre-clinical studies have reported excellent safety profiles. rAAVs are capable of transducing a broad range of cell types and transduction is not dependent on active host cell division. High titers, >$10^8$ viral particle/ml, are easily obtained in the supernatant and 1011-1012 viral particle/ml with further concentration. The transgene is integrated into the host genome so expression is long term and stable.

The use of alternative AAV serotypes other than AAV-2 (Davidson et al (2000), PNAS 97:3428-32; Passini et al (2003), J. Virol 77:7034-40) has demonstrated different cell tropisms and increased transduction capabilities. With respect to brain cancers, the development of novel injection techniques into the brain, specifically convection enhanced delivery (CED; Bobo et al (1994), PNAS 91:2076-80; Nguyen et al (2001), Neuroreport 12:1961-4), has significantly enhanced the ability to transduce large areas of the brain with an AAV vector.

Large scale preparation of AAV vectors is made by a three-plasmid cotransfection of a packaging cell line: AAV vector carrying the coding nucleic acid, AAV RC vector containing AAV rep and cap genes, and adenovirus helper plasmid pDF6, into 50×150 mm plates of sub-confluent 293 cells. Cells are harvested three days after transfection, and viruses are released by three freeze-thaw cycles or by sonication.

AAV vectors are then purified by two different methods depending on the serotype of the vector. AAV2 vector is purified by the single-step gravity-flow column purification method based on its affinity for heparin (Auricchio, A., et. al., 2001, Human Gene therapy 12:71-6; Summerford, C. and R. Samulski, 1998, J. Virol. 72:1438-45; Summerford, C. and R. Samulski, 1999, Nat. Med. 5: 587-88). AAV2/1 and AAV2/5 vectors are currently purified by three sequential CsCl gradients.

Formulation and Administration

In one embodiment of the methods described, the method comprises administering a composition comprising a TRPV4 agonist or a vector comprising a DNA sequence encoding a TRPV4 and a pharmaceutically acceptable carrier.

In one embodiment, the composition further comprises a polymer. In one embodiment, the polymer comprises block co-polymers.

In one embodiment of the composition, the polymer forms nanoparticles.

In another embodiment, the composition further comprises a targeting agent. For example, to target the TRPV4 agonist or vector comprising a DNA sequence encoding a TRPV4 to the cancer site is a targeted delivery vehicle, e.g., a liposome, microparticle or nanoparticle. Specially targeted delivery vehicles can function to increase effective levels of the TRPV4 agonist or vector comprising a DNA sequence encoding a TRPV4 for tumor cells while reducing effective levels for other cells. This should result in an increased tumor kill and/or reduced toxicity. In general, specially targeted delivery vehicles have a differentially higher affinity for tumor cells by interacting with tumor-specific or tumor-associated antigens.

Specially targeted delivery vehicles vary in their stability, selectivity, and choice of target, but, in essence, they all aim to increase the maximum effective dose that can be delivered to the tumor cells. Reduced systemic toxicity means that they can also be used in sicker patients, and that they can carry new chemotherapeutic agents that would have been far too toxic to deliver via traditional systemic approaches.

In one embodiment, the targeting agent enhances accumulation of the composition or components within in a solid tumor. The TRPV4 agonist, vector comprising a DNA sequence encoding a TRPV4 or composition comprising there of can be targeted to specific organ or tissue by means of a targeting moiety, such as e.g., an antibody or targeted liposome technology. In some embodiments, targeting to tissue- or tumor-specific targets is by using bispecific antibodies, for example produced by chemical linkage of an anti-ligand antibody (Ab) and an Ab directed toward a specific target. To avoid the limitations of chemical conjugates, molecular conjugates of antibodies can be used for production of recombinant bispecific single-chain Abs directing ligands and/or chimeric inhibitors at cell surface molecules. The conjugation of the TRPV4 agonist, vector comprising a DNA sequence encoding a TRPV4 or composition comprising thereof permits the TRPV4 agonist or vector comprising a DNA sequence encoding a TRPV4 to attached and to accumulate additively at the desired target site. Antibody-based or non-antibody-based targeting moieties can be employed to deliver the TRPV4 agonist or vector comprising a DNA sequence encoding a TRPV4 to a target site. Preferably, a natural binding agent for an unregulated or disease associated antigen is used for this purpose. For example, Albumin is playing an increasing role as a drug carrier in the clinical setting. This is because there is substantial accumulation of albumin in solid tumors and this fact forms the rationale for developing albumin-based drug delivery systems for tumor targeting. A methotrexate-albumin conjugate, an albumin-binding prodrug of doxorubicin, i.e. the (6-maleimido)caproylhydrazone derivative of doxorubicin (DOXO-EMCH), and an albumin paclitaxel nanoparticle (Abraxane) have been evaluated clinically. Abraxane has been approved for treating metastatic breast cancer. Albuferon, a fusion protein of albumin and interferon is currently being assessed. (Kratz F. J., Control Release. 2008, 18:132(3):171-83). Partly PEGylated polyamidoamine (PAMAM) dendrimers were used as the carrier for tumor-selective targeting of the anticancer drug doxorubicin (DOX). Acid-sensitive cis-aconityl linkage or acid-insensitive succinic linkage was introduced between DOX and polymeric carriers to produce PPCD or PPSD conjugates, respectively. DOX release from PPCD conjugates followed an acid-triggered manner and increased with increasing PEGylation degree. In vitro cytotoxicity of PPCD conjugates against murine B16 melanoma cells increased with, while cellular uptake decreased with increasing PEGylation degree. (Zhu S. et al, Biomaterials, 2010, 31:1360-71).

In some embodiments, the targeting agent is covalently or non-covalently linked to the polymer. In another embodiment, the targeting agent is covalently or non-covalently linked to the TRPV4 agonist or vector. Methods of linking are well known in the art, e.g., a bi-functional linker described in WO 2007/034479, Mei H., et al., Biomaterials. 2010, 31:5619-26, Hu K, en al., J Control Release. 2009, 134:55-61, Chen Z., et al., J Drug Target. 2010 Nov. 23; and Santosh Aryal, ACS Nano, 2010, 4:251-258.

In one embodiment, the composition further comprises a cancer therapeutic agent. In one embodiment of the composition, the cancer therapeutic agent is for chemotherapy, radiotherapy or immunotherapy.

In one embodiment of the methods described, the TRPV4 agonist or the vector comprising a DNA sequence encoding a TRPV4 is delivered with or in a pharmaceutically acceptable carrier.

In one embodiment, the term "pharmaceutically acceptable" means approved by a regulatory agency of the Federal or a state government or listed in the U.S. Pharmacopeia or other generally recognized pharmacopeia for use in animals, and more particularly in humans. Specifically, it refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations, and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in Remington's Pharmaceutical Sciences, 18th Ed., Gennaro, ed. (Mack Publishing Co., 1990). The formulation should suit the mode of administration. Additional carrier agents, such as liposomes, can be added to the pharmaceutically acceptable carrier.

As used herein, the terms "administering," refers to the placement of a TRPV4 agonist, a vector comprising a DNA sequence encoding a TRPV4 or a composition comprising the TRPV4 agonist or the vector comprising a DNA sequence encoding a TRPV4 into a patient by a method or route which results in at least partial localization of the TRPV4 at a desired site. The TRPV4 agonist, vector comprising a DNA sequence encoding a TRPV4 or composition can be administered by any appropriate route which results in an effective treatment in the patient.

As used herein, the term "comprising" or "comprises" is used in reference to methods, and respective component(s) thereof, that are essential to the invention, yet open to the inclusion of unspecified elements, whether essential or not. The use of "comprising" indicates inclusion rather than limitation.

The term "consisting of" refers to methods, and respective components thereof as described herein, which are exclusive of any element not recited in that description of the embodiment.

Compositions that are therapeutic for the methods described herein contain a physiologically tolerable carrier together with an active agent as described herein, dissolved or dispersed therein as an active ingredient. The active ingredient is a TRPV4 agonist or a vector comprising a DNA sequence encoding a TRPV4. The active ingredient can include more that one TRPV4 agonist, e.g., a mixture of two, three, or up to five TRPV4 agonists. In a preferred embodiment, the therapeutic composition is not immunogenic when administered to a mammal or human patient for therapeutic purposes. As used herein, the terms "pharmaceutically acceptable", "physiologically tolerable" and grammatical variations thereof, as they refer to compositions, carriers, diluents and reagents, are used interchangeably and represent that the materials are capable of administration to or upon a mammal without the production of undesirable physiological effects such as nausea, dizziness, gastric upset and the like. A pharmaceutically acceptable carrier will not promote the raising of an immune response to an agent with which it is admixed, unless so desired. The preparation of a pharmacological composition that contains active ingredients dissolved or dispersed therein is well understood in the art and need not be limited based on formulation. Typically such compositions are prepared as injectable either as liquid solutions or suspensions, however, solid forms suitable for solution, or suspensions, in liquid prior to use can also be prepared. The preparation can also be emulsified or presented as a liposome composition. The active ingredient can be mixed with excipients which are pharmaceutically acceptable and compatible with the active ingredient and in amounts suitable for use in the methods described herein. Specifically contemplated pharmaceutical compositions include those comprising a TRPV4 agonist or a vector comprising a DNA sequence encoding a TRPV4 in a preparation for delivery as described herein above, or in references cited and incorporated herein in that section. Suitable excipients include, for example, water, saline, dextrose, glycerol, ethanol or the like and combinations thereof. In addition, if desired, the composition can contain minor amounts of auxiliary substances such as wetting or emulsifying agents, pH buffering agents and the like which enhance the effectiveness of the active ingredient. The therapeutic composition for the methods described herein can include pharmaceutically acceptable salts of the components therein. Pharmaceutically acceptable salts include the acid addition salts (formed with the free amino groups of the polypeptide) that are formed with inorganic acids such as, for example, hydrochloric or phosphoric acids, or such organic acids as acetic, tartaric, mandelic and the like. Salts formed with the free carboxyl groups can also be derived from inorganic bases such as, for example, sodium, potassium, ammonium, calcium or ferric hydroxides, and such organic bases as isopropylamine, trimethylamine, 2-ethylamino ethanol, histidine, procaine and the like. Physiologically tolerable carriers are well known in the art. Exemplary liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, polyethylene glycol and other solutes. Liquid compositions can also contain liquid phases in addition to and to the exclusion of water. Exemplary of such additional liquid phases are glycerin, vegetable oils such as cottonseed oil, and water-oil emulsions. The amount of an active agent used in the methods described herein that will be effective in the treatment of a particular disorder or condition will depend on the nature of the disorder or condition, and can be determined by standard clinical techniques.

The method of delivering the composition comprising a TRPV4 agonist or a vector comprising a DNA sequence encoding a TRPV4 will vary based on the individual patient, the type and location of cancer being treated and other criteria evident to one of ordinary skill in the art. Delivery methods include direct injection at the treatment site, percutaneous delivery for injection, percutaneous delivery for topical application, and other delivery methods well known to persons of ordinary skill in the art.

Routes of administration include, but are not limited to, topical, transdermal, direct injection, intradermal, intramuscular, intraperitoneal, intravenous, subcutaneous, intranasal, epidural, and oral routes. Administration can be systemic or local.

Topical administration of a pharmacologically effective amount may utilize transdermal delivery systems well known in the art. An example is a dermal patch. Topical and transdermal delivery can be accomplished via a wound dressing impregnated with a TRPV4 agonist or a vector comprising a DNA sequence encoding a TRPV4 enter the dermis and also enter the blood stream. Alternatively the biolistic gene gun method of delivery may be used. The gene gun is a device for injecting cells with genetic information, originally designed for plant transformation. The payload is an elemental particle of a heavy metal coated with plasmid DNA. This technique is often simply referred to as biolistics. Another instrument that uses biolistics technology is the PDS-1000/He particle delivery system. The vector comprising a DNA sequence encoding a TRPV4 can be coated on minute gold particles, and these coated particles are "shot" into cancer tissues such as and melanoma under high pressure. An example of the gene gun-based method is described for DNA based vaccination of cattle by Loehr B. I. et al. J. Virol. 2000, 74:6077-86. Other direct injection delivery methods, including intramuscular, intracoronary and subcutaneous injections, can be accomplished using a needle and syringe, using a high pressure, needle free technique, like POWDERJECT™, constant infusion pump, a catheter delivery system, or the injection apparati disclosed in the International Patent Publication number WO 2007112136.

In addition to topical administration, the TRPV4 agonist, the vector comprising a DNA sequence encoding a TRPV4 or the composition comprising thereof described herein can also be administered systemically in a pharmaceutical formulation. For example, the TRPV4 agonist, the vector comprising a DNA sequence encoding a TRPV4 or the composition comprising thereof can be administered intravenously, e.g. via central venous catheter (CVC or central venous line or central venous access catheter) placed into a large vein in the neck (internal jugular vein), chest (subclavian vein) or groin (femoral vein).

Systemic routes include but are not limited to oral, parenteral, nasal inhalation, intratracheal, intrathecal, intracranial, and intrarectal. The pharmaceutical formulation is preferably a sterile saline or lactated Ringer's solution. For therapeutic applications, the preparations described herein are administered to a human, in a pharmaceutically acceptable dosage form, including those that may be administered to a human intravenously as a bolus or by continuous infusion over a period of time, by intramuscular, intraperitoneal, intracerebrospinal, subcutaneous, intra-arterial, intrasynovial, intrathecal, oral, topical, or inhalation routes. The TRPV4 agonist, the vector comprising a DNA sequence encoding a TRPV4 or the composition comprising thereof described herein are also suitably administered by intratumoral, peritumoral, intralesional or perilesional routes, to exert local as well as systemic effects. The intraperitoneal route is expected to be particularly useful, for example, in the treatment of ovarian tumors. For these uses, additional conventional pharmaceutical preparations such as tablets, granules, powders, capsules, and sprays may be preferentially required. In such formulations further conventional additives such as binding-agents, wetting agents, propellants, lubricants, and stabilizers may also be required. In one embodiment, the therapeutic compositions described herein are formulated in a cationic liposome formulation such as those described for intratracheal gene therapy treatment of early lung cancer (Zou Y. et. al., Cancer Gene Ther. 2000 May; 7(5):683-96). The liposome formulations are especially suitable for aerosol use in lung cancer patients. Vector DNA and/or virus can be entrapped in 'stabilized plasmid-lipid particles' (SPLP) containing the fusogenic lipid dioleoylphosphatidylethanolamine (DOPE), low levels (5-10 mol %) of cationic lipid, and stabilized by a polyethyleneglycol (PEG) coating (Zhang Y. P. et. al. Gene Ther. 1999, 6:1438-47). Other techniques in formulating expression vectors and virus as therapeutics are found in "DNA-Pharmaceuticals: Formulation and Delivery in Gene Therapy, DNA Vaccination and Immunotherapy" by Martin Schleef (Editor) December 2005, Wiley Publisher, and "Plasmids for Therapy and Vaccination" by Martin Schleef (Editor) May 2001, are incorporated herein as reference. In one embodiment, the dosage for viral vectors is $1 \times 10^6$ to $1 \times 10^{14}$ viral vector particles per application per patient.

The TRPV4 agonist, the vector comprising a DNA sequence encoding a TRPV4 or the composition comprising thereof can be formulated as a sustained-release composition of formulation. For example, sustained-release pharmaceutical compositions include, but are not limited to, sustained-release matrices such as biodegradable matrices or semipermeable polymer matrices in the form of shaped articles, e.g., films, or mirocapsules that comprise the TRPV4 agonist, the vector comprising a DNA sequence encoding a TRPV4 or the composition comprising thereof.

A sustained-release matrix, as used herein, is a matrix made of materials, usually polymers, which are degradable by enzymatic or acid/base hydrolysis or by dissolution. Once inserted into the body, the matrix is acted upon by enzymes and body fluids. The sustained-release matrix desirably is chosen from biocompatible materials such as liposomes, polylactides (polylactic acid), polyglycolide (polymer of glycolic acid), polylactide co-glycolide (co-polymers of lactic acid and glycolic acid)polyanhydrides, poly(ortho)esters, polyproteins, hyaluronic acid, collagen, chondroitin sulfate, carboxylic acids, fatty acids, phospholipids, polysaccharides, nucleic acids, polyamino acids, amino acids such as phenylalanine, tyrosine, isoleucine, polynucleotides, polyvinyl propylene, polyvinylpyrrolidone and silicone. A preferred biodegradable matrix is a matrix of one of polylactide, polyglycolide, or polylactide co-glycolide (co-polymers of lactic acid and glycolic acid).

Sustained-release matrices include polylactides (U.S. Pat. No. 3,773,919, EP 58,481), copolymers of L-glutamic acid and gamma-ethyl-L-glutamate (U. Sidman et al., Biopolymers 22:547-556 (1983)), poly(2-hydroxyethyl methacrylate) (R. Langer et al., J. Biomed Mater. Res. 15:167-277 (1981), and R. Langer, Chem. Tech. 12:98-105 (1982)), ethylene vinyl acetate (R. Langer et al., Id.) or poly-D-(−)-3-hydroxybutyric acid (EP 133,988). Sustained-release compositions also include liposomally entrapped the TRPV4 agonist, the vector comprising a DNA sequence encoding a TRPV4 or the composition comprising thereof. Such liposomes can be prepared by methods known per se: DE 3,218,121; Epstein, et al., Proc. Natl. Acad. Sci. USA 82:3688-3692 (1985); Hwang et al., Proc. Natl. Acad. Sci. USA 77:4030-4034 (1980); EP 52,322; EP 36,676; EP 88,046; EP 143,949; EP 142,641; Japanese Pat. Appl. 83-118008; U.S. Pat. Nos. 4,485,045 and 4,544,545; and EP 102,324. Ordinarily, the liposomes are of the small (about 200-800 Angstroms) unilamellar type in which the lipid content is greater than about 30 mol. percent cholesterol, the selected proportion being adjusted for the optimal therapy. Other biodegradable polymers and their use are described, for example, in detail in Brem et al. (1991, J. Neurosurg. 74:441-446).

For examples of sustained release compositions, see U.S. Pat. No. 3,773,919, EP 58,481A, U.S. Pat. No. 3,887,699, EP 158,277A, Canadian Patent No. 1176565, U. Sidman et al., Biopolymers 22:547 (1983) and R. Langer et al., Chem. Tech. 12:98 (1982). The TRPV4 agonist or the composition comprising thereof described herein will usually be formulated in such vehicles at a concentration of about 0.1 mg/ml to 100 mg/ml and the vector comprising a DNA sequence encoding a TRPV4 should be in the range of $1 \times 10^6$ to $1 \times 10^{14}$ viral vector particles per application per patient.

In one embodiment, osmotic minipumps are used to provide controlled sustained delivery of pharmaceutical compositions described herein, through cannulae to the site of interest, e.g. directly into a tissue at the site of metastatic growth or into the vascular supply of a tumor. The pump can be surgically implanted, for example continuous administration of endostatin, an anti-angiogenesis agent, by intraperitoneally implanted osmotic pump is described in Cancer Res. 2001 Oct. 15; 61(20):7669-74. Therapeutic amounts of the TRPV4 agonist, the vector comprising a DNA sequence encoding a TRPV4 or the composition comprising thereof can also be continually administered by an external pump attached to an intravenous needle.

For enteral administration, a composition can be incorporated into an inert carrier in discrete units such as capsules, cachets, tablets or lozenges, each containing a predetermined amount of the active compound; as a powder or granules; or a suspension or solution in an aqueous liquid or non-aqueous liquid, e.g., a syrup, an elixir, an emulsion or a draught. Suitable carriers may be starches or sugars and include lubricants, flavorings, binders, and other materials of the same nature.

A tablet may be made by compression or molding, optionally with one or more accessory ingredients. Compressed tablets may be prepared by compressing in a suitable machine the active compound in a free-flowing form, e.g., a powder or granules, optionally mixed with accessory ingredients, e.g., binders, lubricants, inert diluents, surface active or dispersing agents. Molded tablets may be made by molding in a suitable machine, a mixture of the powdered active compound with any suitable carrier.

A syrup or suspension may be made by adding the active compound to a concentrated, aqueous solution of a sugar, e.g., sucrose, to which may also be added any accessory ingredients. Such accessory ingredients may include flavoring, an agent to retard crystallization of the sugar or an agent to increase the solubility of any other ingredient, e.g., as a polyhydric alcohol, for example, glycerol or sorbitol.

Formulations for rectal administration may be presented as a suppository with a conventional carrier, e.g., cocoa butter or Witepsol S55 (trademark of Dynamite Nobel Chemical, Germany), for a suppository base.

Formulations for oral administration may be presented with an enhancer. Orally-acceptable absorption enhancers include surfactants such as sodium lauryl sulfate, palmitoyl carnitine, Laureth-9, phosphatidylcholine, cyclodextrin and derivatives thereof; bile salts such as sodium deoxycholate, sodium taurocholate, sodium glycochlate, and sodium fusidate; chelating agents including EDTA, citric acid and salicylates; and fatty acids (e.g., oleic acid, lauric acid, acylcarnitines, mono- and diglycerides). Other oral absorption enhancers include benzalkonium chloride, benzethonium chloride, CHAPS (3-(3-cholamidopropyl)-dimethylammonio-1-propanesulfonate), Big-CHAPS(N,N-bis(3-D-gluconamidopropyl)-cholamide), chlorobutanol, octoxynol-9, benzyl alcohol, phenols, cresols, and alkyl alcohols. An especially preferred oral absorption enhancer for the present invention is sodium lauryl sulfate.

Alternatively, the TRPV4 agonist, the vector comprising a DNA sequence encoding a TRPV4 or the composition comprising thereof can be administered in liposomes or microspheres (or microparticles). Methods for preparing liposomes and microspheres for administration to a patient are well known to those of skill in the art. U.S. Pat. No. 4,789,734, the contents of which are hereby incorporated by reference, describes methods for encapsulating biological materials in liposomes. A review of known methods is provided by G. Gregoriadis, Chapter 14, "Liposomes," Drug Carriers in Biology and Medicine, pp. 287-341 (Academic Press, 1979).

Microspheres formed of polymers or proteins are well known to those skilled in the art, and can be tailored for passage through the gastrointestinal tract directly into the blood stream. Alternatively, the compound can be incorporated in the microspheres, or composite of microspheres, implanted for slow release over a period of time ranging from days to months. See, for example, U.S. Pat. Nos. 4,906,474, 4,925,673 and 3,625,214, and Jein, TIPS 19:155-157 (1998), the contents of which are hereby incorporated by reference.

Preferred microparticles are those prepared from biodegradable polymers, such as polyglycolide, polylactide and copolymers thereof. Those of skill in the art can readily determine an appropriate carrier system depending on various factors, including the desired rate of drug release and the desired dosage.

In one embodiment, the formulations are administered via catheter directly to the inside of blood vessels. The administration can occur, for example, through holes in the catheter. The formulations comprising the TRPV4 agonist, the vector comprising a DNA sequence encoding a TRPV4 or the composition comprising thereof can be included in biodegradable polymeric hydrogels, such as those disclosed in U.S. Pat. No. 5,410,016 to Hubbell et al. These polymeric hydrogels can be delivered to the inside of a tissue lumen and the active compounds released over time as the polymer degrades. If desirable, the polymeric hydrogels can have microparticles or liposomes which include the active compound dispersed therein, providing another mechanism for the controlled release of the active compounds.

The precise dose and formulation to be employed depends upon the potency of the TRPV4 agonist or the vector comprising a DNA sequence encoding a TRPV4, and include amounts large enough to produce the desired effect, e.g., an increased cell signaling via the TRPV4 receptor and/or by an increased expression of TRPV4 in the tumor ECs. The dosage should not be so large as to cause unacceptable adverse side effects. Generally, the dosage will vary with the type of TRPV4 agonist or vector, and with the age, condition, and sex of the patient are also considered. Dosage and formulation of the TRPV4 agonist, the vector comprising a DNA sequence encoding a TRPV4 or the composition comprising thereof will also depend on the route of administration, and the type, stage, location of cancer, and should be decided according to the judgment of the practitioner and each patient's circumstances. Effective doses can be extrapolated from dose-response curves derived from in vitro or animal model test systems.

The dosage can be determined by one of skill in the art and can also be adjusted by the individual physician in the event of any complication. Typically, for the TRPV4 agonist, the dosage ranges from 0.001 mg/kg body weight to 5 g/kg body weight. In some embodiments, the dosage range is from 0.001 mg/kg body weight to 1 g/kg body weight, from 0.001 mg/kg body weight to 0.5 g/kg body weight, from 0.001 mg/kg body weight to 0.1 g/kg body weight, from 0.001 mg/kg body weight to 50 mg/kg body weight, from 0.001 mg/kg body weight to 25 mg/kg body weight, from 0.001 mg/kg body weight to 10 mg/kg body weight, from 0.001 mg/kg body weight to 5 mg/kg body weight, from 0.001 mg/kg body weight to 1 mg/kg body weight, from 0.001 mg/kg body weight to 0.1 mg/kg body weight, from 0.001 mg/kg body weight to 0.005 mg/kg body weight. Alternatively, in some embodiments the dosage range is from 0.1 g/kg body weight to 5 g/kg body weight, from 0.5 g/kg body weight to 5 g/kg body weight, from 1 g/kg body weight to 5 g/kg body weight, from 1.5 g/kg body weight to 5 g/kg body weight, from 2 g/kg body weight to 5 g/kg body weight, from 2.5 g/kg body weight to 5 g/kg body weight, from 3 g/kg body weight to 5 g/kg body weight, from 3.5 g/kg body weight to 5 g/kg body weight, from 4 g/kg body weight to 5 g/kg body weight, from 4.5 g/kg body weight to 5 g/kg body weight, from 4.8 g/kg body weight to 5 g/kg body weight. In one embodiment, the dose range is from 5 µg/kg body weight to 30 µg/kg body weight. Alternatively, the dose range will be titrated to maintain serum levels between 5 µg/mL and 30 µg/mL.

Administration of the doses recited above can be repeated for a limited period of time. In some embodiments, the doses are given once a day, or multiple times a day, for example but not limited to three times a day. In a preferred embodiment, the doses recited above are administered daily for several weeks or months. The duration of treatment depends upon the subject's clinical progress and responsiveness to therapy. Continuous, relatively low maintenance doses are contemplated after an initial higher therapeutic dose.

As exemplary, for the treatment of solid tumors that are accessible by catheters or needles, the TRPV4 agonist or the vector comprising a DNA sequence encoding a TRPV4 and a pharmaceutically acceptable carrier can be formulated for direct application by injection into the solid tumor and/or adjacent to the tumor site, e.g., melanoma. The TRPV4 agonist or the vector comprising a DNA sequence encoding a TRPV4 can also be formulated for a transdermal delivery, e.g. a skin patch. For cancers or tumors not so easily accessible, the TRPV4 agonist or the vector comprising a DNA sequence encoding a TRPV4 can be administered to one of the main blood vessel that drains the cancer site, e.g. into the hepatic portal vein for liver cancer.

Such dosage forms encompass pharmaceutically acceptable carriers that are inherently nontoxic and nontherapeutic.

Examples of such carriers include ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts, or electrolytes such as protamine sulfate, disodium hydrogen phosphate, potassium hydrogen phosphate, sodium chloride, zinc salts, colloidal silica, magnesium trisilicate, polyvinyl pyrrolidone, cellulose-based substances, and polyethylene glycol. Carriers for topical or gel-based forms of antibody include polysaccharides such as sodium carboxymethylcellulose or methylcellulose, polyvinylpyrrolidone, polyacrylates, polyoxyethylene-polyoxypropylene-block polymers, polyethylene glycol, and wood wax alcohols. For all administrations, conventional depot forms are suitably used. Such forms include, for example, microcapsules, nano-capsules, liposomes, plasters, inhalation forms, nose sprays, and sublingual tablets. The antibody will typically be formulated in such vehicles at a concentration of about 0.1 mg/ml to 100 mg/ml.

Efficacy testing can be performed during the course of treatment using the methods described herein. Measurements of the degree of severity of a number of symptoms associated with a particular ailment are noted prior to the start of a treatment and then at later specific time period after the start of the treatment. Other methods of efficacy testing include evaluating for rate of vessel growth, angiogenesis, etc.: (1) inhibiting, arresting, or slowing the pathogenic growth of abnormal blood vessels and irregular or abnormal angiogenesis, thickness of blood vessel, vessel leakage in tumors; or (2) reducing the tumor growth; and (3) preventing or reducing the angiogenesis in tumors).

Unless otherwise explained, all technical and scientific terms used herein have the same meaning as commonly understood by one of ordinary skill in the art to which this disclosure belongs. Definitions of common terms in molecular biology may be found in Benjamin Lewin, Genes IX, published by Jones & Bartlett Publishing, 2007 (ISBN-13: 9780763740634); Kendrew et al. (eds.), The Encyclopedia of Molecular Biology, published by Blackwell Science Ltd., 1994 (ISBN 0-632-02182-9); and Robert A. Meyers (ed.), Molecular Biology and Biotechnology: a Comprehensive Desk Reference, published by VCH Publishers, Inc., 1995 (ISBN 1-56081-569-8). Further, unless otherwise required by context, singular terms shall include pluralities and plural terms shall include the singular.

Unless otherwise stated, the present invention was performed using standard procedures known to one skilled in the art, for example, in Maniatis et al., Molecular Cloning: A Laboratory Manual, Cold Spring Harbor Laboratory Press, Cold Spring Harbor, N.Y., USA (1982); Sambrook et al., Molecular Cloning: A Laboratory Manual (2 ed.), Cold Spring Harbor Laboratory Press, Cold Spring Harbor, N.Y., USA (1989); Davis et al., Basic Methods in Molecular Biology, Elsevier Science Publishing, Inc., New York, USA (1986); Current Protocols in Molecular Biology (CPMB) (Fred M. Ausubel, et al. ed., John Wiley and Sons, Inc.), Current Protocols in Immunology (CPI) (John E. Coligan, et. al., ed. John Wiley and Sons, Inc.), Current Protocols in Cell Biology (CPCB) (Juan S. Bonifacino et. al. ed., John Wiley and Sons, Inc.), Culture of Animal Cells: A Manual of Basic Technique by R. Ian Freshney, Publisher: Wiley-Liss; 5th edition (2005), Animal Cell Culture Methods (Methods in Cell Biology, Vol. 57, Jennie P. Mather and David Barnes editors, Academic Press, 1st edition, 1998), Methods in Molecular biology, Vol. 180, Transgenesis Techniques by Alan R. Clark editor, second edition, 2002, Humana Press, and Methods in Meolcular Biology, Vo. 203, 2003, Transgenic Mouse, edited by Marten H. Hofker and Jan van Deursen, which are all herein incorporated by reference in their entireties.

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

Other than in the operating examples, or where otherwise indicated, all numbers expressing quantities of ingredients or reaction conditions used herein should be understood as modified in all instances by the term "about." The term "about" when used in connection with percentages will mean±1%.

All patents and publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The present invention can be defined in any of the following alphabetized paragraphs:

[A] A TRPV4 agonist or a vector comprising a DNA sequence encoding a TRVP4 for increasing the efficacy of an anti-cancer treatment in a patient in need thereof.

[B] A TRPV4 agonist or a vector comprising a DNA sequence encoding a TRVP4 for treatment of cancer in a patient in need thereof.

[C] The use of paragraph [A] or [B], wherein the TRPV4 agonist or a vector is administered concurrently with an anti-cancer treatment or the anti-cancer treatment is administered subsequently.

[D] The use of paragraph [A], [B] or [C], wherein the TRPV4 agonist is selected from a group consisting of GSK1016790A, Bisandrographolide A (BAA), RN 1747, AB1644034, α-phorbol 12,13-didecanoate (4αPDD) 5,6-EET, acetylcholine and App441-1.

[E] The use of paragraph [A], [B], [C] or [D], wherein the TRVP4 is a human TRVP4.

[F] The use of paragraph [E], wherein the human TRVP4 is SEQ. ID. NO. 3, 4 or 5.

[G] The use of any one of paragraphs [A]-[F], wherein the cancer treatment is chemotherapy, radiation therapy or immunotherapy.

[H] A method for increasing the efficacy of an anti-cancer treatment in a patient in need thereof, the method comprising administering a TRPV4 agonist or a vector comprising a DNA sequence encoding TRVP4 to the patient concurrently with a cancer treatment or subsequently administering the cancer treatment to the patient.

[I] A method for cancer treatment in a patient in need thereof, the method comprising administering a TRPV4 agonist or a vector comprising a DNA sequence encoding TRVP4 to the patient concurrently with a cancer treatment or subsequently administering the cancer treatment to the patient.

[J] The method of paragraph [H] or [I], wherein the cancer treatment is chemotherapy, radiation therapy or immunotherapy.

[K] The method of paragraph [H], [I] or [J], wherein the TRPV4 agonist is selected from a group consisting of GSK1016790A, Bisandrographolide A (BAA), RN 1747, AB1644034, α-phorbol 12,13-didecanoate (4αPDD) 5,6-EET, acetylcholine and App441-1

[L] The method of paragraph [H], [I], [J] or [K], wherein the TRVP4 is a human TRVP4.

[M] The method of paragraph [L], wherein the TRVP4 gene is SEQ. ID. NO. 3, 4 or 5.

This invention is further illustrated by the following example which should not be construed as limiting. The contents of all references cited throughout this application, as well as the figures and table are incorporated herein by reference.

Those skilled in the art will recognize, or be able to ascertain using not more than routine experimentation, many equivalents to the specific embodiments of the invention described herein. Such equivalents are intended to be encompassed by the following claims.

EXAMPLE

Materials and Methods

Cell Culture. Tumor endothelial cells (EC) cells were isolated from transgenic TRAMP mice bearing prostate adenocarcinoma. Because it is difficult to obtain sufficient quantities of EC cells from the normal mouse prostate (due to its small size), normal EC that were isolated from the dermis (MDEC cells) of TRAMP mice were used instead. Normal EC cells from human dermis (HDEC cells; Cambrex) and an established mouse pancreatic EC cell line (MS1-EC cells; gift of Judah Folkman) served as independent non-tumor EC cell controls. Tumor EC cells, MDEC, and MS1-EC cells were cultured on Fibronectin-coated tissue culture dishes and grown in culture medium composed of low glucose DMEM, 10% FBS, 10% Nu Serum IV, basic fibroblast growth factor (6 ng/ml), heparin salt (0.1 mg/ml), 1% insulin-transferrin-selenium, and an antibiotic/mycotic mixture. These cells were used between passages 10-19. HDEC cells were grown on tissue culture dishes in medium as per manufacturer's protocol and used between passages 4-8.

Mechanical Strain Application

EC cells cultured on fibronectin-coated 6 well UNI-FLEX™ (FLEXCELL® International) plates for 24 hours to 70-80% confluence and then were subjected to uniaxial cyclic stretch (10% elongation; 1 Hz frequency) for 18 h using a FLEXERCELL® TENSION PLUS™ System (FLEXCELL®International). In some experiments, the EC cells were plated on fibronectin-coated 6 well BIOFLEX® (FLEXCELL® International) for 1 h and subjected to static stretch (15% elongation) for 1-15 min. Control cells were maintained under identical conditions in the absence of strain application.

Calcium Imaging

EC cells adherent to the flexible substrates were loaded with Fluo-4/AM (1 µM) for 30 min, washed 3 times in calcium medium (136 mM NaCl, 4.7 mM KCl, 1.2 mM $MgSO_4$, 1.1 mM $CaCl_2$, 1.2 mM $KH_2PO4$, 5 mM $NaHCO_3$, 5.5 mM glucose, and 20 mM Hepes. pH 7.4) and then exposed to mechanical strain (15% elongation) for 3-4 sec using a Stage Flexer (FLEXCELL® International) apparatus that is fixed on a Nikon upright microscope equipped with CCD camera (Spot-RT slider, Diagnostics Corp, USA). Images were acquired for every 4 seconds and analyzed using IP lab software and Microsoft Excel as described in Matthews, et al. (2006) (J. Cell Sci., 119:508-518).

Modulation of ECM Elasticity

Transglutaminase-cross-linked gelatin hydrogels of increasing stiffness were prepared with a final gelatin concentration of 3, 5, or 10% (wt/vol) and incubated at 37° C. overnight to stabilize cross-linking Stiffness measurements were performed by using an AR-G2 rheometer (TA Instruments) with a standard aluminum parallel plate geometry of 20 mm. Hydrogels were subjected to a stress sweep, and their storage moduli (G') were compared under the same physical conditions. To analyze the effects of varying ECM elasticity on cell shape, we cultured EC cells for 6 h on hydrogels of varying stiffness at a low density (1,000 cells per squared centimeter) to minimize cell-cell interactions.

Morphological and Immunofluorescence Studies

Cells adherent to flexible ECM substrates and subjected to mechanical stretch were washed in PBS, fixed in 4% paraformaldehyde for 30 min either mounted on glass slides (for visualizing GFP-AKT-PH translocation) or permeabilized with 0.25% TRITON®-X100/PBS for 5 min for immuno staining. After blocking with DMEM containing 10% FBS, cells were incubated for 1 h with ALEXA®-phalloidin to visualize stress fibers, washed and mounted on glass slides using FLUOROMOUNT-G™ (Southern Biotech). Images were acquired on a LEICA® Confocal SP2 microscope and processed using LEICA® software and Adobe Photoshop.

EC cell reorientation in response to cyclic strain was measured by quantitating the angle of orientation of cells relative to the direction of applied strain using ImageJ software and MICROSOFT® EXCEL®. Cells on substrates exposed to uniaxial cyclic strain with their longest axis oriented between 60 and 120 degrees relative to the direction of the applied strain field were considered to be aligned. Statistical differences between experimental groups were determined using the student t-test.

Biochemical Analysis

Western blotting analyses were performed according to methods published in Mammoto et. al. (2007) (J. Cell Sci., 120:456-467). Membranes containing transferred protein were blocked in 3% BSA/TBST for 1 h and incubated overnight with primary antibodies against TRPV4 (1:1000) at 4° C. The membranes were subsequently washed incubated with HRP-conjugated secondary antibodies (1:5000) for 1 h and washed and incubated with SUPERSIGNAL® West Pico ECL reagent from Pierce Biotechnology Inc. (USA) and exposed to Kodak X-ray film (SIGMA ALDRICH®).

In Vitro Angiogenesis Assay

Capillary network formation by EC cells was analyzed by using a two-dimensional fibrin gel assay, which was modified from the well known fibrin-based in vitro assay. Thrombin-crosslinked fibrin gels (3 mg/ml) were formed in 48-well plates and incubated at 37° C. for 30 min before normal and tumor EC cells were plated in culture medium at densities of 2, 3, 4, or $8 \times 10^4$ cells per well. Cells were cultured at 37° C. for 24 h before tube formation was analyzed. In some experiments, cells plated at the highest density ($8 \times 10^4$ cells per well) and cultured for 3 h were treated with Y27632 (10 µM), and capillary network formation was monitored after 24 h. To analyze capillary organization by EC cells cultured within (as opposed to on top of) 3D ECM gels, normal or tumor EC cells were resuspended at a high density ($5 \times 10^6$ cells per milliliter) in either fibrin gel (5 mg/ml) or MATRIGEL™ and cultured the cells in regular growth medium for 1 day or 2 wk, respectively.

Cell Migration

Cell migration assay was performed using Transwell assay. Briefly, cells were plated on to gelatin coated (0.5%) transwell membranes (Coster) in EBM2 supplemented with 0.3% FBS and their migration in response to VEGF (10 ng/ml) was monitored. The migrated cells were stained with Giemsa solution for 16 h and ten random fields were counted. To measure in vitro angiogenesis, EC cells were plated on MATRIGEL™ (BD Biosciences) and incubated in the presence of VEGF (10 ng/ml) at 37° C. After 18 h, tube formation was assessed in ten random fields (Mamotto, 2009, Nature 457:1103-1109).

Analysis of Cellular Traction Forces

Traction forces exerted by EC cells on their ECM adhesions were measured by using traction force microscopy. Cells were grown on thin (~100 μm), FN-coated, flexible polyacrylamide gels (Young's modulus=14 kPa) containing fluorescent nanobeads (100 nm diameter) as fiduciary markers.

Rho Activation Assay

Rho activity was determined by using the Rhotekin-RBD binding assay (Cytoskeleton). Cells grown on FN-coated flexible silicone substrates with or without 10% uniaxial cyclic strain for 2 h were lysed in RIPA buffer, and equal volumes of clarified lysate were treated with GST-Rhotekin-RBD beads for 1 h at 4° C. The beads were pelleted, washed, and treated with SDS-sample buffer to solubilized bead-bound GTP-Rho, which was detected by using western blot analysis.

Microscopy, Image Analysis, and Statistics

Images of live cells forming tubular structures in the in vitro angiogenesis assay and of cells cultured on compliant gelatin hydrogels fixed with 4% paraformaldehyde were recorded by using a Nikon Diaphot 300 phase contrast microscope (Nikon) fitted with a Hamamatsu digital camera (Hamamatsu Photonics). In other studies, cells were fixed with 4% paraformaldehyde, permeabilized with 0.2% Triton X-100, stained with Alexa Fluor-488 Phalloidin and DAPI (to visualize actin and nuclei, respectively), and imaged by using an Nikon Eclipse TE 2000-E microscope (Nikon) fitted with a CoolSnap HQ digital camera (Photometrics). Image analyses were performed by using ImageJ software (National Institutes of Health). For cyclic strain experiments, computerized morphometric analysis of fluorescence images was carried out to determine the angle between the longest axis of the cell and the direction of applied cyclic strain; these results are reported as the percentage of cells aligned at 90o $^L$ 3Oo relative to the direction of the applied strain.

For cell spreading studies, projected cell areas were measured by tracing cell perimeters, and the areas were normalized to their respective mean values from the earliest time point or the most compliant substrate. For densitometric analyses of western blots, levels of GTP-Rho were expressed as a percentage of total Rho levels, and then normalized to baseline (control) GTP-Rho levels in normal CE cells. All data were obtained from multiple replica experiments and are expressed as mean±SEM. Statistical significance was determined by using Student's unpaired t test (InStat; GraphPad).

For reorientation and scratch experiments, imaging was performed on cells cultured on MatTek glass bottomed dishes on LEICA® Confocal Microscope T later Cells were imaged three days after strain or stretch.

Ex-Plant Tumor Growth in Wild Type Mice (WT) and TRPV4 Knockout Mice (KO)

Mouse lewis lung carcinoma (LLC) cells ($2 \times 10^6$) were subcutaneously injected into wild type C57BL6/J mice (WT) or TRPV4 knockout mice (KO) in C57BL6 background. At indicated days, the tumor growth was measured using calipers and TRPV4 expression was quantitated by RT-PCR. MDEC is a mouse endothelial cell line used as a positive control.

For immunohistochemical analysis showing increased microvessel density in LLC tumors after 21 days, frozen sections of tumors (10 mm thickness) were stained with CD31 (PECAM-1) to identify tumor micro vessels and DAPI to stain nuclei.

Results

Tumor EC Expresses Low Levels of TRPV4 Expression and Activity In Vitro and In Vivo The inventors have previously shown that endothelial cells isolated from prostate tumor exhibited aberrant mechanosensation and failed to align in response to cyclic strain in vitro (Ghosh et al., 2008, PNAS, 105:11305-11310). Since, cyclic strain-induced reorientation in endothelial cells is dependent on TRPV4 channels as TRPV4 knock down cells failed to reorient (Thodeti et al., 2009, Circ. Res. 104:1123-1130), the inventors measured TRPV4 levels in tumor endothelial cells (TEC) isolated from prostate tumor bearing mice. The inventors found two bands with a molecular weight of 90 KDa and 110 KDa corresponding to TRPV4 in Western blots from normal EC (nEC) which were significantly at lower levels in tumor EC (FIGS. 1A & 1B). To confirm whether this difference in TRPV4 expression affects TRPV4 function in these cells, the inventors measured calcium influx in Fluo-4 loaded cells in response to specific TRPV4 activator 4-α-PDD. The inventors found that 4-α-PDD induced a rapid robust calcium influx in nEC which was reduced almost 40% in tumor EC (FIGS. 1C and 1D). These results clearly demonstrated that TRPV4 expression and function is impaired in TEC.

TRPV4 Overexpression Restores Mechanosensitivity to Substrate Elasticity in Tumor EC Next, the inventors transfected TEC with a human TRPV4-EGFP construct and checked its ability to rescue aberrant mechanosensation of tumor EC. EGFP fluorescence revealed that more than 80% cells were transfected with TRPV4-EGFP by using the Amaxa nucleofection assay (FIG. 2A inset). TRPV4 activator, 4-α-PDD induced almost 8 fold increase in calcium in these cells compared to EGFP alone-transfected TEC (FIG. 2A). The inventors then cultured these TRPV4-overexpressing cells on transglutamase linked gelatin gels of various stiffness (98 to 2,280 Pa) for 6 h and compared their cell spreading over time with that of EGFP-transfected TEC (control). As expected and shown in FIGS. 2B and 2C, TEC cells transfected with only EGFP attached, spread and increases their degree of spreading with the increasing gel stiffness. They spread around 1,800 m$^2$ on the softest (98 Pa) gel and increased their spreading almost 2 times on gels with intermediate stiffness (370 Pa) and continued to increase their spreading on maximal (2,280 Pa) rigidity (FIGS. 2B and 2C) confirming their abnormal mechanosensitivity. In contrast, TEC cells transfected with TRPV4-EGFP exhibited optimal spreading on intermediate gel stiffness and reached a plateau on maximal rigid substrate similar to normal CE cells (Ghosh et al., 2008, PNAS, 105:11305-11310). Thus, overexpression of TRPV4 seems to normalize the abnormal or abberant mechanosensitivity (i.e., the requirement of stiffer substrates to achieve maximal shape stability) of TEC.

TRPV4 Over Expression Normalizes Abnormal Angiogenesis by Tumor EC Through the Modulation of Rho Activity and Cell Migration Since the high basal Rho activity and dependent contractility is the reason for abnormal mechanosensitivity of TEC (Ghosh, et al., 2008, PNAS, 105:11305-11310), the inventors measured Rho activation and migration of TEC. The inventors first asked if TRPV4 expression influence cell migration on gelatin substrates. For this, the inventors have chosen a substrate with intermediate stiffness that have been shown to support optimal cell spreading in both TEC (control) and TEC expressing TRPV4. Cells were cultured in the growth media were imaged and the random cell migration was calculated. In accordance with their abnormal mechanosensitivity, control TEC exhibited abnormal cell migration (40 μm/h) (FIGS. 3A and 3C). In contrast, TEC expressing TRPV4-EGFP migrated slowly on these substrates (FIGS. 3 B and 3C). Similarly, overexpression of TRPV4 also reduced migration of TEC in a scratch-wound assay. The inventors then measured Rho activity using Rhotekin pull down assays. The inventors found that TEC cells transfected with TRPV4-EGFP exhibited reduced basal Rho activity (almost 50%) compared to tumor CE cells that are expressing only EGFP (P<0.001) (FIG. 5.A and 5B) indicating that TRPV4 expression alone inhibited or reduced basal Rho activity in these cells. These data show that the TECs exhibited higher baseline Rho activity and mediated contractility/migration, all of which were reduced by expression of TRPV4.

Cell contractility and Rho activity are important mediators of angiogenesis. The inventors have recently shown that TEC which express high Rho activity and abnormal angiogenesis (Ghosh et al., 2008, PNAS, 105:11305-11310). Therefore, the inventors asked whether the over-expression of TRPV4 influences TEC ability to form capillary networks. TEC cells transfected with TRPV4-EGFP or EGFP alone were tested for their capacity to form capillary net works using a MATRI-GEL™ based in vitro angiogenesis assay. The inventors used a plating density of $8 \times 10^4$ cells (per well) that was shown to cause the TECs to undergo multicellular retraction that led to gradual disruption of the tubular network, eventually forming large cell clumps at the highest cell plating density (REF). As expected TEC transfected with only EGFP collapsed and failed to form tubular net work (FIG. 6A). In contrast, overexpression of TRPV4 in TEC normalized the abnormal angiogenesis as these cells reorganized and forms a robust multicellular capillary network (FIG. 6B).

To confirm a direct role of TRPV4 in tumor angiogenesis in vivo, the inventors induced tumors in TRPV4 knockout and wild type mice (C57BL6) by subcutaneously injecting the mouse Lewis lung carcinoma cells (LLC). the inventors found that the tumor growth was 2-3 times more in TRPV4-/- KO mice compared to the WT mice at 21 days (FIGS. 7A and 7B). Further, the inventors measured the tumor angiogenesis by staining the microvessels with an endothelial specific marker, PECAM-1. Immunohistochemical analysis revealed that the tumors from TRPV4 KO mice exhibited significantly increased microvessel density (PECAM-1 positive) compared to tumors from WT mice (FIG. 8). These results clearly show that TRPV4 plays a critical role in modulating angiogenesis and absence of TRPV4 can lead to abnormal tumor angiogenesis probably through altered mechanotransduction by TECs.

To further confirm that TRPV4 normalizes tumor angiogenesis in vivo, the inventors will induce tumors in wild type mice (C57BL6) by subcutaneously injecting the mouse Lewis lung carcinoma cells (LLC). After tumors reaching a growth of 150-200 mm$^3$, the inventors will give an intraperitonial injection of TRPV4 agonist (10 μg-3 mg/kg; this is a random number) for 2-4 days followed by chemotherapeutic drugs such as Cisplatin (3 mg/kg/week). Tumor growth will be monitored every 3 days throughout the study. The mice will be sacrificed at the end of 3 weeks and angiogenesis will be assessed by measuring microvascular density either by immunostaining with PECAM-1 antibodies or Alexa-conjugated isolectin. The tumors in the TRPV4 agonist treated mice will have a reduced growth compared to placebo treated mice (control).

The references cited herein and throughout the specification are incorporated herein by reference.

What is claimed is:

1. A method for increasing the efficacy of an anti-cancer treatment in a patient in need thereof, the method comprising administering a TRPV4 agonist or a vector comprising a DNA sequence encoding a human TRVP4 to the patient concurrently with a cancer treatment or subsequently administering the cancer treatment to the patient, wherein the TRPV4 agonist is selected from a group consisting of GSK1016790A, Bisandrographolide A (BAA), RN 1747, AB1644034, α-phorbol 12,13-didecanoate (4αPDD) 5,6-EET, acetylcholine and App441-1.

2. A method for cancer treatment in a patient in need thereof, the method comprising administering a TRPV4 agonist or a vector comprising a DNA sequence encoding a human TRVP4 to the patient concurrently with a cancer treatment or subsequently administering the cancer treatment to the patient, wherein the TRPV4 agonist is selected from a group consisting of GSK1016790A, Bisandrographolide A (BAA), RN 1747, AB1644034, α-phorbol 12,13-didecanoate (4αPDD) 5,6-EET, acetylcholine and App441-1.

3. The method of claim 1, wherein the cancer treatment is chemotherapy, radiation therapy or immunotherapy.

4. The method of claim 1, wherein the DNA sequence encoding the human TRVP4 is SEQ. ID. NO. 3, 4 or 5.

5. The method of claim 2, wherein the cancer treatment is chemotherapy, radiation therapy or immunotherapy.

6. The method of claim 2, wherein the DNA sequence encoding the human TRVP4 is SEQ. ID. NO. 3, 4 or 5.

* * * * *

UNITED STATES PATENT AND TRADEMARK OFFICE
CERTIFICATE OF CORRECTION

PATENT NO. : 9,078,856 B2  
APPLICATION NO. : 13/703765  
DATED : July 14, 2015  
INVENTOR(S) : Charles K. Thodeti et al.

Page 1 of 1

It is certified that error appears in the above-identified patent and that said Letters Patent is hereby corrected as shown below:

In the Specification

At Column 1, Lines 16-18:
"This invention was made with Government support under Grant No.: CA 45548 awarded by the National Institutes of Health. The Government has certain rights in the invention."
Should be replaced with:
— This invention was made with Government support under Grant No.: CA 045548 awarded by the National Institutes of Health. The Government has certain rights in the invention. —

Signed and Sealed this
Fifth Day of January, 2021

Andrei Iancu
*Director of the United States Patent and Trademark Office*

SEQUENCE LISTING

```
<160> NUMBER OF SEQ ID NOS: 5

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
gacggggacc tatagcatca                                                  20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
aacaggtcca ggaggaaggt                                                  20

<210> SEQ ID NO 3
<211> LENGTH: 50319
<212> TYPE: DNA
```

<213> ORGANISM: Homo sapiens

<400> SEQUENCE: 3

```
ccggccggga ttcaggaagc gcggatctcc cggccgccgg cgcccagccg tcccggaggt      60
aagtggggcc cgggcccggg aggggcggct cagccgaggt cccctcgcgc ccctggggac     120
atctccgtgg cccgtccggc tccgggggt cccgaggctc caaaatgcgg gccaggggcg     180
cgggagacgg aaggcaccag gttccgcagg cgccagcctc tcagctaagt gcccttgggc     240
cggacaccgg ctctttgggt ctcggtttta tcacctgtga atgggcacc aacgtggggc     300
ctggggtagc aggtctgggg ggagggcggt tcggttccct gagacccaa gccagggaac     360
caaaggcccg gagccttgca gcccaccta ggagacttgg aagagggatt tcgggggacc     420
taaggtttgc ccttggcccc tgagcatgtc ggagggaatt tggagtctgg agcttccaaa     480
ggcttcttct tggttactga gtcccggaga gacggctgtt cctccaaga ggcatgaaaa     540
tctttaacct ctagttctgc cctggactct caggacgtcc cggggcggg tggctcctgg     600
ggtgggtag cggggtggg ggtggggag agagagactc ccacactccc cgcttgcctg       660
gaaacaccaa ccacagatgc attcatcgag ccacccactg ctccagcctg ccccagctgt    720
tccctctgtc tgtcctctct gttttgcaga tggggaaact gaggcttagg tcggggatct    780
agacaattgg gatttaaacc cagggactat ccagccccaa agcccttccc accacaccag    840
gtggcctgtc ctggggccag ctctgcacac agggcctggt gccccgggg tgcttgggaa     900
gtggcagggc agaggtgggc cctgtggctg ttctggctca gcttctaaaa caagagcctc    960
tgctgggggc agaggggccg tgaacccctg aaatgttagg cagatacct gtgggagctt    1020
tgttctggga tgctaagaac cgcttgagga tttaagcttt gccactttgg ctccggagca   1080
agggcagagg gtaagtcggg actcccggg ctcctgagga gggtgacgag gtgggctttt   1140
gggggaacaa gggtagaaag gtcaggcctg ggttatctgc ggggctaaga gcgggcctgt   1200
gtggggcccg gggtgtgctc tgcagtcccc tgctgtgtga ccttggcctg gtcccttagc   1260
tgtctgagcc tttgtgttct ctcctctgta atactggggt gcctgagggc aagcccccag   1320
ggctgtcgtg aggaccgatg accttccagg aacctggcac agccactgtt ggctgccatc   1380
aatgtttaac cagttgtcgt tgccccaaac attttcttaa caagagggt gaaaaaagtc    1440
aattggccat ttccacattt ctctagttca ttctgtttga agaatgatgg gaaccagaaa   1500
gcctggacac ccaccttgat tggtgaattg cacgcggaag gggtcccaga cacaaatggc   1560
aaatggcagt catagttcag ggcggttcac tttgtaagat caaggtgggg ctgttttgaa    1620
atggaggtaa ccagggaatg gttgcctgaa caaaagggt gtgatgcccc caggagggat    1680
gtttcacatg agctccggtg aggatggctg ggattcccca ggtgaaaccc agataccta    1740
tatctgggga aggggctgtg gaggttcctc ctgccttatc tggtgccaac tgggcctctg   1800
ccacttactc cctcctccag caaatgctct ctgcaagctc acctgtgcca gctctgggct   1860
gggcactgga gcagtgagat gcttccaatc ccagcttcgc tgtagcctga ggcgtgtgaa   1920
ggcaagaagg attttccctt gtggccccc ggggaggagc tcccacacct gacttgtgag    1980
catctagcaa ggtgtgcatg gatggccgac gcttagtaaa tgtatgctgt ggaatgatg    2040
gggtcagggg agaatgccgt agggtaggag gactggccca ggaaggaccc acgagggctt   2100
ggtcaaggta tgtttaagc cgcaccttaa agaataaatg cagaagtaga ggaaagagta    2160
ttcaggcaaa gagaatggca ctagcagaga tatgactttt acctgttacc aggtggctac   2220
acctgggggtt tatagagcag agaaatagtt ctgtttgtct ggagtttgtg acgtgactgg  2280
```

```
aaagggtgag ggatcagaca ggcaggagct aaatcagacc cagaggccca gaagtcctgc    2340
ctgggagtga cacggttgtt tgtctgttct agaaaggtcc ctgtggctgc agagtgggaa    2400
agattggagg agctcagaca gagaggctgg ccccaaggct ggggaagtca tccaagctct    2460
gagtggagag cggcagctgg aaggagatgt aggagggaag gaaacacaca agactgagcc    2520
tcatgtgcct ggcacatagt aggtgctcag tcagtatcta tggcatggtt gtctgaacaa    2580
atacttttga tggtcaaa gtcctttgag ttccttcctc tgttcctagg gggatggggt      2640
ctacatgaag tgggtgtctc tactccatgc aggcccttga ccctgctgtc tgcctcagtt    2700
tcccccattt gactttggga aagacactcc agtccgttct ccaaattata gggacccagg    2760
taacagctcc tcttgttgtc acagataggg tctggggagc caagataaca tttatttcat    2820
gccagtgggc cctctggaat gctccacatc gcccatttgg agcagaattc acctgttaaa    2880
gattaattcc gatctcttga gataagtggc tgctgttatg aactctgggt acaaggttct    2940
gtctggcttt agccaaccct gggttgcatt aacaactatt atgatggtgg caagcccttta  3000 ttgagcactt actgtgtgcc aagcactgag tcaagcaccc tcagcacatt tggatacaaa    3060 actattttg tctctatttt tcagagggca gaatgaggtc tagagggtga aatctcttgc     3120
ctgggttctc tcagctgaga aggggcagag ctgggacctg aatcccattt gtgtgattgc    3180
aaatccatcc cttcacctgt aaggtggccc gtccccattt gtctggaccc tcattggggt   3240
gcctggggtc atggggagc tactctgcag tccagagata ggaacctgag ttggccgggt    3300
gcagtggccc acacctgtaa tcccaacact ctgggaggcc aaggcaggtg gatcggtcga   3360
gcccgtgagt ttgagaccag cctgggcaac atggtgaaac tctgtctcta gaaaaaatac   3420
aaaaattagc cgaacgtggt agcacgcacc tgtagtgcca gctacttgag aggctgaggt   3480
gggaggatcg cttaagccca ggagtgagag gttgcagtga actgcgattg tgccactgca   3540
gtccagagca agagatcctg tctcaaaaca aacaaagagc ctgaactgca gacaggcctg   3600 ggcttaaaact gcatccgcat gtttaagaca ggcctgctat tccccgctgg aggagctcag  3660
ggaagccacc tggcctctct gggcttccat ttcctcctgt gtcaaaggga ctctcatccc   3720
actttgcagg gatgacccaa ggcacgtgga tggggtctg aagcacagct cttctgcctc    3780
agcccgtgtc agctcccctt gtccccaggc ccattccagg gcatgttttc ttccagctta   3840
tcccccagac atcctcagag agcccctcca tgccaggtgg gtgggtggaa ggtattgggg   3900
gcaaagctag acttgcattt gggcaaataa tgatatgttt tcagcaatga aatatttatg   3960
agcattgact gagtgccagg agctgtcaac ttttttttact ttcctgattt aatgcttaaa  4020
aactagggct ggagcccagc tgcccaggtt caaatcccag cttcaataa gttccattat    4080 tcctttggcc tcagtttcct catctggaca atggggataa ggtaatgcct gccttgctgg   4140
gaggttgtgg acagtcttca gcacaacctt gagtgtttag tttaaaacca gcatctattg   4200
cctgttgttc actttttttt ttatttatta ttttttagaga cagggtctca gtctgttgct   4260
caggctggaa tgcagtggtg tgatcatagc tcacagcagc ctcgaactcc tgggctcaag   4320
agatcctcct acttcagcct cccaagtagt tgggacacac ccagcttatt aaaaaaaaag   4380 gttttttttca gacaggggtc tcactatgtt gcccaggttg gtctggaatt ccagagctca   4440
agtaaccctc ctgccttggc ctcccaaagt gctcagatta caggtgtgag ggctgatgtt   4500
cattttgatg gtgtcacagc ttccccactg ccggggggtgg gcaggggcag gaatgctgag  4560 cccccatttta cagctgagga aatcgagact cagagaggaa gcaatttacc cagggatgcc   4620
```

```
cagctggctc atggcagagc tggagctgga agccagatct gagtgacact ggtgtccttg    4680
ggtccacgaa aagcccagtg ccagcttag cttcttgcgt ggaaagctac gctaggctca     4740
cccaccttgg cgtctgagcc accttagctt acctcccagc tccgccagtt gctgctctgt    4800
gacctcagaa agtggcttaa gctctctgtt cctgggcttt gctgaggtca gagctctgcc    4860
aacttgagga gggatttggg ttattctggc tgctgctctt gttctggcct gggctccttc    4920
aacctcgggt gcccttgcag cccatgagct ggcaccccag tggccggaca ggaatgagga    4980
agggacaggg cctcactttc aatgtgactc tgacttcctt cccacccta gccccttcct     5040
gagcattggt ttccccttc tgccccgagc cctggccact gccggctgtg tgaccccaag     5100
gaggttacat cacttctctg agcatgtttc ctcatcggtg agggaggatc acacgagacc    5160
acaccaggcg cacaggaagc ccttgccggt ctccagatga ggtcagggca ttggaaaggc    5220
cacagaagga ggcgggggct caggggacag acaggcgggc cattgaccaa acgggaatat    5280
ccttctattt ctttggttag tgagtaacag cagcccctct tgtccaccca ccctgcccct    5340
tgcacaaaga gctcctcagt ctcaccaggc gcccgttttc ccctgagggt ggagtggcct    5400
gggttccacc cggttgaccg agtgggctgg ccaccttctg ggaccattcc ctgtgtgtgt    5460
gtttgtgtac gtgtgtatgt gtgtgtatat tgatgtgcgt gtgtatgtgc gtatgtgtgt    5520
ctgtgtgtgt atgtgtatgt gtgtatatgt atgtctatat gtgtatgtgt atatgtgtat    5580
atatgtgtat gtgtgtatat gtatgactat atgtttatgt gtatgtttgt gtatatatgt    5640
gtgtatgtgt gtatatgtat gtctgtgtgt atgtgtgtgc atatgtgtat gtatatacat    5700
gtgtatgtgt gtatgtgaat gtctatgtgt gcatgtgtgt atgtgtgtgt atgtttgcgt    5760
gtatatgtat gtatgtgtgt atattgtgtg tatgtatgtg tatatgtgtg taatgtgtat    5820
atgtatttgt gtgtagtgtg tgtgtgtgtg tgtgtttatg gagggtgggt tccatgggct    5880
ttgggctgag accccagcag gtgagggtgg gacagggggc atggggttga ctgacccatg    5940
ggtctggctc actcctgtcc ctgcttggca cacaggaggg gctcaggaat acctgtagat    6000
agagtgaagg gatgaatgaa ggaaggaatg agtgactgga caagccagcc aggcagggca    6060
tcagaaggaa gcacctgctc agatacaggc tctggctctg agaccaagtg tgcttgagtg    6120
agtgtcctgg tcttgttgag cctcaatttc ttcatctata aaatgggctc acgatagttg    6180
tcctcatgag aggtgttggt cttataggcc agaaaacccc acacatagca ggtgctccgt    6240
aagctgtctg ttaaaaaatg gatgggagga agctaattag ttagctgggc agaggttcgc    6300
tttggagacc tgtctgccct ggagagaatg actaagcccg tctttcactc ctttcctctg    6360
ttcattcatt cattcattca ttcatccagc aaatacatct tgagcagctg ctatgtgcca    6420
ggacctgttc caggcatctg ggcctcagca gttaccagaa gggagtccct ccgccctaga    6480
gcttttgtcc gagtgacatc attccacacg cagtgctttg aggccacttt tgtgagactct   6540
gatacccaca atgacaagta atccagcagt gggaactgtg atgagctccc ttttacaggt    6600
gaggaaactg aagctcggag aggtcaagtg atccgtctgg ggccacgcag ttactaaatg    6660
gcaaagtcaa gattcagact ccaagcctgt caccactgtg ccatcttgtc ctgctgagtt    6720
ccaagggata tggcgttgag aaggggggtc ctagggagag ggcatggtag cccccaaagg    6780
gatgaatgaa ctcaaatgga tttaaaagca gatggttgga agtctagcca cattcacttc    6840
ctgtagcgtt gtggactcag ttaaatctca ttctttctga tcttcagttt gttcatctgt    6900
gaaatgataa caataacacc gacctcaaat gagagagaaa tgtgaaagtg cttagcatat    6960
gataggtatt ggataaatgt cagcccttac ctccttccc ccgggactga ctttatacat     7020
```

```
ctgggaatgg agacaataat atttaatgtc tatagttatt atttggatta aaatagatag   7080
aaggggccag ccatggtggt tcacgcctgt aatcacaaca ctttgggagg ccaaggtgtg   7140
tggatcacgt gagcccgggc attggagact aacctgggca gtagagtgag actccatctc   7200
tacaaaaaat aaattttaaa agtaggaatg gtggtacatg cctgtggtcc cagcttctgg   7260
ggaggctgag gtgggaggat tgcttgagcc tgggaggtcg aggctgcagt gagctatgat   7320
tgtgccactg cactccagcc tgggtgacaa agccataccc tgtctcaaaa caaaaaacaa   7380
ccaaatggga ggtgctgtgt gaagtgtgcc atggagggta ggcattactg atggtacatt   7440
gcaggcatta gcctcagtca taattccaag cagttaaccc ctgaggcagc agcttactgt   7500
tggcacagac tggtgttgag gtgggctggg acagaggaag gatctcaaac tggttttctg   7560
ctgccttggg ctcccttccc cgactcctgc cccatccact cataacgggc acctgccctc   7620 ttcccccctcc tctgatttgg caaactcggg acttttgctc ctagaagtgg ggtagaggaa   7680
cgtatgcatg gacgagtgtc ctgtcccttc tggtccttag tctcccagct gggaggcagc   7740
ccttgtcctg acagccttct aaaggtgaca gaagatggaa atgaggtggc gaggaaaccc   7800
tttccaaagg tgaggtctct gcagtcacga gccctggttt tggagccggg aagtctgggt   7860
tccagtgcct gcccagttct gacctccctg gacctcaatg tcatcatccc ccacctccca   7920
ctgcaaactg agggaatgtt agcaagaatg gcaaagcagc cattgaacat ccttatctgt   7980
aaaatggggg taataattgc tacgacctgg gtggggttaa gctgtatttg ctccatagtt   8040
atttggtata cagtacattc atgctttaaa ctaaaaaata agttcaagtt cattgaacac   8100
ttggtgtttg ttgggcactg cactgaaggc ttgaattatc acatttaatc ctcacaatag   8160
ctctttgggg taggagctgt tattttattt tttaatattt taaaaaataa ataaatttat   8220 ttatttttg tagagatggg atctcaccat tttgcccagg ctggtctcga actcctgggc   8280
tcaagcgatc ctcccacctt ggcctcccaa agtgttggga ttacaggtgt gagccactgc   8340
acccagcctt atttttagt ttaaagcatg aatgtgctat acaccaaata actatggagc   8400
aaatacggct taaccccacc caggtcgtag taattattac tcccatttta cagataagga   8460
aaccaaggcc cagagatgag atgtgacttg tgcaagacca tacagccagt gagtggcaga   8520
tgagatgtaa agcattgatc aggcaacgtt ctcagactat agaatcctct ctggagttct   8580
ccgtggctgt gaccatcctc taggagaggg gctaggccag agagaaggcg ggcctaaggt   8640
tttgttttgt tgagatggag tctcgctctt gtcgccccccg ctggagtgca gtggtgctat   8700
ctctgctcac tgcaatctct gcctcctggg ttcaagagat tctcatgcct cagcctcccg   8760
agtagctggg attacaggtg catgctacca cacccggcta attttttgtat ttttggtaga   8820 gatgggtttt caccatgttg gccagtctgg tcttgaactt ctgacctcaa gtgatccgcc   8880
cacctcggtc tcccaaagtg ctgggattac aggcgtgagc cactgcgccc ggccggacta   8940
agaatttgat gcctccctcc tcctgggctg gagctgagta gcatgttctc aagcagggct   9000
ggctgagagg gtggaatcct ggggctatgc tctgatggga aggaagcgag ataagggaag   9060
aaggacctgg agcctcctgg ggtagtgact ttgtatcctt gagctcctac tacgtgccag   9120
accttgtttg aaacccttta tgtggctggg cacggtggcc gacgcctgta atcccagcat   9180
tttgagaggc cgaggcggtc ggatcacctg aggtcaggag ttcgagacca gcctggccaa   9240
catggtgaaa cccgtctcct actaaaaata caaaaattag ctggcgcagc ggtgggcacc   9300
tgtaatccca gctacttggg aggctgaggc aggaggattg cttgaacctg ggagacggag   9360
```

```
gttgcagtga gccaagattg tgccacttat actctagcct gggtgacaga gcaagatcct    9420
gtctctctct gtcacacaca catgcgcaca cacacacaca cacacaagaa agaaaaaaaa    9480
gaaacccttt atgtgtgctt aatctccatg acattcccat gttgcaacaa ggaaactgag    9540
gttctgggag ggaagtgacc tgcctgaggt cactaagcct ggaagggtca tttagatgta    9600
attcacatac tcataactca gtcttttaaa acgtacaatt cagttggttt cttagtgtat    9660
tcagagttgt acagacatca gcactatctc attccagaac attttcatca ccccaaaaaa    9720
ggactctgta cccattagca gtcaccactc cccactccca gccctggca acaactaatc    9780
tgctttctgt ctctgtggat ttgcctgttc tgggcatttc atataaatgg aatcctgcaa    9840
tatgtggcct tttgtgtcta caaggtgcat gctcttaacc attaagccac accgcttctt    9900
ggtggctcct acccagggc cgggacccTT ggaaatgact tggtccctgt gaaagctcag    9960
agggggcatct gtgtgtgctg tcagccggcc tccctccagc caagggcttg cagaatgacc    10020
aaatgactgc cgtggccacg ctggccttgc cctccgtggg gcgcggtgag tcaccccaga    10080
cctgccctgc ctggggtggtg tgagtgcatg gggtgggggc ccagcaggac actgggctc    10140
tgtctgtcct ggacaggcgg ccactgtgca gcaaacagga agcgggctgg gccgagacct    10200
gctaggtaaa tacaggctgg ccaggaagg tgctgggcat ggcatgatgc cccctactg    10260
ctgccgcctg ccaagtgcct gggagccgtg gggtagcctg gcaggcagta ggttcgcct    10320
ggccaaggag ttgagctccc agccggctgt cccagcagc cgccacttcg aggtggctgc    10380
cagagtctac ctccaaggct ctggatctgg ccgctctgcc ttctctagga gtcattgcct    10440
tccttggtcc tcagtccttt tgttcatctg ttccctaat gatactaata aatagtacac    10500
tgatactgat gattccaaca gcagccatgc ttgactgaat gcatgctctg taccaggcac    10560
tgggctcagt gttttgcatg ctttatctca tgtaaccctc acgacagttc ccttggggta    10620
ggtgctagga tcattgccat ttttcaggtg aggaaaccga ggcatgggca ggccaggtga    10680
cttgcccaga gctggtgaac tggtggttcg tcagggactg cgacccatcc cccactccat    10740
tctttctcca gcttctcct ccagagttc ccttgtcttt gtaaagtgtc catcaaaggc    10800
gcaggtcccg gggatgcatg ggttctaatc ctgcctcccc cttctggag caaggcaatg    10860
ccagacaaat gacttcgcct ctctgagcct cagttttctt acctggaagg tggggagggg    10920
gtggacaggt ctgggatttt ctctctagta acagcaaagc tcagagtcct tgtcttccta    10980
gtaccttcct atccacatgt ccccggcaag actgatttgg aatggcaggc actcacagtt    11040
gtgtttattt gagggtacca caggaagtgg gggcccccaa attggctaag gagcccccagg   11100
gtggagggag gtagaagcac actgggtctg tctgggagcc tgagcaccttt ctctgtgggc   11160
tccttcctac ccatggattc caaccccac ccacctcccc actgcccacc cactcaccca    11220
tctcttctgc tttccttctc cctgtgcccc aggccacacc attcctctgt gcaccctgca   11280
ctttcccctc tacacctttg tccttgacac ctcctctgcc ctttatcttc ctcctcctcc   11340
tcctcacagc ctttcccct ccccatcagg attctggctg cccttgctct gcaaccctgc    11400
ctggaacttc aggtccctga tcttacagcc taaaaaaacc aaatattcat tgacacctca   11460
ttttgcttca gcaccatgct gaatgctggg gacacagggg acacgaaata gtccctacca   11520
catgaaacta aaactctgga ggtgaagaga gaagatgaat caaagaataa tatataggcc   11580
gggtgcggtg gctcacacct ataatcccaa cattttggga ggctgaggca ggtggatcat   11640
ctgaggtcag gggttcaaga ccagactgac caacatggca aaaccctgcc tctactaaaa   11700
atacgaaaaa ttagccgggt gttgtggtgc atgcctgtaa tcccagctac tcgaggaggc   11760
```

```
tgaggcacga gaattgcttg aacccaggag gcggaggttg cagtgagctg agatcatgcc   11820
actgcactcc aacctggggg acagagcgag actctcttga aaaaaaaat acatatatag    11880 aaaagtttaa tcgtgggaag tgctgtaaag gaaggcacat gttactctaa gagtaaagag   11940
caggggaaac aggagggctt ttcagaggaa gtgccctta acatgaggcc tgaggagtaa    12000
gtgggagcca gccagcgaag ggaagggcat tccaggcgga gggaacagcc taggcaaagg   12060
cctggaggca gagagagcca tcagccttcc ctcctggact gcgagttctc tgaggttcca   12120 cactttatg tctcccctgt gccctgcaaa caggtgccac tgcattgatg cctggtggaa    12180
tgaattgatt ccagaaggga gggaaccggg agaaaccagc tccctggatt cctccccgct   12240
ggggcggagc aggtttgcat gcccaaactt gcccccagat ttaagcagct ttccttggtc   12300
acgtaatcag gaggatggga tttgacaaat gtttgccagg gtttccatga gatcaggcaa   12360
agccgcgggt aaccccgagg atgggcccct ttttccaccc tccgcaagtt ggggcatggg   12420 gacgagcca gagacctcca ccgcctttga atccgggatt ctcagagaga agccatctgt    12480
tgtgcaatct gctgtttatt gaggctttct ttatgccagg cacttgactc aaggtatata   12540
cctctcacaa cgaccctatt acgatccctt aatagggcag ctgagggccg ggcgtagtgg   12600
ctcacgccta taatcccagc actttgggag gctgaggcag gcggatcacg aggtcaggag   12660
atcgagacca tcctggctaa caccatgaaa ccccgtctgt actaaaaaaa tacaaaaaat   12720
tagccgggcg tggtggcggg tgcctgtagt cccagctact caggaggctg agcagaagaa   12780
tggcgtgaac ccgggaggcg gagcttgcag tgagtggaga tgcgccactg cactccagcc   12840
taggcgacag agggagactc cgtctcaaaa aaaaaaaaa aaaaaaaaa atagggcagc    12900 tgaagaaagt gaagatcaga gaggttgggt aacttgctca tactcaccca gcaagtgagc   12960
tgtgggtctg ggatctgacc ctctggtctg cctgacgtca aaatgtgccc caccggctca   13020
gggggccatg agagcagaaa gccaggtttc tggaaagcct ggggtctctg tctagggcag   13080
aaaggaaggt ctggggaccc tggctcagcc ctgtatctca tcaccctact caggactcct   13140
gcacccctta acttgcccac tcctgagccc ttctggtcta tgcagttctt aacaccatcc   13200
gacatgactc tgctgcttga tttgtctagt ttattgtttc cccaccagaa ggtctgcccc   13260
caaagggatt gatatctgtt ctgttcacat ctgtgtccct agtctagcac agtgcctggc   13320
acatagtagg tgctcaataa atgtgtggaa taaataggta gctggcttct actgctgccc   13380
cttgggccct ttccagagga agatgcagat tctttgtcca tcctacacaa ctgccatctc   13440
tgtgtggacc accattcagt atatatattc taaagaagag tttgaatata aacctgcttt   13500
tgaatatata ggatttaaaa ccaacatatt caaaaccgc tactttggct gggcgcagtg    13560
gctcatgcct gtaattccag cactttggga ggccgaggcg ggtagatcat ttgaggtcag   13620
gagttcaaga ccagcctggc caacatgtga aacccgtct gtactaaaaa tacaaaaatt    13680
agctgagtgg tagtggcatg tttctgtaat cccagctact tgggaggctg aggcaggaga   13740
attgcttgag cctgggagga ggaggttgca gtgagctgag attgtgccac tgcactgcag   13800
tctgggtgag agagtgagac cctgtctcaa caaacaaaca cccgctgctc tgaatgaacg   13860
ctgttgtgaa gatgtcagtg tgtgaggatg ttcacagtcg tgcaggaacg ttcttgggtg   13920 cctcccctgat gcacacctgg tgcagctggg agcttcccca ctgtggaggg gctcctggta  13980
ggaggcattg tgagcccgtg cgggaacgaa gggcccacca tgcctgctca cagtgggcac   14040
acacacatgc acacgcccat ggaggaaggt gggaagaaat gtacatgaca gtcacacgca   14100
```

```
gaggagacac atgtggactc acacccaggc tctcagcctc tctccctgcc tgcatccccg   14160
acttccctcc ctcctaaaac tggcatgagt ttggaatgtg taataacagc ctttagggca   14220
aattagaaca gggagtaaac tctttctctg accacagaga acaggacagt gtttggggag   14280
ggaattgcca cagagcagca gagccgggtg tgtgtgtgtg tgtgtacaca tgcctatgtg   14340
tatgtgtaca cgtgagctag tgtgtacaca ctcctgagtg ctgtgatgtg aaggagccc    14400 agggctagga gtctagaggt tttcttcaaa gccatttgct ccctagctgg cctctcagag   14460
cctccgtttc cttagctgta aagtgggagc aatagcctag ctttgttcag gttcttcggg   14520
ggattgaatg agagaggggc ttggtggatt ttagcatggg ctataaaatg tcaggctgta   14580
gtgctggcac gtgtgtgcat gtgtgttttg gggaagggga gtaaggagga caggtaaatc   14640
aggaccatat catagtggtg atgatgataa ttaaatgtga caagatccaa catttatcaa   14700
atatttctta ggtgcccaag aaacacttga cctgccttat ctcccagaag ccctacaagg   14760
gaggtgctat tattgcaatc cccatttttac aagtagagaa accgaggctc agagagatga   14820
gaatgggcgg cagtaatcat cccttcctcc tgggggtggt tgtgaagctt aaggagaca    14880 ctgtaagcgc tcgggtggta ccctggtact ccatcactaa cctgctgtgt gacctcaggt   14940
aagtcgctta gcctctctga gcctcagttt cctcatctgt aaaatgggaa tgattgcaat   15000
acctacctcc agggcagatt ttctcaacct cagcgctgtt gatgttgttg actgggttat   15060
tctgtgtggt gcgggctgt cttttgtttt ggaggatgtt tactaccatc cggcatggcg    15120
gatcccagca aaggcccctg tgcaggcctg gtgaggtggc cgagcttcct ggtggggagg   15180 ccttcccct ctcctccctg gtcaatctat ttgaggtga ggatggctcc ccttcaccct     15240
cacctggcac ccaggacatc cccagtccat ggagggattc aatctgggct ctgcagccag   15300
ctgcccgcat ttcagtcctg gctctgtcac taacctgctg tgtgacctca ggcaagtcac   15360
ttagcctctc tgagcctcag tttcctcatc tgtagaatgg aacgatcgc agtacctact    15420 tccagggcag atgttctcag tctcgacgct attgacattg tgggctgggt catttttttg   15480
tggtgtgggg ctgtctttg ctttggagga tgtttagtgc catccctggc cttgatctac    15540
cagatgccaa tagtgctccc tctcctgtac agttgtgaca acaaaacatg tcatcagata   15600
ttgccaaatg tccttagagg aggagcagaa ctgtccttgg ttgagaacca ctggtctgga   15660
gtcatgatga gggctggatg aggccctgtg ctgggcacag cctgagctac gtcatcaggc   15720
gaggatggtg atttagttca taattattat ttcatcctaa ttagaatgct aatcatgatc   15780
gcggcgtgac ttgccgaagg ccacacagca gccatacagg ttgacagttg ctgggagagg   15840
atttgaacct gggattggct ggcaccagag cccccatttt ggagtcccca ggaacctggg   15900
gtgctgtcca ggcttagggg agggctatcc tcctgagggg aggagggtgc aggcatggtg   15960
ggggatggaa ggaccttctt ggctgccttc tctggccttg ggagctccct gggatgggt    16020 tccattagcc cctgaggtgc catggtgagg ggtgcagtgg atagaagggt actgaaaaca   16080
cagagggtgc gcctgatgcc tcgtctcccc ctgacctcag ggccccagt gaggtggaca   16140 gggccatgcc caggagagtc taatccacct cccgccaatg cctgtgcccc tgcagatgcc   16200
cctcctgcct cagcaacccc ctggccccca ttcctgcaga gcaaagccca aatgcatgtg   16260
gcagccatga gggactaggg atccagatcc ccctctcctg tctggccagt cgaaaggact   16320
tcgtgtctcc agaggtccta ctaggtgctg gaactgagta ggtgcctcac atgctggagg   16380
accctaggag gaggcgtggt cactccagtc ttacaggtgg gaaaaccacg gggcagacag   16440
aggaagtgat ttgcccatgg tcaaacggct aatgaccagg gccaagagag gaactgggtc   16500
```

```
tcatttcaga acctggcctc ctaacttctc tttcttcgtt tggttataat aactgaaagt    16560
cccactctat ttacagatga ggaaactgag gctcagagag gctaagcaac ttacctgagg    16620
tatttatttt tagatagagt cttgctctgt tgccctggct ggagtgcagt ggcgccatct    16680
tggctcactg caacctctgc ctcctgggtt caagtgattc tcctgcctca gcctcctaag    16740
tagctgggac tacagtcacg tgccaccacg cctggctaat ttttgtattt tttatagaga    16800
cggggttttg ccatgttagc caggctggtc tcgaactcct gacttcaagt gatccacccg    16860
cctcggcctc ccaaagtgct ggggttacag gcgtgagctg ctgcactgag ccaaaacccc    16920
actttaatcc cagaagtggc actggatata tctgacctca cttcccactg cctgcaaccc    16980
tatgaagaag tgactacaat tgtacccatt ttgcagagga ggaaactgag gcttggggag    17040
ctcaagtaac ttacctaaga tcacactaca tgtaaatagc agagctggga ttagaaccca    17100
ggcctgaatg actccaaagg ccaggctgtc tctcccttt  ggtgtccaaa gggaagccca    17160
cccccagtgg gagctctgac cctctgtgtc ctgctgcgcc cactaaggga ggcctcttgc    17220
tgtgtcccca cctctctggt ccaagtcttc cctcctggaa gccacagaac aaacaaggtg    17280
ggaactagtt tatttgtttt tctacgtgcg tattgggtgg gaaggtgag atgtacaaga     17340
gagggctttt cagacatgcc cctgcctccc gggtggggtg gtaagagttc caggaaactc    17400
acccttggtg cccagccctg cctggctggc accatgctac agagagcagg gcactgacag    17460
ccaaccagtg gggccttgcc cctcccttgc cctggctcct ggctaagcac tggacccggg    17520
agccagagag acatggttca agtccagctc ttcttcctgc aagctgtttg ctgcctttga    17580
aagctgcttc ctcatctgag aaatgggaac aaatgacatc tttgtcataa agttttttcat   17640
ttgtgtgagg actcagggat ggacaagaca gatacatttc ctgcctcctg gcacccacag    17700
cctgggaacg aaccatcccg tgaacagctg ggataaagct tctgaggaga ggagcatgga    17760
tcctgggagc gagtgtgtgc aggccaggga gggcttcca gaggagccca gttgagctgg     17820
aacaccagtg gggaggagtt gaccagcaaa ggtgcaggga gggatcagca cttttgcactg   17880
gggagcagag tttgtgcact ggggaagtca actcaagtat tggagcctca gtttcctgtt    17940
ctgtaaaatg ggttcatcat gacagtgttt gatgaggaaa aggactgccg gcctacacag    18000
caagtccaca tggattttct gagcccctcc tgtgcctgaa gcccacggtt aatggttctg    18060
ccttagcagg tgcttaccac gtgccaggca ctgcactgca ctggccactg gactgcatgt    18120
tctgtccatg aggcttggat atccccatct tacagatcag gaagctgagg ctatgaaatg    18180
tcgacttgct caatgtcatg gaatgactaa gtgtggagcc tggatttgaa cttggctctc    18240
tggggctcca aagctggctt tcttggtcag cagtagggtc tgggatccaa gtatggggtc    18300
ccagcttgac cctgaagtcc accctctttc agctaatgcc cagggtagtt ggacctgggg    18360
ccaatttgtg tttccaggtt cgtgaaagag gctcctgttg cagttcccgc ctgaggctgg    18420
cggccaacca catctgggag tggcctccct gtgcccctgt cattacaacg gtggctttga    18480
agcagctggc agcactgctg cttgtccacg tgggagggg  cttcctggag  ccccgcccc    18540
tggccgggtt ctgcctgact ccccttttcat tcccttgcag gctgagcagt gcagacgggc    18600
ctggggcagg catggcggat ccagcgaag  gccccgcgc  ggggcccggg gaggtggctg     18660
agctccccgg ggatgagagt ggcaccccag gtggggaggc ttttcctctc tcctccctgg    18720
ccaatctgtt tgaggggag  gatggctccc tttcgccctc accggctgat gccagtcgcc    18780
ctgctggccc aggcgatggg cgaccaaatc tgcgcatgaa gttccagggc gccttccgca    18840
```

```
aggggggtgcc caaccccatc gatctgctgg agtccaccct atatgagtcc tcggtggtgc   18900
ctgggcccaa gaaagcaccc atggactcac tgtttgacta cggcacctat cgtcaccact   18960
ccagtgacaa caagaggtgg aggaagaaga tcatagagtg agtattgtta gcttcctggc   19020
ctgtggtctc ctcctctgta tccattcacc cattcatcat ccacccctct atctattatc   19080
cacccatccg tcgattcatc catccatcca tctgtccatc caaccatcca tacatctatc   19140
catccatcta ttcatctccc tatccatata tcatccgtcc atccatccat ccaaccaccc   19200
atctattcgt ccatccatcc aaccatccac acatctatcc atcaatccat tcatctctcc   19260
atctctatat cctccatcca tccatccaac catccataca tctatccatc gatccattca   19320
tctctccatc catatatcat ccatccatat atcatccatc catacatcca tccatcatcc   19380
agccatctat catctatcca tctatccaac catccatcat ccatcatcca tccattcatc   19440
tattcattta tacatcatcc ttccatctgt ccatctattc atctatccat cattattcca   19500
tctgtccatc tatctactat ccatccatct atccatctac ccatcatcca tccatccatt   19560
catccatcat ccttccatct gtccatctac tcgtctattc atcattccat atgtccatct   19620
atccattaat ctatccatcc atccatatat catctatcta tccacccatc atccatccat   19680
ccatctaccc atctatccat catccatcca tctattcatc atccatctat ctattaatcc   19740
atcatccatt actctaccca tttacccctc tgtccaccct tccataggac atttgtctgt   19800
tcatccattc atccatccac ccactcattt atacaatgca tccatccacc cactcattta   19860
tacaaatgca aatgcattta tacaaatgca aactcagcca tttacccatt tacccattca   19920
cccttccacc cactcattta tacaactatt tactcatcta actctccatt cattcatctg   19980
cttttttttt cttttgaga tggagtcttg ctctgttgcc caggctggag tgcaatggca   20040
tgatctcggc tcactgaaac ctccacctcc tgggttcaag caattctcca gtctcagcct   20100
cccgagtagc gggattacag gcacccgcca ccacacccag ctaattttt ttgtattttt   20160
agtagagaca ggttttcacc atcttggcca ggctggtctt gaactcctga cctcgtgatc   20220
cacctgcctt ggcctcccaa agtgctggga ttataggtgt gagccaccgc atcccgcctc   20280
atctttttt attcacctac atatccacgt actcatctgt cccccattaa tctacttgtc   20340
tgtccatctc ttcacctaca catccagcct tccatttgtt tatcttctta tttatacatc   20400
tgttcatcca tccatccatc catccattta tccatctatc atctactcat tcatttaccc   20460
atctttacac ttttttgtcc acctatccaa tctatagatc cattgtccac tcattaaaat   20520
atctatctac tcatctaccc atctgtcagc catctgtcca gccatacacc catataacca   20580
accttccatt catctaccat tttctcatct gaatgtcatt tcatcttctc acctacccac   20640
tgtttctagt catctagcca ttcagctatc aaactattca tcattcattc atttattcat   20700
tcattcattc catttctcat gcttgattgc tcacctgcct gctgtccttc tttccttcct   20760
ctccttctct cttctaacca ccaattcatt cacccagatc tctgtccatc catttgtcca   20820
ttcactcttt tgtttgctta gtcactgact catttattca tttgctcatc ttttcttcca   20880
tttttgcatc tattcatcca tccatctccc taccttctct tcctggcaca catccagctg   20940
cccctcctgg gtcttcttca atcatcacct ccattcctgg ccatccagtg gctttcctga   21000
ggcttagaaa gagctggaaa ccccaaggca ttcaaccttc tttccaataa tgacagcctt   21060
gctgaaagaa aagacagact ggagagaagc cctggatggg gccacagcat gtggccccta   21120
tgacgcattc catgccaggc ctagctgggg acagggagcc tccagccccc ttgaccacct   21180
tgtctggtcc ccatcctccc ccagtgtgtt atgctggcat ctgcatgtgg tttgtgtggc   21240
```

-continued

```
actctgcaaa ctcagacatc ccgggttctg tttccagcat gactctattg tctgtcacct    21300
gcagactccc tgctttgtga ggttgagccc tccctcctgg tcctttagga agcccaggga    21360
cttccacaag cttttggcag tttggaggag ggagcagggc ttgcagtctc ctagccagct    21420
cctcctgagc ctcagcaggc cctgctgaac tgtatccttt ctatgtcccg gccctgctgt    21480
ccctaatgtg ccctgaattg accctttcct caactgctcc atgaaatctc ctctcggtgg    21540
cctgtgtgtg tgtcctggag gatggtgctg aggtctggag atgacctgga cttgcgtgtc    21600
ctcctctgtc ccctgctggc cacagattc atttatctct tggatggagc cgattcacct    21660
tcacagccct tgcttggtca agagccgccc cctttattta ttcacagtca ttgattcatt    21720
cagatgtctc tttttctttt tttttttttt gagacaggtt ctttctctgc cactcaggct    21780
ggagtgcagt ggcgctatct tggcttactg caacctccac ctcccaggtt caagcaattc    21840
tccagcctca gcctcctggg tagctggagc tacaggtgtg cacgaccaca accggctaat    21900
ttttgtattt ttagtagaga cagggtttta ccatgttggc caggctagtc tcgaactact    21960
gtcctcaagt gacctgccca cctcggcctc ccaaaatgct gggattacag gcgtgagcca    22020
ccgcacccag ccagtggatg tttcttgggt gcccactgtc tgccagtcag tggggttggc    22080
cctgaggctt caggctgagc cagaccagat ccacttctac tcaggcggca ctttccgttt    22140
agagggtgag acagacaaga agcaagtagc tgagcacatg gatgtgccat gtgagttggg    22200
ggaggtgctg aagttagaga gtgggtggat acaagaaagg taatccagga gggcttcttg    22260
gaggagttga catttaagcc caaagctaaa ggtcatgaag gggcagtcac agagagggag    22320
ggaagggtgt tgtaggtgga gagaagtgtg agtgcaaggg cctaaggctg agaggctct    22380 gcagatgtcg ccaaggaata gggcctcaca gttgtctgtg ctgaaaaatc tgtacaacct    22440
ctgctcagag gtggaaacta agggccagag cagcagagtc cccagtgttc ccatccttct    22500
gtccccaagc cttcccaggt cctgttgaaa gctggtgggc tctgtatctc ccattcccct    22560
cccgcaagcc ctcctcccca cccctacccc aggaagtcca ggctggtgga gtaagtgggg    22620
cacggctgag ccctgaaggc tgcctcagtg agatctggtg ggggcagtat tgcttttat    22680 tttttggctc aaaggtcaaa gttcaggaag aggtaaagtg gggctgcct aagtgccctc    22740 attagaggct gtatctgtgc ctgtgccct gtcaacagga gagcacgtct taccctactg    22800
tggatgctaa tgatccccctt tgccagtacc tgccctgaga tggaaaatct caaccctgg    22860 cgaagaggaa gggaggagag tggctgtccc cttctcatgg caagacaggc tgggtacagc    22920
cagatgccag ctttgtccac ccttgcaacc ccgtcccacc tgcttccaca acctgccctg    22980
gcctcagttt ccccaactgc attcccttc ccctctggcc ctgctgcctc ttgttagggt    23040
tttctctgtt ccctactct ccctcttct ccctcccaga cctgtgcct ccatcttcct    23100 ccttctcttt agtctcttat tcattgaaca gagtcttact gcatcccaag atgtgccagg    23160
cactgggcca ggtaagaatg tgacagagag agcattcctg cctcatggtg gccctgggct    23220
agctctttct ctctcagaac ctagcacata ataggtgccg aaataatgtt tgttgaatga    23280
ctgaatgagt gtctccaagc cctccagctc ttagtgtctg tttccttcct ttctctctct    23340
atctcttctc ttcccagccc tctctgtgcc acacccttcc gccatctgcc tctgtagccc    23400
cacatctctc ccatgcacat acaagctcca gacacacagt aggcactcat taataatggt    23460
aatatcaact aacatttatt gaatgtttac cgtgtggtgg gccatgggca ggtacatatg    23520
agcatggcct catttgtctc aaatgtttgt tgaatgaata aattaatggg ttagttatgg    23580
```

```
aatgaatgga tgaaatgcct catcttttag tctgctgttt ctttatttta tctttgtttt    23640
tgtctctttc agtttctctg ccttagtaag tactcaataa atgactaata tatgagtggg    23700
tgggtgagtg gatgggcagt tggatggatg gatggatgga tggatggatg gatgggtggg    23760
tgggtggata ggcagatgga tggatagacg agtgatggat ggatggatgg atggatgggt    23820
gagtggatgg atgggcagat gggtggatgg atgagtgggt ggatggatgg atgagtagtg    23880
gatggatggg tggacagatg gaggagtgag tggatgggta gatgaatgga tgagtgatgg    23940
atggatggat ggatggatga gtgggtggat ggatggatgg atcagtgagg gatggatgga    24000
tggatgagtg atggatggat gaatgggtgg atggatgatg ggtgggtagg tggatgggtg    24060
gatgctgggt gggtggatgt atggatgagg gatggatgga tggatgggcg ggtaggtgga    24120
tggatggatg ggcgggtagt tagatgggtg gatgaatgga tggatgggtg ggtggatggg    24180
tagatggatg gatgagtgat ggacggatgg ataagtggat ggatggatgg atggatggat    24240
gagtgatgga tggatgagtg atgaatggat ggatgggtgg gtaggtggat gggtgaatgg    24300
tgggtgggtg gatggatgga tggatgagtg ggcagatgga tggatgagtg atggatggat    24360
ggatggatgg gtgggtggat gggtagatgg atggatggat gagtgatgga tggatggatg    24420
ggtgagtgga tgggtagatg gatggatgga tggatgaatg atggatggat gggtggatag    24480
atggaggagt gggtggatgg gtagatggat ggatgagtga tggttggatg gatagatggg    24540
tggatgggta gatggatgga tggatggatg agtgatggat ggatgggtgg atagatggat    24600
gagtgggtgg ataggtagat ggatagatga gtgatggatg gatggatgga tagatggatg    24660
ggtcggtgag tggatgtgtg gatggatggg tggatagatg tatgggcagt ctgtgcattt    24720
ctttctgttt gtctccaccc aacacacagt aggtactagc tatagtttgt tggataaaac    24780
attacttagt ttttacatct gccccaacta cctcaccctg ttccttgtaa ggcttcagct    24840
gcctgcccgc caccacagtc tctgggtccc taaggccagg gacagtgggg caggcagggg    24900
atgagccctc ccatcaactt gcctccctac ctcctccagg aagcagccgc agagccccaa    24960
agcccctgcc cctcagccgc ccccatcct caaagtcttc aaccggccta tcctctttga    25020
catcgtgtcc cggggctcca ctgctgacct ggacgggctg ctcccattct tgctgaccca    25080
caagaaacgc ctaactgatg aggagtttcg aggtgagcca cccagatggg catagccagt    25140
gggacagcca ggggtgtggg ggaagcctgg cattgggggc cccctttccc ctcagcttct    25200
ttctttgggt cggtggactg cattggcctg gaaagtgcac tggacaggga gtctggtcct    25260
gtgtgtcctt caccatgtta cttaacctct ctgtgcctca gctacctcca tttattcatt    25320
ctttcattca ttcagcccTT atgtatgaaa aggttagtgt agtgggtaag cagagtccac    25380
ctacctgggt tcagattcta cctttaccag ttaagcgatg tgtgacctct ctgagcctcc    25440
gtttcctcat ctgtaaactg gggaataatc atagcatact cctggctctc atcccacaga    25500
gagcccagcg caggcagctg gagtcctgga gctcctgctc ccctgaggga aggtctggag    25560
ggatgggcag gtgtctgggc tggtagtcct gattctactt cttggggtct gctccacccc    25620
agcctagctt tagggctcca cttcctaggc tgaagcccca gcccagagag ctaacccttc    25680
agccttgtcc agattcaaaa cacccacctc aggacaccgg caccctccac agccccaggc    25740
cttacctgtg aacacctgca cccaaatcag ccacctgcaa tgtgctgggt tctgggtaag    25800
ccattattaa actggccgtg atctcacaag tcaagatacc atgtcaagaa gtgtgacacc    25860
aaggctgggc atggtggctc acacctgtaa tcccagcact ttgggaggcc aaggcaggag    25920
ggttgcatga gcctggagg ctcaggctgc agtgagctgt gatcatgcca ctgcactcca    25980
```

```
gcctgggtga cagacaggaa aaaaaaaaaa aaaagaattg tgatacctgc tatgaagaag    26040
ggcccatctt ggaaggcgga ccatggttgg tctacagcct aagtctgagg aggcttcagg    26100
gatgtcagaa gaggcttttt tttttttttt tgagacagag tttcattctt gttgcccagg    26160
ctggagtgca atggcatgat ctctgctcac tgcaacctcc gcctcctggg ttcaagtgat    26220
tctcctgcct cagcctccca agtagctggg attacaggca tgcgccacca cgcccggcta    26280 atttgtatt tttagtagag acggggtcgc tccatgttgg tcaggttggt cttgaactct    26340
cgacctcagg tgatctgccc gccttggcct cccgaagtgc tgggattata ggcatgagcc    26400
actgtgccca gccagaagag gacatttttt aagacttcag ttactttaag taaattaagt    26460
tcccaaacag ggtgaacaag tctgtgctac atcatccaca tataccttta tcaacctgtt    26520
tttttttttt tttctttttt tttttttgag atagggtctc attctgtcac ccaggctgga    26580
atgctgtggt gtgatcacag ctccctgcag ccttgaactt ctggcctcaa gcaatcctcc    26640
tgcttcggcc tcgagagtag ttgggactac aggtgcaagc taccatgcct ggctaaattt    26700
ttttttttct tttttttaa gagacaggtc tcactatgtt gcccaggctg gtatcaaact    26760
cctggcttca agcgatcctc ctgcctcaac ctcccaaagt gctgggatta caggcatgag    26820
ccactgaggc tggcctcaac ctcattctta ccctgaaaca atacgatgca gtatcattgt    26880
gtccatcagg agacaattac tggggccggg tgcggtggct catgcctata atcccagcac    26940
tttgggaggc tgaggcgggt ggatcaccta aggtcaggag tttgagacca gccttgccaa    27000
catggtaaaa acctgtctct actaaaaata caaaaaaaaa aaaaaaaag ccaggcttag    27060 tggcacacac ctgtaatttc agctacttag gaagctgagc caggagaatc acttgaacct    27120
gggaggtggg ggttgcagtg agccgagatt gcaccactgc actccagcct gggcgaaaga    27180
gcgagactct gtctcaaaaa aaaaagaaa atacaattgc tggatttatg aaaaatattc    27240
attcatggtt cctggccacg cgacgtggcc tcgtttggag gcacaagttt agagctgtgg    27300
gaggacgggg cttctctctg ctcctggagt agctcagtga tggcatgagt aatctcattc    27360
ggagataacc catgtttaag ccctggccaa atggcctctc ctggtccacc aagtacgtga    27420
ggcaaaagtg cggaatcttg gggtagagcg aatcctggga gatggatgct ggcacctgtg    27480
ccttcagcac caggctagct tgtcaaggcc tctggcttct tctgaattca ggactgagtt    27540
gggggcttct agcatagtcc aggaacccag atgcatgtgt gtctgtgcat gagtgtgggt    27600 ggggactct aagataggct ttggaggtgg gtctctgaaa ttgcagaggc tagcgtatgt    27660
gcatagaggg agacttactg tgaggtccat gatactaatt aagtgccagg gccctggct    27720 aaggccctt ctgaggtcct cgacctagtc tacgtcccac aaaacctgga tccgtccctg    27780
catggctaaa aggtcatgag ctcatctgat tatcagggaa gtctgggacg ccctcctgtg    27840 ccccccacctc ccctccgcag agtttcacaa cctccaattt ggcaattgtc aatttagagc    27900
ccctggctac agcaccccac cctgggcaga gccacttcgc cacctggtgg ctggttcctg    27960
gaactgcatg ttccacctca tctctgggaa gatgctgctc ctgacatctt ctcccaggac    28020
ccaggcgtcc cctccctggg tctataacct gtgtctgaaa gcccgaatcc agggtctcta    28080 gttccactttt gggtcaccta tggtttggaa ttacctgggg tgcccagctc tcgccttcat    28140
tcaatgtgtg ttaactcagc aaatggttgt tgggcaccta ccacatacca ggcactgtgc    28200
ttggcagagg ccgaatgata gtgagcaaag cagacatcac cctgccctca aggtgcccac    28260
aggctcctgg acaggaccat cattgaccaa gcaaccacat aaataagcac acagttatga    28320
```

```
actgtaacag gtgtcaacaa aaggctgtac tggaggattt gacctagtca gggaaaatcc    28380
aggagagctt cctggaggag gtaacacttg agcagagtct gagtgagttg cagttaacca    28440
ggtgaaaaga ggagggaaga atgtttcaga ttggggtggg ggttcagaga cagcaggtgc    28500
aaagaccctg tagttcaccg tggtctattg cagtctgaaa tgaccattcc agctgctatg    28560
tggaaagtgg ataaaggaag gccagagagg ctgggggaaa tgagggaaat aaaggaggtg    28620
tcttaggcat gtgagaggga tggtggctgg gccacattat tccatgagag gtttggtgtc    28680
gcctctgagc tgggcgccag gtggacagcg ggaaagcaac tgggaacaag acttgtccca    28740
aacaaccctg ctcctggaag ggctgagact agaattcagg tctcttgagt ctgccccact    28800
gattcccggc atttagggag acggttccta aatcccgtct catggattga taacagcaac    28860
agtaatattt atcaaagact gctatctgcc tggtactggg ctaatcaaca aacactgatt    28920
agctctttga tttcccttca tagctttaat ttagccagaa aggaccctaa gcagagaaat    28980
ggtcatacag ctgtggggag caaagccagg cctcaaacct gaggtgcctg gcttcagaac    29040
gggcacctga acccacacct gcgtctccca ccctctggcc attcctgagc ccctggctga    29100
ttttgccctg tccttgattc acaggggagt tttcaactta ctcttttgag atataaatca    29160
actcaggtaa ccataaaaat agctacaaca gaaagaaact tgcaaagaga catcagcaag    29220
cgttagtgag aggtgttaag gacccgctag taccaaacgg agagttgact tcatgagaaa    29280
gattcgatag tggatgaaac cttcagggtt attattgttg caccccctag aacccccaag    29340
attctctcct ggatccccta aggtcagttc acatccactg tggcacacag tcccacactt    29400
tggggaacgc tgcacccctc cactcccttc taggggcacc agtgtaaatg cttcatggga    29460
aaaggattcg atgctctgac aggtgggtga atgctgccta gtgtgtcttg cttttacagg    29520
ttcacagtcc ctgttagtgt atgaaaggct ctgagaagtc ctgtagtaag gaattatgat    29580
tggctttgtt taacccagca ttctaaccat ttatttgttt atgaagcact ttacataaat    29640
cttttcgagg gccaggtgtg gtggctcaca tctgtaatcc cagcactttg ggaggctgag    29700
gtgggaggat cacttgaggc caggtgtttg agaccagcct gggtaacaga gtgagatccc    29760
ttctctacga aaataaaaat taaaaaatta gttgagcatg gaggtgcaca cctgtagtct    29820
tagctgctac ttgggaggct gaggtgggag gatcacttga gcccaggaat cggaggctgc    29880
aatgagctag gattgcacaa ctatacccca ggctggatga cagagcgaga ccctctctct    29940
caaaaaaaag gatattaata aataaaaata aatacaaaat cttcccaaat aagattaatt    30000
aaataaatac caatctgtag gctgaagcct ctcacatttc aaagcaccta acccatgcg    30060
tttattgtac cctctcagca ccactggagg cagaaagata gagtggccct gggtccccac    30120
tggacagatg aggaaacagg cttggagagg agatgttgac agccaggaca tctgaccccc    30180
tacccagtgt tctgtacccc gatgcctgga agttcaaggt catgggctgg agcactgcgt    30240
catcttgtgt gtctctcttg ctagagccat ctacggggaa gacctgcctg cccaaggcct    30300
tgctgaacct gagcaatggc cgcaacgaca ccatccctgt gctgctggac atcgcggagc    30360
gcaccggcaa catgagggag ttcattaact cgcccttccg tgacatctac tatcgaggtg    30420
gggcccggg ctgggcaggg gtgccacggg ggctgatgga gacgctgtcc tttgcttgtc    30480
tgactcctga gacttttgat ctgggcctaa gtgccagcat gtacccagga cctgacaaat    30540
ggatggatgg atggatggat ggatggatgc atggatgcat ggatagatgg atggatgaag    30600
gaacggtaac taccccttcc aactttgttt cgagtttcag aatagaagat tccactgggt    30660
gcggtggctc ttacctgtaa tcccagcact ttgggaggcc aagggggca gatcgcttga    30720
```

```
gcccaggagt tcaagaccag catgggcaac atggtgaaat cctgtcttga caaaagatac   30780
aaaaaaaaaa aaataaaata aaagaaggcc aggtgcggtg gctcacacct gtaatcccag   30840
cactttggga ggctgaggtg ggcagatcac ttgaggtcag gtgttcaaga ccagcctggc   30900
caacatggtg aaaccctgtc tctgctgaaa atgcaaaaat tagccaggcg tggtggtgcg   30960
cacctataat ctcagctact gggaggctg aggcaggaga atcgcttgaa cctgggaggt   31020
ggaggttgca gtgagccaat atcgcgccat tgcactccag cttgggcaac aagagcaaga   31080
ctcatctcaa aaaaaaaaa aagatgcaaa aaagccagg cttgttggtg cacacctgta   31140
gtcccagcta cttgggaggc tggggtggga agatcacttg agctcagagg gtcaaggctt   31200
cagtgagcta tgattgtgcc actgcactcc agcctgggtg acagagtgag accctgtctc   31260
aaaaaaaaaa aaaaaaagat tccaagattc tgagatgcag cgagtctagt gatcatgaac   31320
tcgggatctg gccctaagat gctgtggtgg cggatactct aaggctctat gataataagt   31380
cctgagttca caagttctaa gaggcaaagg cagcagggg ccaagaactg gccaatccc    31440 cagttgagat tctgtaaatc agagttgacc ttcagatgcc tggatattaa gattcaaaat   31500
ccatgaatat tatatcttga gtccaaaatt ctgggaggcc aagtactgt tgtttcctct    31560 aggagttttc ttttttttga dacaaggtct tgctctgtta cccaagctgg agtgcagtgg   31620
tgtgatcatg gctcactgca gccttgactt cctgggctca agggagtctc ccacctcacc   31680
ctcccaagta gctgggacca ccggcatgga ccaccatgcc aggctaattt ttaaaatttc   31740
tgtagagaca gggtctcact atgttgttgt attagcccgt tctcatgctg ctataaagaa   31800
ctgcccaaga ctggataatt tataaaggaa agaggcttaa ttgactcaca gttccgcagg   31860
gctggggagg catcaggaaa cttacaatca ttgtggaagg ggaagcaaac atgtccttct   31920
tcacatggtg gtaggaagaa gaagtgccaa gcaaaggggg aaaagcccc ttatagaatc    31980 atcagatctc ttgaggactc actcactatc atgaaaacag catgagggta actgccccca   32040
tgattaaatt accttttcaca gggtccctcc catgatacat ggggattatg ggaactacaa   32100
ttcaaggtga gatttaggtg tggacacaga gccaaaccat atcagttgcc caggctggta   32160
ctgaactgct aggcttcagc aatcctcctg cctcagcctc tggagtagct gggaccacag   32220
gtgtaagtca ccaggcccag ctaattttta gcatttctat agagatggga tctcactgtg   32280
ttgcccaggc ttgcctcaaa cgcctgggct caggtgatcc cctccttgg tctcccaaat    32340 tgctgggatt acaggcgtga gcctgcgcct ggcctcctct aggatttta aagcatctta    32400 tgaatctaaa aacttctcac attcaggatt ccacaaacta ggtatccttc aggcttgaga   32460
ttctgcttct gcgatggatc ccagggaata tccaaggacc tatttgctgc ccttgggtgt   32520
cgctgggcag gactctgcct gcatccccca ccccccaatt tctacgtcct gcaccctacc   32580
cccaccccca gcaagcctgg ctaggtctct gctccgccag daccctggat gaccgtcccc   32640
tgcccccagg tcagacagcc ctgcacatcg ccattgagcg tcgctgcaaa cactacgtgg   32700
aacttctcgt ggcccaggga gctgatgtcc acgcccaggc ccgtgggcgc ttcttccagc   32760
ccaaggatga ggggggctac ttctactttg gtaaggaggg gcctggtggg ggctgacagc   32820
atgctggaga agcatggcgg gagatagcat gatactggtt ggtgtctgca gccctgacca   32880
tcacccagac acccagggcc actctggcca tgagcgcagg cagcactctg gaccacaggc   32940
tgcacgttgg tcttggtcac agggccgttg cctctgaggt gtaagtgcca tggggagtac   33000
catggacctg gattcagatc ctcactccag ccaggcacgg tgtctcacac ctgtcatccc   33060
```

```
agcactttgg gaggtcaagg caggaggatc gcttgagggc aggagtttga gaccagccta   33120
ggcaacatag caatacgctg tctcttttaa acatttaaaa aatggctggg cacggtggct   33180
catgcctgta atcccagcac tttgggagga tgaggcaggt ggatcacctg aggtcaagag   33240
ttcaagacca gcctggccaa caagatggtg aaacccatct ctacaaaaat aacaaaaatt   33300
agccgggcat ggtggtgggt gcctgtaatc ccagctactt gggaggctga ggcaggagaa   33360
ttgcttgaac ctgggggaca gaggttgcaa tgagccgaga tttccccatt gcactccagc   33420
ttgggtgaca gagtgagact ctgtctcaaa aataaataa ataaataaat aaataaataa    33480
gttagatggc atggtggcat gtgcttgaag tcccagctgc ttgggaggcc gaggctggag   33540
gatcacttga acctaggagt tcgaggctgc agtaagccat gattgcacca ctgcactcca   33600
gcctggaaaa tagagcaaga ccccgtcttt aaaaagcaaa agaaaagaa caaaaaaaa     33660
gccaaatcct cactctgcac tttccaggca tgtgacctca cttccctgag cctcaccttc   33720
cccagctgtg cagtggggat cacgagaggc ccttgggctg tgatgtcagc gcccagctct   33780
gtattgtctg tgtgctttaa tctggtttat gctgggacca acagccccat caccaggccc   33840
aaagcccacc actgccgttg tcatcactgg actcatgaaa tattttgaat tttgcccctg   33900
cttaaaggca ttcattatgt gcagctcagg acaaagtca cacaagaat tccatcatca     33960
gctgggcgcg gtggctcacg cctgtaatcc cagcactttg ggaggccgag gtcggcggat   34020
cacttgaggt caggagtttg agaccagcct ggccaacatg gcgaaatcct gcctctacta   34080
aaaatacaaa aattagccag gtgtggtggc gtgcgcctgt aatcccagct actcggctga   34140
ggcacaagaa ctgcttgcac ccgggaggtg gaggttgcaa tgagccgaga ttgtgccact   34200
gcactccagc ctaggcgaca gagtgagact ttgtctcaaa aaaaaaaaaa aaagaattc    34260
catcattgga tgtgtccagt ccctcacagc ctccaaatcg cgtggctgtg cccttaacta   34320
gccacacccc atctccctgg catcacccag agaaacgtgc agttcatatc cactgctggt   34380
gctgtctccg tcattatcct cagagcgcca cggtgtccgt cccccgagtg tctgcaggca   34440
gagtcccacc ctgggccccc ttcgctgacc tcccaccctt caccctggcc cgcaggggag   34500
ctgcccctgt cgctggctgc ctgcaccaac cagccccaca ttgtcaacta cctgacggag   34560
aaccccaca agaaggcgga catgcggcgc caggactcgc gaggcaacac agtgctgcat   34620
gcgctggtgg ccattgctga caacccccgt gagaacacca gtttgttac caagatgtac     34680
gacctgctgc tgctcaagtg tgcccgcctc ttccccgaca gcaacctgga ggccgtgctc   34740
aacaacgacg gcctctcgcc cctcatgatg gctgccaaga cgggcaagat tggggtgagt   34800
gtgcggctgg gggcacagct gatccaccta ctcgtacccc tctgcacaca cacgcagggg   34860
tctgctgctg gtattcatta ttaatacgtg catgcacctc caacatgcc aaccccagtg     34920
tgcagatgtc ccagctcaag aacctgctat ggctccctag tgtccagcca agctccttag   34980
cttcatcccc gagcctctcg cctcatgtca ccctactgga tgttcaccac tccacccca     35040
ccagccagga tgagccactg ataagaaact gagtccccgg gccctagccc agcggtgctc   35100
ccagcctcaa acctgttgaa tggccctgcc ccagttcctt ccctttctg ggccgcgcag     35160
catgggcct ggagaagggt ttctcaactt cagcatgatt attttgggcg gcaggctctt     35220
tgtggtgggg accgtcttgt gctattgcca gacattgatc tgcatcccgg gcctctaccc   35280
accagatgcc aggaacacct cccccttacac ttgtgaccac caaaaatatc tccagaacat   35340
tgctgaattg tcctctgggg ggcaccatcg ctggattggg aaccaagtct ggagtatgct   35400
agaggcagga gcacctgtcc aagccctggc gctaccactt cccagtgtgt gacctcagac   35460
```

```
atctcatttc cctttctgt gcctcagttt ccttgtctgt aaaatgggga tataagagtg    35520
tcctctggtg tggtgttgtg acaaatgcgg tgatccacat aaggctctta ggaaggagcc    35580
tgggagaagc agtaagtgtc acttacatgt ctgtaatgcc agctagttgg gaggctgagg    35640
tgagaggatc gtttaagtcc agcctggatt atttgagatc ccaaataaat aaaaaccaaa    35700
ataaaaaaaa atgtagcaaa aattactaaa attgcaatta taccatggcc ctgaggcagt    35760
agaaaggctc cagtttaaat cctggctttg gctaggctca gtggctcgtg tctgtaatcc    35820
tagcactttg ggaggctgag gtgggaggag cacttgagcc caggaggttg aggctgcaat    35880
gagctgtgat agtgccattg cactccagcc tgggcaacag agccagaccc tgtctcaaaa    35940
aaccccaaaa tcctggctgt gcacagtggc tcatgcctgt aatcccagca ctttgggagg    36000
ccgaggtggg cggatcacct gaggtcagga gttcaagacc agcctggcca acatggtgaa    36060
accccgtctc tactaaaaat acaaaaatat tagctgggtg tgatagtggg cacctgtaat    36120
cccagctact caggaggctg aggcaggaga attgcttgaa cctaggagga gagggttgca    36180
gtgtgctgag atcgcgccac tgcactccag cctgggtgac agagagagac tctgtctcaa    36240
aacaaaaacc ccaaaatcct aacattgcct gaccttgggc aattcccacc cctctctgtg    36300
cctccgcttc cctgtgtgta agccagggaa ggaggagtgg taacaggaag gaccgcatgt    36360
gatcgtcagt attataattc acatgtcatt aagatggatt cattgctatt ttaacggcat    36420
gaagaagata ttcattacaa ttaagatgtt gaaggctcat ccaggttctg tctggctcca    36480
gctgactggt taagtggctt ctggaacacc cttcgttttt cccagcctcc attctttatc    36540
tgtaaaccaa gataataaga gcaagaatta aacaagatga ggaaagggtc ctccagcagc    36600
cggtgcttag ctgttttctg gggaggcgtc atgtgctgag ctgggcccag ccctgggggt    36660 cttttccagtg tgagcccct gaccctcctg gcccctgtg cagatctttc agcacatcat    36720
ccggcgggag gtgacggatg aggacacacg gcacctgtcc cgcaagttca aggactgggc    36780
ctatgggcca gtgtattcct cgctttatga cctctcctcc ctggacacgt gtggggaaga    36840
ggcctccgtg ctggagatcc tggtgtacaa cagcaagatt gaggtgggct ccaggagggg    36900
gcatggggtg tgaggaagga gggggcagggc tgggagtagg gacagggccc tggggctggg    36960
ctggggagga cagccccagc ctctaggacc caacgtggtg ggtctgttgg ctgaatgcaa    37020
gagaaggtgc caactaagtg cccagaacag tgtctgccat gtgaggaaat gagcaagact    37080
tgtgggaaga tggacttttg gggcaggtag gactgggttg ggatcctggc tctgtaactt    37140
acatgctgtg tgtctcagga caagtggctc cacctctctg ggtctcagct tcttcatttg    37200
taacctgggg ataaggatca tggatatccc atggggttct tgggaggacc aaagaggtta    37260
attttagaat ggcttggcac agagtaaaca ttatgtcagc ttttactact catggttgtt    37320
atatgaactt ttgaaaagctc ttttttttcg gtcaggcatg gtggcttatg cctgtaattc    37380
tagcattttg gggagccaag gtgggcggat gcttgaagc caggagtttg agactagcct    37440
gggcaatatg gcgaaacccc gtctctacca aaaaaaaata ataaaaatga aaattagcta    37500
ggcatggtgg tgcgagcctg tagtcccagc tacttgggag gcgaggtggg aggatcacct    37560
gagcctgggg aggtcgaggc ttcagtgagc cgagatcatg ccactgcact ccagcctggg    37620
tgacagagtg agatcctgtc tcaaaataaa caaacaaaca aacaaacaaa aaaccaagct    37680 ttttttccc tacttagcag tattttgtga acgtcgttct gtactttaa atattctttg    37740 gtaatattgt cgctgcatgt aaacatacca tattcaaatg aactgttctc ttattgctgg    37800
```

```
tcgcttgggt tgtttctgc ctttatcagg aataacacta taagagcatc tctgtggctg   37860
ctttattgca caaatcatga ttatagagaa actcaagtta ataaagggct aggaagctat   37920
aaaaatggag cagaaaatgc tggggactgg gtgcaggtgg tcttccttct agccctgccc   37980
tgtggcttac tggtctgtga gcttggcttc cttgcaagac ctcatttccc tcattttttg   38040
aattagtgac catcttgatt taaattagtg gtggcaggag gtttagcatc tcaggtgcaa   38100
actgattgat tagtagtgtc tacccaggga actgtatgaa tacaattgtg cagggctcaa   38160
ttattgatgt ctgccctggg ttcagaattg gagaattgtg gtgagtcaat catttatcat   38220
ctttgggcaa aatttctcaa tctttctctc tgaatcagaa tttctgagag cggaggccag   38280
gatttatact tgcagcaagt tacataaatt attttgcggc cagcagcttg gtactatcca   38340
cagattggag tttgggaacc atgagaataa atgtcttttt ttcttttttg agatggagtc   38400
tcactcttgt tgcccaggct ggagtgcagt agtgcgatct aggctcactg caatctccgc   38460
ctcccaggtt caagtgattc tcctgcctca gccttaggag tagctgggat tacaggtgtg   38520
caccaccacg cccggctaat tgttgtgttt ttagtgagga cagggtttca ccacattggc   38580
caggctgatc ttgaactgct gaccttaggt gatccgcctg tcttggcctc ccaaagtgct   38640
aggattacag gcatgagcca ctgcggccgg cctgaaaata aatgtctttt aagggacttt   38700
ccagttccga gttctgtgat gctagaatag ggtggaaagg tacattgagg cagaattggg   38760
cagctgaatc cattcatgaa tccgtgaatg cagctgagga atggatggaa agagaaagcg   38820
ctgtccgggt ggagggtggg ggaaggcaca cccgaggcag cctgcctgga ccccccaccc   38880
atctcaggaa ggcagccccc gaccaccctg cctctcttag aaccgccacg agatgctggc   38940
tgtggagccc atcaatgaac tgctgcggga caagtggcgc aagttcgggg ccgtctcctt   39000
ctacatcaac gtggtctcct acctgtgtgc catggtcatc ttcactctca ccgcctacta   39060
ccagccgctg gagggcacag tgagtgcccg gggaccgggc aggggctggg gcaggcactg   39120
ggctgagcca tgcaggactg gggcacaacc tcatccttct gggtcccctg taggggacc   39180 cggagaaggt ttaggaacag gttggggagg cgccctccag catccacggg tggccctgag   39240
ctgggaggag gaagactcag gaggaagaga gtgaaggagg aggctccatg ggatgccgat   39300
gtttcgggcc tggggggaaca tctggattgg gggccagatg ttggagggc tgggtgacga   39360 cctgtgtgcc cttgctgctc cccagccgcc gtacccttac cgcaccacgg tggactacct   39420
gcggctggct ggcgaggtca ttacgctctt cactgggggtc ctgttcttct tcaccaacgt   39480
aagtgcctgg cccccgtgcc cccacccctg cctgccctcc tcttctcttc ctgcacctct   39540
tttctctccc tcttttttctc ttctctctcc tccaaatggt ccttctcctt ccttcctcc   39600 ttttattttc ccattttctct tctacctcct ccaatcccac gttctccatc tctgcttttt   39660
tctccttttc taacaggaaa gagtcctttg tcttttctct gtaccagcct ctgcctccct   39720
ctcttctatc ccttttctctg tctcctctct cctcctctcc tctcctgctg gcccaccc   39780 tttcacgtgc cccctcctgt cttccagatc aaagacttgt tcatgaagaa atgccctgga   39840
gtgaattctc tcttcattga tggctccttc cagctgctct agtgagtaga ggtccctggg   39900
ccggcagctt ctgggtgagg aaggtgggtt tgggctgcta ggtcgtccag attcaggaga   39960
gaggtgattc tgttagaaat gaatgcaccc aacctgggca gctctaaccc aaagtcagga   40020
caaagccaca aacaataggg tcttctggtt caagaaaaat tctgattgct agggagttat   40080
catatacaac atggatagaa ataattttaa cctcttatgc tggtgaatga ttgctaatgt   40140
ctgcctgaag tgccatgtta agaattttgc acctgtgtct gtgtttagtg ggaaagagtt   40200
```

```
gggattgatt aatgatgtct gcctgggaca gagaatgaga gagttactga gtgtgtgtta   40260
cctctttcac atttccctta gagttggaga atgatgaaat tcacttagcc acaaaatctc   40320
cactgaacac cactaaatct ttctttagca attccaaggg gcatcacttc aggatcctgt   40380
gggacctcag gattaattgc cagctaattg aatgttcttg ttaacagaat gctggggaac   40440
cctgctaatc cactttgttt cttttctggg ggtctagaag gcattgggaa gtcctgatac   40500
cctggagggc ttggaggcgt gtcttcccct ccagagcctc attgtcccct ctccctctg    40560
gcctctcttg tggtctctgc tgcactgcag cttcatctac tctgtcctgg tgatcgtctc   40620
agcagccctc tacctggcag ggatcgaggc ctacctggcc gtgatggtct ttgccctggt   40680
cctgggctgg atgaatgccc tttacttcac ccgtgggctg aagctgacgg ggacctatag   40740
catcatgatc cagaaggtac gggctgggag gaccctctgg actcgtgtgt tcctggaggg   40800
agtcacacac acaccacatg cacacttatg cacctgcaga cctgaggatg ctgggtaccg   40860
tgggggcagg aggcatggtc tggacactgg ggtgggacca gggtggagat ggaggaatgg   40920
ggaaagtgag aaaccatgtg tctcctcttt gcctccataa tcccgctggg gtctttagat   40980
tctcttcaag gacctttttcc gattcctgct cgtctacttg ctcttcatga tcggctacgc   41040
ttcaggtgag ctctgggtgc tcaggtggtc ctggcagggg tggtgcaagg acgggaacag   41100
tagccatgat gtataggga caatagcagc cttgctgagt tctttttttt tttttttttt    41160
ttttgaggtg gagttttgct cctgttgccc gggctggagt gcaatggcac aatctcagct   41220
cactgtaacc tccacctccc aggttcaagt aattctgcct cagcctccca cgtagttggg   41280
attacgggct cctgccacca cgccccacta tttttaatt ttttttttt tgtattttta     41340
gtagagatgg ggtttcacca tgttggccat gctggtcttg aactcctgac ctcaggtgat   41400
ccaccctcct tggcctccca aaatggtggg attacaggtg tgagccaacg cgcctggcca   41460
ctgagttctt atttgtgtgc caggcaccag actaagtacg tttccatcct tgcctcccaa   41520
caagcctgta agctaagtgc ctttattatc ccctattata gaaaaggaaa ctgaggctta   41580
ggagggttaa ataactagca caagttcaaa agccagtgaa tggtggccgg gcgcagtggc   41640
tcacatctgt aatcccagca cttcaggagg ctgaggcggg tagatcactt gaggtcagga   41700
gtttgagacc agcctggcca acatggcaaa accccgtctc taccaaaaaa tacaaaaatt   41760
agacaggcat ggtggcgcgc aactatagac ccagctactc gggaggctga ggcacaagaa   41820
tcgcttgaac ccaggggggtg gaggttgcag taagccaaga tggcaccact gcactccagc   41880
ctgggcaaca cagcgagact ctgtctcaaa aaaaaaaaa aaaaaaaagc tggtgaatgg   41940
caaaactgga gtattagcta ttgctacaaa ggaagccacc taaagtgggg cttaaaatag   42000
cacccactta ttattattat tttttttgtg gcaaggtctc actctgtcac caaggctgga   42060
gggcagtggt gctcttggct cactgcaatc tctgcctcct gggttcaagc gattctcttg   42120
cctcagcctc tcgaatagct gggattacag gcgtgtgcca ccacgcatgg ctaagtttta   42180
tattttggt agagatgggg tttcactatg ttggccaggc tggtctcgaa ctcctgaccc   42240
caagtgatcc acccaccttg gcctcccaaa gtgctgggat tacaggcgtg agccactgta   42300
ccaggccaac ttactattgc ttatgagtca atgggtcagc tgggtggctg tgctgccctg   42360
ggccaggttt ggctgatccc tacaggctct tgtgcctgtg gtcagctggc aggctggctg   42420
ctggctgact ggtctagcta gtatggactt ggttagaggg ggtttgctat ctatcttcca   42480
catggtcact catttctgga cagctagctt gggcttgtcc acatggtggc cttagggttc   42540
```

```
caagaacatg agcagaagtg ttcaaggaca cctcctggca tggcatcact gctgccttac   42600
tctgttggcc aaagcaagtc acaaggccag cctcgattca agggatgggg aaatagacgc   42660
cacttctttt tttccatttt ttttttttgg tggaggcagg gtcttgctat gttgcccagg   42720
ctggtcttga actcctgggc tcaagcagtc ctcctgcctc agcctcccaa agtgcaggat   42780
tataggcgcg agccactgca cctggcctag actccacttc ttagtgggag aagctgtaaa   42840
gccacattga aggaggatgg atacatggaa ggataaaatt taataattaa actagcagcc   42900
caggtatttt cttaaagccc aacatcagct cccttgatat accttcttcg tgatgtcatg   42960
atgccactaa gaagcattct gggacctcag tggcatgggt catgggagaa ggaccaggga   43020
ccagggctgg agaaactgac caagtccttg ggctgatccc cgaggtgtgg gtaatctgac   43080
atcaatgccc agcatccaaa ggggaatggc caactcaggt tagacctgga cacatacaca   43140
tctgagcagg ttcatctggg gacgagcctg gcacaggaat ctgacaaggg tgatattta   43200 acccacgata gtggccaagt ctctaggtag attattggtg ggaagtggaa ttgtagtttt   43260
cactggggag atagggacag ggtacagctt tcccttccca gggatcacac tggacaaact   43320
agacagtgtc aagggttcaa caacagtttg ggattcaggt cagggatcta gccctactgc   43380
agtcctagtt attgaaacta aggagaaaca agggttagag tagcagctta gcagtcagct   43440
tggttgcagg tcttctcctt ataggatgca ctagatctca attctgaggc tgacatgaca   43500
taaacaggac acacatgctt ctgttcccac actttggtgt ccatagcaga catcactaat   43560
ggatcacaga acagttttc cggtgagtcc agacaaggtc tcagaatcct tctcaacaca   43620
gtgtttcacc aggtactata caactgaaga acattagcat atgagttgaa atctgcatac   43680
tctaatccct ggttgcaggc agtatgacat tctgtgcccc actgactgat gggactgagt   43740
cttcttcatg ctcccctccc tggctggttt agggacaggt tgttgctgcc aaactgtgtt   43800
gagaaggaat ctgaagctcc acctgggctt agtaggaaag gagaaccatg atgagtttga   43860
gatgtctaga gcaggagagg ccccttagag aacacggctt tggggacagt caggactgat   43920
gcctggtttc agcccccact tttcctctct gggttgggt ggagtgggaa actgtcagag   43980
agagagtcta cccctgcgaa tagggcatt ccagagcccc caagacctct aagaatggta   44040
ggccgcatta ggatttccca acactattga catttgagac cagatcattc ttcgtggcgg   44100
ggaccatcct gtgcattgta gggtgtcagg cagcacccct ggcctccacc cacctgatgc   44160
cagtagcacc cccacccca gttgtaacaa ccaaatatgt ctctagacat tgtcaaatgt   44220
cccctggtgg gaaaaactga gaccctccct ggactagatc ctgaaaacct tttccctccc   44280
ggtagcaggg aaccaccagg ttgtgtaagg aggggtgaac tgtcccaggt tggaaacaga   44340
gcaggtcaaa actcctacgc ttatcagtag tgggattgag cctgtgagta gccactgcac   44400
tccagcctgg gcaacatagc aagacccat ctcagaaaga aagagagaga gagagagata   44460
acctcttcct tatcgcaag agtttatgga aaggcttcaa aggttttggg atcaggagga   44520
cctgggtctg gtgtggcttg gctgatgtgt agggtgacat gggtcagcgt gtgggccagc   44580
gtgctccgct cactaggcct cagctttctc ctccagcaaa tgagaatgac ccctccacc   44640 tctctgtggg tgtgctcaca ctcagtgagt gccaccccta tcctcccaca gccctggtct   44700
ccctcctgaa cccgtgtgcc aacatgaagg tgtgcaatga ggaccagacc aactgcacag   44760
tgcccactta cccctcgtgc cgtgacagcg agacttcag caccttcctc ctggacctgt   44820
ttaagctgac catcggcatg ggcgacctgg agatgctgag cagcaccaag taccccgtgg   44880
tcttcatcat cctgctggtg acctacatca tcctcacctt tgtgctgctc ctcaacatgc   44940
```

```
tcattgccct catgggcgag acagtgggcc aggtctccaa ggagagcaag cacatctgga   45000
agctgcaggt gaggccccag ggcccccagc cccactctac cagccaccct cgtccttccg   45060
aggagaccca cccgactggc ttcctcggcc ttccactctg agcaagcagt gtcttctcat   45120
tctccctcca cttctctgtc ggtaaaatgg gcatcagagg ctgctgctga cttcccagag   45180
ctgcctagtg aattttgagg tggcttcttg cctggctgcc agcagtgggc tcagattctc   45240
cttgtggtcc agctcacagg acacagtcgg ctccacctag catgactgag tgacttctgc   45300
cggctcagaa agtgctccgt gggcatcagc gtttcagcag gggtcccacg ctgagcccag   45360
gggcagcttt tgtgctctag cactccagca cagggatgtc agcattctca tgggggtctt   45420
tttctagcaa ctgtgagcat gcttcctaga ggagaaacca atggggacag ggccgcctt   45480 ggcccgggga gctgcagaaa gtttttactt accaaaagct ttctatgcaa tcctggaaag   45540
aacaggccct gggatcacag ccctcccagg ccaggtgcag cctacaaacc tggtgtccta   45600
ataaacagtg ctgccccacg gcccaggaat acagcacccg tgtttacctt gactgtgcat   45660
ttcaggaaaa tggtgcagtg agaaaaaagg gcccaaggtt gtcctcccag gactgggtct   45720
gagggaaaca gctctggcct gctcttaacc tttatctata ttgcttactt cattgggcct   45780
cagtttcccc actgggcatt actcacagga tgcaaactgg gcatcctgtg ggctggagtg   45840
caatggtgtg atcttggctc actgcaacct ctgcctccca ggctcaagtg attctctgtc   45900
ctcagcctcc cgagtagctg gggctaaggt gtgcaccacc tcacccggct aatttttgta   45960

ttttttgtaa agatggggtt tcaccatgtt gcccaggctg gtcttgaact tctgagttca   46020
agctatccac ctgccttggc ctcctaaagt gctgagattg caggtgtgag ccactgcacc   46080
cagcatcaga ccattatatt aaaaacaaca acaacaacaa aaactgcaa aattaaaaa   46140

ttaagagatt ccctatgaaa acccagattt ctggcttttc ttgaaaagtt ggaagctcca   46200
ggcagtgcag gtccggatt cctgcctggc agccctcagg tggggtgagt ggcagctgcc   46260
cccttacacg tgggcatttg ctccctgttc tccccagtct ctacccctcc ctcactgaga   46320
ggcaactgct gtgtaagtgt gatagggctt gggcggcagc ctttctgcac ctgatcctgt   46380

ttcacccatt tgtttcctg cctgccacct gtgggtattt gagtttataa accctgtgtc   46440
tagtggggag taggagtcta aatgcctagt tctgggccca ccctggcccg ttgtctcatt   46500
tctgccacca gagcggcagg cgcaggctgt gaggctcacc gatgtccctc ctgaccctcc   46560
ctccccgcag tgggccacca ccatcctgga cattgagcgc tccttccccg tattcctgag   46620
gaaggccttc cgctctgggg agatggtcac cgtgggcaag agctcggacg gcactcctga   46680
ccgcaggtgg tgcttcaggt gaggctgggg cagtggggcc aggatggcag ggcggaactg   46740

tccccactgg ctcggggccc ctgctgctcc agcgtcgtct acccattgca atttctggag   46800
ccactgaggc cccaagaggc ccgagcagag ttcatttcca ccaggcgatc tcaggcaagt   46860
cagcccacct ctctcagcct cagtttcttc atctgtggaa tgagacaatg atctcacggg   46920
ctcctaggct ggcggtgcgg attagacagg tcagcacgtg agaagtgctc agccagtgcc   46980
cgacgcgcat cgggacgcca caggctcccc tgttcttgct caggggggaag cagagacttg   47040 gatggtgggt tcattttaga gcatcaccct gtatctacca aacagtgggg tgagctctag   47100
tgccctcggt gaaatgggaa gctgaggaat gtgcagtttc cagggctgga gacctcaccc   47160
agcccatctg cagaatgact ccgtgttcca gaggcacagg gagtgccagc ttcttagggg   47220
aaccccttca tgaatctttt ctttccagtt gattcattca ttgtaaagtg gttgtcagca   47280
```

```
tggagcataa gcagaatgtt tggagtcaga caaagtcagt ttcttcatct gtgaaatggg    47340
aacaataata gaacccacct cctaggccat ccgatcagtt caattccatt ttttgtttgt    47400
ttttagaggc agggttgctc aggctggagt gcagtggtgt gatcatagct gactgcagcc    47460
tccaactcct ggtctcaagc gatcctccca cctcagcctc ctcatgccac catgtccgac    47520
caatttttaa ttttttttgta gagatggggt tcttgctatg ttgcccaggc tggtctcaaa    47580
ctcctggtct caagcgatct cccacctca gcctcccaaa atgctgggat tacaggcgtg    47640
agccaccaca cccagcctct gttcagtttg aatccaaagc tcaaatcttg gctgggtgtg    47700
gtggctcgtg cttgtaatcc cagcacttg ggaggccaag gtgggtggat cacctgaggt    47760
caggagtttg agaccaccct gggcaacatg gtgaaaccct gtctccacta aaaatacaaa    47820
aattagtcgg gagtggtggc atgcacctgt aatcccagct actcgggagg ctgaggcagg    47880
agaatcgctt gaacctggta ggtggaggtt gcagtgagcc gagattgcac tactgcactc    47940
cagtctggcg gacagagcaa gactctgcct taaacaaac aaacaaaaat gaatagatag    48000
gataaaaaat taaagataat atgtaaaaaa aaagataat atataaaaaa atgagtggat    48060
aaacaaaatg tgggctatgt gtacagtgaa atattatctg gccaggcgt ggtgactgta    48120 ataccaacac tttgggaagc gaggcaagag gattgcttga gcccaggagt tcaagaccaa    48180
catagtgaaa ccccatctct acaaaacgtt tttaaaaaat tagccaggtg tggtggcata    48240
tccctgtaat cccagctaca tgggggcctg aagtgggcgg atcacttgag cctgggaggt    48300
caaggttgca gtgagctgtg atcgtgccac tgcaccctag cctgggcaat ggagtgagac    48360
cctgtctcaa aagaaggtta aaaaaataa tttctgcttg ggggaatgga agaattttgg    48420
aaatagatag ctgtgatggt cacacaatgt ggatgtgctt aatgccactg aattgtatac    48480
tcaaaaatga ttaagatggc aaattttttg tgtgtgtata cacacacaca cacacacaca    48540
cacacacgtc ttttttttt ttttttgag atggagtctt gctttgtccc ccaggttgga    48600
gtgcagtggc gtgatctcgg ctcactgcaa ctgcctccca ggttcaagtg attttcctgc    48660
ctcagcctct cgggtcactg ggactatagg cacccgccac catgcccgc taatttttt    48720 tttaatttt tttaatttt agtagaggtg gggtttcacc atgttggcca ggctggtctc    48780
gaactcctga cctcaaatga cccacccacc tcggcctccc aaagtgctgg gattgcaggc    48840
atgagccacc acgcccagcc ttgttatgta tatgttacca taataaaaaa ataggagggt    48900
gtgctgggga tggtggcatg gagagcgtct ctgaggggtt cccatgacc ctctgcttgg    48960 gccctgccag ggtggatgag gtgaactggt ctcactggaa ccagaacttg gcatcatca    49020 acgaggaccc gggcaagaat gagacctacc agtattatgg cttctcgcat accgtgggcc    49080
gcctccgcag gggtgagtgg aggggcgggt gcggagggga gccccagtcc attctcatca    49140
cgaatttgct ttgagcagtc ctgcttcttt ccgggactca gtgtccgtgt ctacagaatg    49200
agagagtgtg ccccctgagct tcctctgctg cttgtgaatg cctggggcac ctcacctacg    49260
tggcttcatc ctggccctcc ctactgttga cataagctgg cctggggagg gaggacgagc    49320
tcctcagcca tccctgtgtg gagaaaacct tcctgtttgt ccagtaagcc atgagcacgc    49380
gagacgcagc tggagaggac acaggcactc agggcattcg gctccaggct tgaatcctgg    49440
ttcctccatt ctctcctggg gaggcacctt gacctctctt gagccccagt ttccacctct    49500
gtaaaatgag catagtcaca tccccccttc agaacactgt ggagtgccca gtacacagta    49560
ggcactcaat atacgcacgc tctctctcca ccaaccccca cccctccctc tgatgtgctc    49620
tcggtgcaga tcgctggtcc tcggtggtac cccgcgtggt ggaactgaac aagaactcga    49680
```

```
acccggacga ggtggtggtg cctctggaca gcatggggaa ccccgctgc gatggccacc    49740 agcagggtta cccccgcaag tggaggactg atgacgcccc gctctaggga ctgcagccca   49800
gccccagctt ctctgcccac tcatttctag tccagccgca tttcagcagt gccttctggg   49860
gtgtcccccc acaccctgct ttggcccag aggcgaggga ccagtggagg tgccagggag    49920
gccccaggac cctgtggtcc cctggctctg cctccccacc ctggggtggg ggctcccggc   49980
cacctgtctt gctcctatgg agtcacataa gccaacgcca gagcccctcc acctcaggcc   50040
ccagcccctg cctctccatt atttatttgc tctgctctca ggaagcgacg tgacccctgc    50100
cccagctgga acctggcaga ggccttagga ccccgttcca agtgcactgc ccggccaagc    50160
cccagcctca gctgcgcct gagctgcatg cgccaccatt tttggcagcg tggcagcttt    50220
gcaaggggct ggggcccctcg gcgtggggcc atgccttctg tgtgttctgt agtgtctggg   50280
atttgccggt gctcaataaa tgtttattca ttgacggtg                           50319
```

```
<210> SEQ ID NO 4
<211> LENGTH: 3254
<212> TYPE: DNA
<213> ORGANISM: Homo sapiens

<400> SEQUENCE: 4
ccggccggga ttcaggaagc gcggatctcc cggccgccgg cgcccagccg tcccggaggc     60
tgagcagtgc agacgggcct ggggcaggca tggcggattc cagcgaaggc ccccgcgcgg    120 ggcccggga ggtggctgag ctccccgggg atgagagtgg caccccaggt ggggaggctt     180
ttcctctctc ctccctggcc aatctgtttg aggggagga tggctcccct tcgccctcac    240
cggctgatgc cagtcgccct gctggcccag gcgatgggcg accaaatctg cgcatgaagt    300
tccagggcgc cttccgcaag ggggtgccca accccatcga tctgctggag tccaccctat    360
atgagtcctc ggtggtgcct gggcccaaga aagcacccat ggactcactg tttgactacg    420
gcacctatcg tcaccactcc agtgacaaca agaggtggag gaagaagatc atagagaagc    480
agccgcagag ccccaaagcc cctgcccctc agccgccccc catcctcaaa gtcttcaacc    540
ggcctatcct ctttgacatc gtgtcccggg gctccactgc tgacctggac gggctgctcc    600
cattcttgct gacccacaag aaacgcctaa ctgatgagga gtttcgagag ccatctacgg    660
ggaagacctg cctgcccaag gccttgctga acctgagcaa tggccgcaac gacaccatcc    720
ctgtgctgct ggacatcgcg gagcgcaccg gcaacatgcg ggagttcatt aactcgccct    780
tccgtgacat ctactatcga ggtcagacag ccctgcacat cgccattgag cgtcgctgca    840
aacactacgt ggaacttctc gtggcccagg gagctgatgt ccacgcccag gcccgtgggc    900
gcttcttcca gcccaaggat gagggggggct acttctactt ggggagctg ccctgtcgc    960 tggctgcctg caccaaccag ccccacattg tcaactacct gacggagaac cccacaaga   1020 aggcggacat cgcgccag gactcgcgag gcaacacagt gctgcatgcg ctggtggcca    1080
ttgctgacaa cacccgtgag aacaccaagt tgttaccaa gatgtacgac ctgctgctgc    1140
tcaagtgtgc ccgcctcttc cccgacagca acctggaggc cgtgctcaac aacgacggcc    1200 tctcgccct catgatggct gccaagacgg gcaagattgg gatctttcag cacatcatcc    1260
ggcgggaggt gacggatgag gacacacggc acctgtcccg caagttcaag gactgggcct    1320
atgggccagt gtattcctcg ctttatgacc tctcctccct ggacacgtgt ggggaagagg    1380
cctccgtgct ggagatcctg gtgtacaaca gcaagattga gaaccgccac gagatgctgg    1440
```

```
ctgtggagcc catcaatgaa ctgctgcggg acaagtggcg caagttcggg gccgtctcct    1500
tctacatcaa cgtggtctcc tacctgtgtg ccatggtcat cttcactctc accgcctact    1560
accagccgct ggagggcaca ccgccgtacc cttaccgcac cacggtggac tacctgcggc    1620
tggctggcga ggtcattacg ctcttcactg gggtcctgtt cttcttcacc aacatcaaag    1680
acttgttcat gaagaaatgc cctggagtga attctctctt cattgatggc tccttccagc    1740
tgctctactt catctactct gtcctggtga tcgtctcagc agccctctac ctggcaggga    1800
tcgaggccta cctggccgtg atggtctttg ccctggtcct gggctggatg aatgcccttt    1860
acttcacccg tgggctgaag ctgacgggga cctatagcat catgatccag aagattctct    1920
tcaaggacct tttccgattc ctgctcgtct acttgctctt catgatcggc tacgcttcag    1980
ccctggtctc cctcctgaac ccgtgtgcca acatgaaggt gtgcaatgag accagacca    2040 actgcacagt gcccacttac ccctcgtgcc gtgacagcga accttcagc accttcctcc    2100 tggacctgtt taagctgacc atcggcatgg gcgacctgga gatgctgagc agcaccaagt    2160
accccgtggt cttcatcatc ctgctggtga cctacatcat cctcaccttt gtgctgctcc    2220
tcaacatgct cattgccctc atgggcgaga cagtgggcca ggtctccaag gagagcaagc    2280
acatctggaa gctgcagtgg gccaccacca tcctggacat tgagcgctcc ttccccgtat    2340
tcctgaggaa ggccttccgc tctggggaga tggtcaccgt gggcaagagc tcggacggca    2400
ctcctgaccg caggtggtgc ttcagggtgg atgaggtgaa ctggtctcac tggaaccaga    2460
acttgggcat catcaacgag gacccgggca agaatgagac ctaccagtat tatggcttct    2520
cgcataccgt gggccgcctc cgcagggatc gctggtcctc ggtggtaccc cgcgtggtgg    2580
aactgaacaa gaactcgaac ccggacgagg tggtggtgcc tctggacagc atggggaacc    2640
cccgctgcga tggccaccag cagggttacc cccgcaagtg gaggactgat gacgccccgc    2700
tctagggact gcagcccagc cccagcttct ctgcccactc atttctagtc cagccgcatt    2760
tcagcagtgc cttctggggt gtcccccac acctgctttt ggcccagag gcagggacc    2820 agtggaggtg ccagggaggc cccaggaccc tgtggtcccc tggctctgcc tccccaccct    2880 ggggtgggg ctcccggcca cctgtcttgc tcctatggag tcacataagc caacgccaga    2940
gcccctccac ctcaggcccc agccctgcc tctccattat ttatttgctc tgctctcagg    3000
aagcgacgtg acccctgccc cagctggaac ctggcagagg ccttaggacc ccgttccaag    3060
tgcactgccc ggccaagccc cagcctcagc ctgcgcctga gctgcatgcg ccaccatttt    3120
tggcagcgtg gcagctttgc aaggggctgg ggccctcggc gtggggccat gccttctgtg    3180
tgttctgtag tgtctgggat ttgccggtgc tcaataaatg tttattcatt gacggtgaaa    3240
aaaaaaaaaa aaaa                                                     3254
```

<210> SEQ ID NO 5
<211> LENGTH: 3057
<212> TYPE: DNA
<213> ORGANISM: Homo sapiens

<400> SEQUENCE: 5

```
ccggccggga ttcaggaagc gcggatctcc cggccgccgg cgcccagccg tcccggaggc      60
tgagcagtgc agacgggcct ggggcaggca tggcggattc cagcgaaggc cccgcgcgg     120 ggcccgggga ggtggctgag ctccccgggg atgagagtgg caccccaggt ggggaggctt     180
ttcctctctc ctccctggcc aatctgtttg aggggaggga tggctccctt tcgccctcac     240
cggctgatgc cagtcgccct gctggcccag gcgatgggcg accaaatctg cgcatgaagt     300
```

```
tccagggcgc cttccgcaag ggggtgccca accccatcga tctgctggag tccaccctat    360
atgagtcctc ggtggtgcct gggcccaaga aagcacccat ggactcactg tttgactacg    420
gcacctatcg tcaccactcc agtgacaaca agaggtggag gaagaagatc atagagaagc    480
agccgcagag ccccaaagcc cctgcccctc agccgccccc catcctcaaa gtcttcaacc    540
ggcctatcct ctttgacatc gtgtcccggg gctccactgc tgacctggac gggctgctcc    600
cattcttgct gacccacaag aaacgcctaa ctgatgagga gtttcgagag ccatctacgg    660
ggaagacctg cctgcccaag gccttgctga acctgagcaa tggccgcaac gacaccatcc    720
ctgtgctgct ggacatcgcg gagcgcaccg gcaacatgcg ggagttcatt aactcgccct    780
tccgtgacat ctactatcga ggtcagacag ccctgcacat cgccattgag cgtcgctgca    840
aacactacgt ggaacttctc gtggcccagg agctgatgt  ccacgcccag gcccgtgggc    900
gcttcttcca gcccaaggat gagggggggct acttctactt tggggagctg cccctgtcgc    960
tggctgcctg caccaaccag ccccacattg tcaactacct gacggagaac ccccacaaga   1020
aggcggacat gcggcgccag gactcgcgag gcaacacagt gctgcatgcg ctggtggcca   1080
ttgctgacaa caccgtgag  aacaccaagt ttgttaccaa gatgtacgac ctgctgctgc   1140
tcaagtgtgc ccgcctcttc cccgacagca acctggaggc cgtgctcaac aacgacggcc   1200
tctcgcccct catgatggct gccaagacgg gcaagattgg gaaccgccac gagatgctgg   1260
ctgtggagcc catcaatgaa ctgctgcggg acaagtggcg caagttcggg gccgtctcct   1320
tctacatcaa cgtggtctcc tacctgtgtg ccatggtcat cttcactctc accgcctact   1380
accagccgct ggagggcaca ccgccgtacc cttaccgcac cacggtggac tacctgcggc   1440
tggctggcga ggtcattacg ctcttcactg gggtcctgtt cttcttcacc aacatcaaag   1500
acttgttcat gaagaaatgc cctggagtga attctctctt cattgatggc tccttccagc   1560
tgctctactt catctactct gtcctggtga tcgtctcagc agccctctac ctggcaggga   1620
tcgaggccta cctggccgtg atggtctttg ccctggtcct gggctggatg aatgccCttt   1680
acttcacccg tgggctgaag ctgacgggga cctatagcat catgatccag aagattctct   1740
tcaaggacct tttccgattc ctgctcgtct acttgctctt catgatcggc tacgcttcag   1800
ccctggtctc cctcctgaac ccgtgtgcca acatgaaggt gtgcaatgag gaccagacca   1860
actgcacagt gcccacttac ccctcgtgcc gtgacagcga accttcagc  accttcctcc   1920 tggacctgtt taagctgacc atcggcatgg gcgacctgga gatgctgagc agcaccaagt   1980
accccgtggt cttcatcatc ctgctggtga cctacatcat cctcaccttt gtgctgctcc   2040
tcaacatgct cattgccctc atgggcgaga cagtgggcca ggtctccaag gagagcaagc   2100
acatctggaa gctgcagtgg gccaccacca tcctggacat tgagcgctcc ttccccgtat   2160
tcctgaggaa ggccttccgc tctggggaga tggtcaccgt gggcaagagc tcggacggca   2220
ctcctgaccg caggtggtgc ttcagggtgg atgaggtgaa ctggtctcac tggaaccaga   2280
acttgggcat catcaacgag gacccgggca agaatgagac ctaccagtat tatggcttct   2340
cgcataccgt gggccgcctc cgcagggatc gctggtcctc ggtggtaccc cgcgtggtgg   2400
aactgaacaa gaactcgaac ccggacgagg tggtggtgcc tctggacagc atggggaacc   2460 ccgctgcga  tggccaccag cagggttacc cccgcaagtg gaggactgat gacgccccgc   2520
tctagggact gcagcccagc cccagcttct ctgcccactc atttctagtc cagccgcatt   2580
tcagcagtgc cttctggggt gtccccccac accctgcttt ggcccagag  gcgagggacc   2640
```

| | | | | | |
|---|---|---|---|---|---|
| agtggaggtg | ccagggaggc | cccaggaccc | tgtggtcccc | tggctctgcc | tccccaccct 2700 |
| ggggtggggg | ctcccggcca | cctgtcttgc | tcctatggag | tcacataagc | caacgccaga 2760 |
| gcccctccac | ctcaggcccc | agcccctgcc | tctccattat | ttatttgctc | tgctctcagg 2820 |
| aagcgacgtg | acccctgccc | cagctggaac | ctggcagagg | ccttaggacc | ccgttccaag 2880 |
| tgcactgccc | ggccaagccc | cagcctcagc | ctgcgcctga | gctgcatgcg | ccaccatttt 2940 |
| tggcagcgtg | gcagctttgc | aaggggctgg | ggccctcggc | gtggggccat | gccttctgtg 3000 |
| tgttctgtag | tgtctgggat | ttgccggtgc | tcaataaatg | tttattcatt | gacggtg 3057 |